United States Patent
Daughtridge et al.

(10) Patent No.: US 11,795,239 B2
(45) Date of Patent: Oct. 24, 2023

(54) PRODUCTS AND METHODS FOR MONITORING ADHERENCE TO NUCLEOSIDE REVERSE TRANSCRIPTASE INHIBITOR THERAPY

(71) Applicant: UrSure, Inc., Boston, MA (US)

(72) Inventors: Giffin Daughtridge, Cambridge, MA (US); Keith Kardos, Bethlehem, PA (US)

(73) Assignee: OraSure Technologies, Inc., Bethlehem, PA (US)

(*) Notice: Subject to any disclaimer, the term of this patent is extended or adjusted under 35 U.S.C. 154(b) by 580 days.

(21) Appl. No.: 16/755,100

(22) PCT Filed: Oct. 15, 2018

(86) PCT No.: PCT/US2018/055961
§ 371 (c)(1),
(2) Date: Apr. 9, 2020

(87) PCT Pub. No.: WO2019/075487
PCT Pub. Date: Apr. 18, 2019

(65) Prior Publication Data
US 2020/0239598 A1    Jul. 30, 2020

Related U.S. Application Data

(60) Provisional application No. 62/572,126, filed on Oct. 13, 2017.

(51) Int. Cl.
| | |
|---|---|
| *C07K 16/44* | (2006.01) |
| *G01N 33/53* | (2006.01) |
| *G01N 33/543* | (2006.01) |
| *C07F 9/6561* | (2006.01) |
| *A61K 47/64* | (2017.01) |

(52) U.S. Cl.
CPC ............ *C07K 16/44* (2013.01); *A61K 47/646* (2017.08); *C07F 9/65616* (2013.01); *G01N 33/5308* (2013.01); *G01N 33/543* (2013.01); *G01N 33/54388* (2021.08); *C07K 2317/565* (2013.01)

(58) Field of Classification Search
CPC . A61K 47/643; A61K 47/646; C07F 9/65616; C07K 16/44; C07K 2317/565; G01N 33/5308; G01N 33/543; G01N 33/558
See application file for complete search history.

(56) References Cited

U.S. PATENT DOCUMENTS

| | | | |
|---|---|---|---|
| 2007/0218486 A1* | 9/2007 | Valdez | C07K 16/44 435/5 |
| 2011/0200609 A1 | 8/2011 | Glabe et al. | |
| 2014/0127209 A1 | 5/2014 | Grabstein et al. | |
| 2022/0196641 A1* | 6/2022 | Daughtridge | G01N 33/5308 |

FOREIGN PATENT DOCUMENTS

| | | |
|---|---|---|
| WO | 2007103740 A2 | 9/2007 |
| WO | 2017147186 A1 | 8/2017 |
| WO | 2019/018747 A1 | 1/2019 |

OTHER PUBLICATIONS

A print-out retrieved from https://en.wikipedia.org/wiki/ Complementarity-determining_region on Feb. 2, 2023.*
Koenig et al., "Urine Assay for Tenofovir to Monitor Adherence to Tenofovir-Emtricitabine as PrEP," 2015 Conference on Retroviruses and Opportunistic Infections (CROI), Feb. 23-26, 2015 | Seattle, Washington, Abstract No. 975, retrieved from https://www.croiconference.org/abstract/urine-assay-tenofovir-monitor.*
Adherence-tenofovir-emtricitabine-prep/ on Feb. 3, 2023 (three pages total) (continuation of recitation from V).*
International Search Report in International Application No. PCT/US2018/055961, dated Jan. 28, 2019.
Aliakbarinodehi et al., "Aptamer-based Field-Effect Biosensor for Tenofovir Detection", Scientific Reports, 2017, vol. 7, No. 1.
Koczula et al., "Lateral flow assays", Essays in Biochemistry, 2016, pp. 111-120, vol. 60, No. 1.
Boettiger et al., Tenofovir-based antiretroviral therapy in HBV-HIV coinfection: results from the Treat Asia HIV Observational Database, Antiviral Therapy, 2016, pp. 27-35, vol. 21. No. 1.
"8-amino[1'-(4'-aminobutyl)]-adenine", Database PubChem Substance [Online] NCBI, 2017.
Koenig et al."Urine assay for tenofovir to monitor adherence in real time to tenofovir disoproxil fumarate/emtricitabine as pre-exposure prophylaxis", HIV Medicine, 2017, pp. 412-418, vol. 18, No. 6, British HIV Association.
Pratt et al., "A Competitive Lateral Flow Assay for the Detection of Tenofovir", Analytica Chimica Acta, 2018, pp. 34-40, vol. 1017.
Gandhi et al., "Development and validation of the first point-of-care assay to objectively monitor adherence to HIV treatment and prevention in real-time in routine settings", Concise Communication, 2020, pp. 255-260, vol. 34, No. 2.
Ondrej Baszczynski et al., "Synthesis and antiviral activity of N9-[3-fluoro-2-(phosphonomethoxy)propyl] analogues derived from N6-substituted adenines and 2,6-diaminopurines," Bioorganic & Medicinal Chemistry, vol. 19, 2011, pp. 2114-2124.
Zdenek Zidek et al., "Immunobiological activity of N-[2-(phosphonomethoxy)alkyl] derivatives of N6-substituted adenines, and 2,6-diaminopurines," European Journal of Pharmacology, vol. 475, 2003, pp. 149-159.

(Continued)

*Primary Examiner* — Galina M. Yakovleva
(74) *Attorney, Agent, or Firm* — RAPHAEL BELLUM PLLC

(57) ABSTRACT

The invention provides novel compounds, reagents, systems, and methods for detecting a metabolite related to a NRTI in a biological sample, and use thereof in monitoring adherence to pre-exposure prophylaxis or anti-retroviral treatment. Such reagents comprise NRTI derivatives, analogs, NRTI derivatives conjugates, along with antibodies directed to same, which are useful for anti-body-based methods, such as a lateral flow immunoassay and other point of care devices.

18 Claims, 6 Drawing Sheets

Specification includes a Sequence Listing.

(56) References Cited

OTHER PUBLICATIONS

Moolchand Kurmi et al., "Stability behaviour of antiretroviral drugs and their combinations. 3: Characterization of interaction products of emtricitabine and tenofovir disoproxil fumarate by mass spectrometry," Journal of Pharmaceutical and Biomedical Analysis, vol. 128, 2016, pp. 438-446.

"8-amino [1'-(4'-aminobutyl)]-adenine," SID 341716721, PubChem, Sep. 13, 2017.

* cited by examiner

SEQUENCE LISTING

```
<160> NUMBER OF SEQ ID NOS: 42

<210> SEQ ID NO 1
<211> LENGTH: 238
<212> TYPE: PRT
<213> ORGANISM: Artificial Sequence
<220> FEATURE:
<223> OTHER INFORMATION: Synthetic polypeptide

<400> SEQUENCE: 1

Met Asp Met Arg Ala Pro Thr Gln Leu Leu Gly Leu Leu Leu Leu Trp
1               5                   10                  15

Leu Pro Gly Ala Arg Cys Ala Asp Ile Val Met Thr Gln Thr Pro Ser
            20                  25                  30

Ser Val Ser Ala Ala Val Gly Gly Thr Val Thr Ile Asn Cys Gln Ala
        35                  40                  45

Ser Gln Ser Ile Gly Asn Tyr Cys Ser Trp Tyr Gln Gln Lys Pro Gly
    50                  55                  60

Gln Pro Pro Lys Leu Leu Ile Tyr Leu Ala Ser Asn Leu Ala Ser Gly
65                  70                  75                  80

Val Pro Ser Arg Phe Lys Gly Ser Gly Ser Gly Thr Gln Phe Thr Leu
            85                  90                  95

Thr Ile Ser Asp Leu Glu Cys Ala Asp Ala Ala Thr Tyr Tyr Cys Gln
            100                 105                 110

Ser Asn Tyr Trp Thr Thr Ser Val Asn Tyr Gly Pro Phe Gly Gly Gly
            115                 120                 125

Thr Glu Val Val Val Glu Gly Asp Pro Val Ala Pro Thr Val Leu Ile
            130                 135                 140

Phe Pro Pro Ala Ala Asp Gln Val Ala Thr Gly Thr Val Thr Ile Val
145                 150                 155                 160

Cys Val Ala Asn Lys Tyr Phe Pro Asp Val Thr Val Thr Trp Glu Val
            165                 170                 175

Asp Gly Thr Thr Gln Thr Thr Gly Ile Glu Asn Ser Lys Thr Pro Gln
            180                 185                 190

Asn Ser Ala Asp Cys Thr Tyr Asn Leu Ser Ser Thr Leu Thr Leu Thr
            195                 200                 205

Ser Thr Gln Tyr Asn Ser His Lys Glu Tyr Thr Cys Lys Val Thr Gln
    210                 215                 220

Gly Thr Thr Ser Val Val Gln Ser Phe Asn Arg Gly Asp Cys
225                 230                 235
```

```
<210> SEQ ID NO 2
<211> LENGTH: 456
<212> TYPE: PRT
<213> ORGANISM: Artificial Sequence
<220> FEATURE:
<223> OTHER INFORMATION: Synthetic polypeptide

<400> SEQUENCE: 2

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
            20                  25                  30

Gly Thr Pro Leu Thr Leu Thr Cys Thr Val Ser Gly Ile Asp Leu Asn
        35                  40                  45

Arg Tyr Ser Val Gly Trp Val Arg Gln Ala Pro Gly Glu Gly Leu Glu
    50                  55                  60

Trp Ile Gly Tyr Ile Tyr Arg Thr Gly Thr Thr Trp Tyr Ala Asn Trp
65                  70                  75                  80

Val Lys Gly Arg Phe Thr Ile Ser Lys Thr Ser Thr Val Asp Leu
                85                  90                  95

Lys Met Thr Ser Leu Thr Thr Glu Asp Thr Ala Thr Tyr Phe Cys Ala
                100                 105                 110

Arg Thr Gly Thr Ser Ile Ala Thr Asp Ile Trp Gly Pro Gly Thr Leu
            115                 120                 125

Val Thr Val Ser Ser Gly Gln Pro Lys Ala Pro Ser Val Phe Pro Leu
        130                 135                 140

Ala Pro Cys Cys Gly Asp Thr Pro Ser Ser Thr Val Thr Leu Gly Cys
145                 150                 155                 160

Leu Val Lys Gly Tyr Leu Pro Glu Pro Val Thr Val Thr Trp Asn Ser
                165                 170                 175

Gly Thr Leu Thr Asn Gly Val Arg Thr Phe Pro Ser Val Arg Gln Ser
            180                 185                 190

Ser Gly Leu Tyr Ser Leu Ser Ser Val Val Ser Val Thr Ser Ser Ser
        195                 200                 205

Gln Pro Val Thr Cys Asn Val Ala His Pro Ala Thr Asn Thr Lys Val
    210                 215                 220

Asp Lys Thr Val Ala Pro Ser Thr Cys Ser Lys Pro Thr Cys Pro Pro
225                 230                 235                 240

Pro Glu Leu Leu Gly Arg Ser Ser Val Phe Ile Phe Pro Pro Lys Pro
                245                 250                 255

Lys Asp Thr Leu Met Ile Ser Arg Thr Pro Glu Val Thr Cys Val Val
            260                 265                 270

Val Asp Val Ser Gln Asp Asp Pro Glu Val Gln Phe Thr Trp Tyr Ile
        275                 280                 285

Asn Asn Glu Gln Val Arg Thr Ala Arg Pro Pro Leu Arg Glu Gln Gln
    290                 295                 300

Phe Asn Ser Thr Ile Arg Val Val Ser Thr Leu Pro Ile Ala His Gln
305                 310                 315                 320

Asp Trp Leu Arg Gly Lys Glu Phe Lys Cys Lys Val His Asn Lys Ala
                325                 330                 335

Leu Pro Ala Pro Ile Glu Lys Thr Ile Ser Lys Ala Arg Gly Gln Pro
            340                 345                 350

Leu Glu Pro Lys Val Tyr Thr Met Gly Pro Pro Arg Glu Glu Leu Ser
        355                 360                 365
```

```
Ser Arg Ser Val Ser Leu Thr Cys Met Ile Asn Gly Phe Tyr Pro Ser
    370                 375                 380

Asp Ile Ser Val Glu Trp Glu Lys Asn Gly Lys Ala Glu Asp Asn Tyr
385                 390                 395                 400

Lys Thr Thr Pro Thr Val Leu Asp Ser Asp Gly Ser Tyr Phe Leu Tyr
                405                 410                 415

Ser Lys Leu Ser Val Pro Thr Ser Glu Trp Gln Arg Gly Asp Val Phe
                420                 425                 430

Thr Cys Ser Val Met His Glu Ala Leu His Asn His Tyr Thr Gln Lys
                435                 440                 445

Ser Ile Ser Arg Ser Pro Gly Lys
    450                 455

<210> SEQ ID NO 3
<211> LENGTH: 239
<212> TYPE: PRT
<213> ORGANISM: Artificial Sequence
<220> FEATURE:
<223> OTHER INFORMATION: Synthetic polypeptide

<400> SEQUENCE: 3

Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Pro Ser Ser
                20                  25                  30

Val Ser Ala Ala Val Gly Gly Thr Val Thr Ile Asn Cys Gln Ser Ser
                35                  40                  45

Gln Asn Val Tyr Lys Asp Asn Tyr Leu Ala Trp Tyr Gln Gln Lys Pro
    50                  55                  60

Gly Gln Pro Pro Lys Arg Leu Ile Tyr Tyr Ala Ser Thr Leu Ala Ser
65                  70                  75                  80

Gly Val Pro Ser Arg Phe Ser Gly Ser Gly Ser Gly Thr Gln Phe Thr
                85                  90                  95

Leu Thr Ile Ser Asp Val Gln Cys Asp Asp Ala Ala Thr Tyr Tyr Cys
                100                 105                 110

Ala Gly Ala Tyr Asp Cys Arg Ser Gly Asp Cys Arg Ala Phe Gly Gly
                115                 120                 125

Gly Thr Glu Val Val Val Lys Gly Asp Pro Val Ala Pro Thr Val Leu
130                 135                 140

Ile Phe Pro Pro Ala Ala Asp Gln Val Ala Thr Gly Thr Val Thr Ile
145                 150                 155                 160

Val Cys Val Ala Asn Lys Tyr Phe Pro Asp Val Thr Val Thr Trp Glu
                165                 170                 175

Val Asp Gly Thr Thr Gln Thr Thr Gly Ile Glu Asn Ser Lys Thr Pro
                180                 185                 190

Gln Asn Ser Ala Asp Cys Thr Tyr Asn Leu Ser Ser Thr Leu Thr Leu
                195                 200                 205

Thr Ser Thr Gln Tyr Asn Ser His Lys Glu Tyr Thr Cys Lys Val Thr
                210                 215                 220

Gln Gly Thr Thr Ser Val Val Gln Ser Phe Asn Arg Gly Asp Cys
225                 230                 235

<210> SEQ ID NO 4
<211> LENGTH: 457
<212> TYPE: PRT
<213> ORGANISM: Artificial Sequence
<220> FEATURE:
```

<223> OTHER INFORMATION: Synthetic polypeptide

<400> SEQUENCE: 4

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Gly Ser Leu Thr Leu Thr Cys Thr Ala Ser Gly Phe Ser Leu Ser
        35                  40                  45

Ser Tyr Asn Met Gln Trp Val Arg Gln Ala Pro Gly Lys Gly Leu Glu
    50                  55                  60

Tyr Ile Gly Tyr Ile Phe Ser Thr Gly Phe Thr Tyr Tyr Ala Ser Trp
65                  70                  75                  80

Ala Lys Gly Arg Phe Thr Ile Ser Lys Thr Ser Thr Thr Val Asp Leu
                85                  90                  95

Lys Met Thr Ser Leu Thr Thr Glu Asp Thr Ala Thr Tyr Phe Cys Ala
            100                 105                 110

Arg Gly Ser Thr Ala Lys Gly Asp Arg Asp Ile Trp Gly Pro Gly Thr
        115                 120                 125

Leu Val Thr Val Ser Leu Gly Gln Pro Lys Ala Pro Ser Val Phe Pro
130                 135                 140

Leu Ala Pro Cys Cys Gly Asp Thr Pro Ser Ser Thr Val Thr Leu Gly
145                 150                 155                 160

Cys Leu Val Lys Gly Tyr Leu Pro Glu Pro Val Thr Val Thr Trp Asn
                165                 170                 175

Ser Gly Thr Leu Thr Asn Gly Val Arg Thr Phe Pro Ser Val Arg Gln
            180                 185                 190

Ser Ser Gly Leu Tyr Ser Leu Ser Ser Val Val Ser Val Thr Ser Ser
        195                 200                 205

Ser Gln Pro Val Thr Cys Asn Val Ala His Pro Ala Thr Asn Thr Lys
    210                 215                 220

Val Asp Lys Thr Val Ala Pro Ser Thr Cys Ser Lys Pro Thr Cys Pro
225                 230                 235                 240

Pro Pro Glu Leu Leu Gly Arg Ser Ser Val Phe Ile Phe Pro Pro Lys
                245                 250                 255

Pro Lys Asp Thr Leu Met Ile Ser Arg Thr Pro Glu Val Thr Cys Val
            260                 265                 270

Val Val Asp Val Ser Gln Asp Asp Pro Glu Val Gln Phe Thr Trp Tyr
        275                 280                 285

Ile Asn Asn Glu Gln Val Arg Thr Ala Arg Pro Pro Leu Arg Glu Gln
    290                 295                 300

Gln Phe Asn Ser Thr Ile Arg Val Val Ser Thr Leu Pro Ile Ala His
305                 310                 315                 320

Gln Asp Trp Leu Arg Gly Lys Glu Phe Lys Cys Lys Val His Asn Lys
                325                 330                 335

Ala Leu Pro Ala Pro Ile Glu Lys Thr Ile Ser Lys Ala Arg Gly Gln
            340                 345                 350

Pro Leu Glu Pro Lys Val Tyr Thr Met Gly Pro Pro Arg Glu Glu Leu
        355                 360                 365

Ser Ser Arg Ser Val Ser Leu Thr Cys Met Ile Asn Gly Phe Tyr Pro
    370                 375                 380

Ser Asp Ile Ser Val Glu Trp Glu Lys Asn Gly Lys Ala Glu Asp Asn
385                 390                 395                 400

Tyr Lys Thr Thr Pro Thr Val Leu Asp Ser Asp Gly Ser Tyr Phe Leu
                405                 410                 415

Tyr Ser Lys Leu Ser Val Pro Thr Ser Glu Trp Gln Arg Gly Asp Val
            420                 425                 430

Phe Thr Cys Ser Val Met His Glu Ala Leu His Asn His Tyr Thr Gln
        435                 440                 445

Lys Ser Ile Ser Arg Ser Pro Gly Lys
    450                 455

<210> SEQ ID NO 5
<211> LENGTH: 239
<212> TYPE: PRT
<213> ORGANISM: Artificial Sequence
<220> FEATURE:
<223> OTHER INFORMATION: Synthetic polypeptide

<400> SEQUENCE: 5

Met Asp Thr Arg Ala Pro Thr Gln Leu Leu Gly Leu Leu Leu Leu Trp
1               5                   10                  15

Leu Pro Gly Ala Arg Cys Ala Glu Val Val Met Thr Gln Thr Pro Ala
            20                  25                  30

Ser Val Glu Ala Ala Val Gly Asp Thr Val Thr Ile Lys Cys Gln Ala
        35                  40                  45

Ser Gln Ser Ile Ser Ser Tyr Leu Asn Trp Tyr Gln Gln Lys Pro Gly
    50                  55                  60

Gln Pro Pro Lys Leu Leu Ile Tyr Arg Ala Ser Asn Leu Arg Ser Gly
65                  70                  75                  80

Val Pro Ser Arg Phe Lys Gly Ser Gly Ser Gly Thr Gln Phe Thr Leu
                85                  90                  95

Thr Ile Ser Asp Leu Glu Cys Ala Asp Ala Ala Thr Tyr Tyr Cys Gln
            100                 105                 110

Ser Asn Tyr Tyr Ser Arg Ser Thr Asn Tyr Val Val Pro Phe Gly Gly
        115                 120                 125

Gly Thr Glu Val Val Val Lys Gly Asp Pro Val Ala Pro Thr Val Leu
    130                 135                 140

Ile Phe Pro Pro Ser Ala Asp Leu Val Ala Thr Gly Thr Val Thr Ile
145                 150                 155                 160

Val Cys Val Ala Asn Lys Tyr Phe Pro Asp Val Thr Val Thr Trp Glu
                165                 170                 175

Val Asp Gly Thr Thr Gln Thr Thr Gly Ile Glu Asn Ser Lys Thr Pro
            180                 185                 190

Gln Asn Ser Ala Asp Cys Thr Tyr Asn Leu Ser Ser Thr Leu Thr Leu
        195                 200                 205

Thr Ser Thr Gln Tyr Asn Ser His Lys Glu Tyr Thr Cys Lys Val Thr
    210                 215                 220

Gln Gly Thr Thr Ser Val Val Gln Ser Phe Asn Arg Gly Asp Cys
225                 230                 235

<210> SEQ ID NO 6
<211> LENGTH: 457
<212> TYPE: PRT
<213> ORGANISM: Artificial Sequence
<220> FEATURE:
<223> OTHER INFORMATION: Synthetic polypeptide

<400> SEQUENCE: 6

Met Glu Thr Gly Leu Arg Trp Leu Leu Leu Val Ala Val Leu Lys Gly
1               5                   10                  15

```
Val Gln Cys Gln Ser Leu Glu Glu Ser Gly Gly Arg Leu Val Thr Pro
             20                  25                  30

Gly Thr Pro Leu Thr Leu Thr Cys Thr Val Ser Gly Phe Ser Leu Ser
         35                  40                  45

Ser Ser Ser Met Gly Trp Val Arg Gln Ala Pro Gly Lys Gly Leu Glu
 50                  55                  60

Trp Ile Gly Tyr Ile Tyr Ala Gly Ser Gly Ser Arg Tyr Tyr Ala Ser
 65                  70                  75                  80

Trp Ala Asn Gly Arg Phe Thr Ile Ser Lys Thr Ser Thr Thr Val Asp
                 85                  90                  95

Leu Lys Ile Thr Ser Pro Thr Thr Glu Asp Thr Ala Thr Tyr Phe Cys
             100                 105                 110

Gly Arg Val Thr Ser Asn Gly Asp Asn Asn Ile Trp Gly Pro Gly Thr
         115                 120                 125

Leu Val Thr Val Ser Ser Gly Gln Pro Lys Ala Pro Ser Val Phe Pro
130                 135                 140

Leu Ala Pro Cys Cys Gly Asp Thr Pro Ser Ser Thr Val Thr Leu Gly
145                 150                 155                 160

Cys Leu Val Lys Gly Tyr Leu Pro Glu Pro Val Thr Val Thr Trp Asn
                 165                 170                 175

Ser Gly Thr Leu Thr Asn Gly Val Arg Thr Phe Pro Ser Val Arg Gln
             180                 185                 190

Ser Ser Gly Leu Tyr Ser Leu Ser Ser Val Val Ser Val Thr Ser Ser
         195                 200                 205

Ser Gln Pro Val Thr Cys Asn Val Ala His Pro Ala Thr Asn Thr Lys
     210                 215                 220

Val Asp Lys Thr Val Ala Pro Ser Thr Cys Ser Lys Pro Thr Cys Pro
225                 230                 235                 240

Pro Pro Glu Leu Leu Gly Arg Ser Ser Val Phe Ile Phe Pro Pro Lys
                 245                 250                 255

Pro Lys Asp Thr Leu Met Ile Ser Arg Thr Pro Glu Val Thr Cys Val
             260                 265                 270

Val Val Asp Val Ser Gln Asp Asp Pro Glu Val Gln Phe Thr Trp Tyr
         275                 280                 285

Ile Asn Asn Glu Gln Val Arg Thr Ala Arg Pro Pro Leu Arg Glu Gln
290                 295                 300

Gln Phe Asn Ser Thr Ile Arg Val Val Ser Thr Leu Pro Ile Ala His
305                 310                 315                 320

Gln Asp Trp Leu Arg Gly Lys Glu Phe Lys Cys Lys Val His Asn Lys
                 325                 330                 335

Ala Leu Pro Ala Pro Ile Glu Lys Thr Ile Ser Lys Ala Arg Gly Gln
             340                 345                 350

Pro Leu Glu Pro Lys Val Tyr Thr Met Gly Pro Pro Arg Glu Glu Leu
         355                 360                 365

Ser Ser Arg Ser Val Ser Leu Thr Cys Met Ile Asn Gly Phe Tyr Pro
370                 375                 380

Ser Asp Ile Ser Val Glu Trp Glu Lys Asn Gly Lys Ala Glu Asp Asn
385                 390                 395                 400

Tyr Lys Thr Thr Pro Thr Val Leu Asp Ser Asp Gly Ser Tyr Phe Leu
                 405                 410                 415

Tyr Ser Lys Leu Ser Val Pro Thr Ser Glu Trp Gln Arg Gly Asp Val
             420                 425                 430
```

Phe Thr Cys Ser Val Met His Glu Ala Leu His Asn His Tyr Thr Gln
         435                 440                 445

Lys Ser Ile Ser Arg Ser Pro Gly Lys
    450                 455

<210> SEQ ID NO 7
<211> LENGTH: 219
<212> TYPE: PRT
<213> ORGANISM: Artificial Sequence
<220> FEATURE:
<223> OTHER INFORMATION: Synthetic polypeptide

<400> SEQUENCE: 7

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Gly
                85                  90                  95

Thr His Val Pro Leu Thr Phe Gly Ala Gly Thr Lys Leu Glu Leu Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215

<210> SEQ ID NO 8
<211> LENGTH: 660
<212> TYPE: DNA
<213> ORGANISM: Artificial Sequence
<220> FEATURE:
<223> OTHER INFORMATION: Synthetic polynucleotide

<400> SEQUENCE: 8
gatgttgtga tgacccaaac tccactctcc ctgcctgtca gtcttggaga tcaagcctcc      60
atctcttgca gatctagtca gagccttgta cacagtaatg aaacacccta tttacattgg     120
tacctgcaga agccaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tctgggagtt tatttctgct ctcaaggtac acatgttccg     300
ctcacgttcg gtgctgggac caagctggag ctgaaacggg ctgatgctgc accaactgta     360

```
tccatcttcc caccatccag tgagcagtta acatctggag gtgcctcagt cgtgtgcttc    420
ttgaacaact tctaccccaa agacatcaat gtcaagtgga agattgatgg cagtgaacga    480
caaaatggcg tcctgaacag ttggactgat caggacagca agacagcac ctacagcatg    540 agcagcaccc tcacgttgac caaggacgag tatgaacgac ataacagcta cctgtgagag    600
gccactcaca agacatcaac ttcacccatt gtcaagagct tcaacaggaa tgagtgttag    660
```

<210> SEQ ID NO 9
<211> LENGTH: 440
<212> TYPE: PRT
<213> ORGANISM: Artificial Sequence
<220> FEATURE:
<223> OTHER INFORMATION: Synthetic polypeptide

<400> SEQUENCE: 9

```
Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Ala Leu Glu Trp Leu
        35                  40                  45

Gly Leu Ile Arg Asn Lys Ala Lys Gly Tyr Thr Thr Glu Tyr Ser Ala
    50                  55                  60

Ser Val Lys Gly Arg Phe Thr Ile Ser Arg Asp Asn Ser Gln Ser Ile
65                  70                  75                  80

Leu Tyr Leu Gln Met Asn Thr Leu Arg Ala Glu Asp Ser Ala Thr Tyr
                85                  90                  95

Tyr Cys Ala Arg Glu Ala Leu Pro Tyr Trp Gly Gln Gly Thr Leu Val
            100                 105                 110

Thr Val Ser Ala Ala Lys Thr Thr Pro Pro Ser Val Tyr Pro Leu Ala
        115                 120                 125

Pro Gly Ser Ala Ala Gln Thr Asn Ser Met Val Thr Leu Gly Cys Leu
    130                 135                 140

Val Lys Gly Tyr Phe Pro Glu Pro Val Thr Val Thr Trp Asn Ser Gly
145                 150                 155                 160

Ser Leu Ser Ser Gly Val His Thr Phe Pro Ala Val Leu Gln Ser Asp
                165                 170                 175

Leu Tyr Thr Leu Ser Ser Ser Val Thr Val Pro Ser Ser Thr Trp Pro
            180                 185                 190

Ser Glu Thr Val Thr Cys Asn Val Ala His Pro Ala Ser Ser Thr Lys
        195                 200                 205

Val Asp Lys Lys Ile Val Pro Arg Asp Cys Gly Cys Lys Pro Cys Ile
    210                 215                 220

Cys Thr Val Pro Glu Val Ser Ser Val Phe Ile Phe Pro Pro Lys Pro
225                 230                 235                 240

Lys Asp Val Leu Thr Ile Thr Leu Thr Pro Lys Val Thr Cys Val Val
                245                 250                 255

Val Asp Ile Ser Lys Asp Asp Pro Glu Val Gln Phe Ser Trp Phe Val
            260                 265                 270

Asp Asp Val Glu Val His Thr Ala Gln Thr Gln Pro Arg Glu Glu Gln
        275                 280                 285

Phe Asn Ser Thr Phe Arg Ser Val Ser Glu Leu Pro Ile Met His Gln
    290                 295                 300

Asp Trp Leu Asn Gly Lys Glu Phe Lys Cys Arg Val Asn Ser Ala Ala
```

| | | | | 305 | | | | | 310 | | | | | 315 | | | | | 320 |

Phe Pro Ala Pro Ile Glu Lys Thr Ile Ser Lys Thr Lys Gly Arg Pro
                         325                     330                    335

Lys Ala Pro Gln Val Tyr Thr Ile Pro Pro Lys Glu Gln Met Ala
                 340                      345                   350

Lys Asp Lys Val Ser Leu Thr Cys Met Ile Thr Asp Phe Phe Pro Glu
               355                     360                 365

Asp Ile Thr Val Glu Trp Gln Trp Asn Gly Gln Pro Ala Glu Asn Tyr
370                    375                   380

Lys Asn Thr Gln Pro Ile Met Asp Thr Asp Gly Ser Tyr Phe Val Tyr
385                    390                   395                400

Ser Lys Leu Asn Val Gln Lys Ser Asn Trp Glu Ala Gly Asn Thr Phe
                 405                     410                 415

Thr Cys Ser Val Leu His Glu Gly Leu His Asn His His Thr Glu Lys
               420                     425                 430

Ser Leu Ser His Ser Pro Gly Lys
               435                     440

<210> SEQ ID NO 10
<211> LENGTH: 1323
<212> TYPE: DNA
<213> ORGANISM: Artificial Sequence
<220> FEATURE:
<223> OTHER INFORMATION: Synthetic polynucleotide

<400> SEQUENCE: 10

```
gaggtgaagc tggtggagtc tggaggaggc ttggtacagc ctgggggttc tctgagactc    60
tcctgtgcaa cttctgggtt caccttcact gattactaca tgagctgggt ccgccagcct   120
ccaggaaagg cacttgagtg gttgggtctt attagaaaca agctaaagg ttacacaaca   180 gagtacagtg catctgtgaa gggtcggttc accatctcca gagataattc ccaaagcatc   240
ctctatcttc aaatgaacac cctgagagct gaggacagtg ccacttatta ctgtgcaaga   300
gaggccctac cttactgggg ccaagggact ctggtcactg tctctgcagc caaaacgaca   360
cccccatctg tctatccact ggcccctgga tctgctgccc aaactaactc catggtgacc   420
ctgggatgcc tggtcaaggg ctatttccct gagccagtga cagtgacctg aactctgga   480 tccctgtcca gcggtgtgca caccttccca gctgtcctgc agtctgacct ctacactctg   540
agcagctcag tgactgtccc ctccagcacc tggcccagcg agaccgtcac ctgcaacgtt   600
gcccacccgg ccagcagcac caaggtggac aagaaaattg tgcccaggga ttgtggttgt   660
aagccttgca tatgtacagt cccagaagta tcatctgtct tcatcttccc cccaaagccc   720
aaggatgtgc tcaccattac tctgactcct aaggtcacgt gtgttgtggt agacatcagc   780
aaggatgatc ccgaggtcca gttcagctgg tttgtagatg atgtggaggt gcacacagct   840
cagacgcaac cccgggagga gcagttcaac agcactttcc gctcagtcag tgaacttccc   900
atcatgcacc aggactggct caatggcaag gagttcaaat gcagggtcaa cagtgcagct   960
ttccctgccc ccatcgagaa aaccatctcc aaaaccaaag gcagaccgaa ggctccacag  1020
gtgtacacca ttccacctcc caaggagcag atggccaagg ataaagtcag tctgacctgc  1080
atgataacag acttcttccc tgaagacatt actgtggagt ggcagtggaa tgggcagcca  1140
gcggagaact acaagaacac tcagcccatc atggacacag atggctctta cttcgtctac  1200
agcaagctca atgtgcagaa gagcaactgg gaggcaggaa atactttcac ctgctctgtg  1260
ttacatgagg gcctgcacaa ccaccatact gagaagagcc tctcccactc tcctggtaaa  1320
``` tga                                                                  1323

<210> SEQ ID NO 11
<211> LENGTH: 77
<212> TYPE: PRT
<213> ORGANISM: Artificial Sequence
<220> FEATURE:
<223> OTHER INFORMATION: Synthetic polypeptide

<400> SEQUENCE: 11

Ala Ser Gln Ser Ile Gly Asn Tyr Cys Ser Trp Tyr Gln Gln Lys Pro
1               5                   10                  15

Gly Gln Pro Pro Lys Leu Leu Ile Tyr Leu Ala Ser Asn Leu Ala Ser
            20                  25                  30

Gly Val Pro Ser Arg Phe Lys Gly Ser Gly Ser Gly Thr Gln Phe Thr
        35                  40                  45

Leu Thr Ile Ser Asp Leu Glu Cys Ala Asp Ala Ala Thr Tyr Tyr Cys
    50                  55                  60

Gln Ser Asn Tyr Trp Thr Thr Ser Val Asn Tyr Gly Pro
65                  70                  75

<210> SEQ ID NO 12
<211> LENGTH: 78
<212> TYPE: PRT
<213> ORGANISM: Artificial Sequence
<220> FEATURE:
<223> OTHER INFORMATION: Synthetic polypeptide

<400> SEQUENCE: 12

Ile Asp Leu Asn Arg Tyr Ser Val Gly Trp Val Arg Gln Ala Pro Gly
1               5                   10                  15

Glu Gly Leu Glu Trp Ile Gly Tyr Ile Tyr Arg Thr Gly Thr Thr Trp
            20                  25                  30

Tyr Ala Asn Trp Val Lys Gly Arg Phe Thr Ile Ser Lys Thr Ser Thr
        35                  40                  45

Thr Val Asp Leu Lys Met Thr Ser Leu Thr Thr Glu Asp Thr Ala Thr
    50                  55                  60

Tyr Phe Cys Ala Arg Thr Gly Thr Ser Ile Ala Thr Asp Ile
65                  70                  75

<210> SEQ ID NO 13
<211> LENGTH: 79
<212> TYPE: PRT
<213> ORGANISM: Artificial Sequence
<220> FEATURE:
<223> OTHER INFORMATION: Synthetic polypeptide

<400> SEQUENCE: 13

Ser Ser Gln Asn Val Tyr Lys Asp Asn Tyr Leu Ala Trp Tyr Gln Gln
1               5                   10                  15

Lys Pro Gly Gln Pro Pro Lys Arg Leu Ile Tyr Ala Ser Thr Leu
            20                  25                  30

Ala Ser Gly Val Pro Ser Arg Phe Ser Gly Ser Gly Ser Gly Thr Gln
        35                  40                  45

Phe Thr Leu Thr Ile Ser Asp Val Gln Cys Asp Ala Ala Thr Tyr
    50                  55                  60

Tyr Cys Ala Gly Ala Tyr Asp Cys Arg Ser Gly Asp Cys Arg Ala
65                  70                  75

```
<210> SEQ ID NO 14
<211> LENGTH: 79
<212> TYPE: PRT
<213> ORGANISM: Artificial Sequence
<220> FEATURE:
<223> OTHER INFORMATION: Synthetic polypeptide

<400> SEQUENCE: 14

Phe Ser Leu Ser Ser Tyr Asn Met Gln Trp Val Arg Gln Ala Pro Gly
1               5                   10                  15

Lys Gly Leu Glu Tyr Ile Gly Tyr Ile Phe Ser Thr Gly Phe Thr Tyr
            20                  25                  30

Tyr Ala Ser Trp Ala Lys Gly Arg Phe Thr Ile Ser Lys Thr Ser Thr
        35                  40                  45

Thr Val Asp Leu Lys Met Thr Ser Leu Thr Thr Glu Asp Thr Ala Thr
    50                  55                  60

Tyr Phe Cys Ala Arg Gly Ser Thr Ala Lys Gly Asp Arg Asp Ile
65                  70                  75

<210> SEQ ID NO 15
<211> LENGTH: 78
<212> TYPE: PRT
<213> ORGANISM: Artificial Sequence
<220> FEATURE:
<223> OTHER INFORMATION: Synthetic polypeptide

<400> SEQUENCE: 15

Ala Ser Gln Ser Ile Ser Ser Tyr Leu Asn Trp Tyr Gln Gln Lys Pro
1               5                   10                  15

Gly Gln Pro Pro Lys Leu Leu Ile Tyr Arg Ala Ser Asn Leu Arg Ser
            20                  25                  30

Gly Val Pro Ser Arg Phe Lys Gly Ser Gly Ser Gly Thr Gln Phe Thr
        35                  40                  45

Leu Thr Ile Ser Asp Leu Glu Cys Ala Asp Ala Ala Thr Tyr Tyr Cys
    50                  55                  60

Gln Ser Asn Tyr Tyr Ser Arg Ser Thr Asn Tyr Val Val Pro
65                  70                  75

<210> SEQ ID NO 16
<211> LENGTH: 79
<212> TYPE: PRT
<213> ORGANISM: Artificial Sequence
<220> FEATURE:
<223> OTHER INFORMATION: Synthetic polypeptide

<400> SEQUENCE: 16

Phe Ser Leu Ser Ser Ser Met Gly Trp Val Arg Gln Ala Pro Gly
1               5                   10                  15

Lys Gly Leu Glu Trp Ile Gly Tyr Ile Tyr Ala Gly Ser Gly Ser Arg
            20                  25                  30

Tyr Tyr Ala Ser Trp Ala Asn Gly Arg Phe Thr Ile Ser Lys Thr Ser
        35                  40                  45

Thr Thr Val Asp Leu Lys Ile Thr Ser Pro Thr Thr Glu Asp Thr Ala
    50                  55                  60

Thr Tyr Phe Cys Gly Arg Val Thr Ser Asn Gly Asp Asn Asn Ile
65                  70                  75

<210> SEQ ID NO 17
<211> LENGTH: 11
<212> TYPE: PRT
<213> ORGANISM: Artificial Sequence
```

```
<220> FEATURE:
<223> OTHER INFORMATION: Synthetic polypeptide

<400> SEQUENCE: 17

Gln Ala Ser Gln Ser Ile Gly Asn Tyr Cys Ser
1               5                   10

<210> SEQ ID NO 18
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 18

Ile Asp Leu Asn Arg Tyr Ser Val Gly
1               5

<210> SEQ ID NO 19
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 19

Gln Ser Ser Gln Asn Val Tyr Lys Asp Asn Tyr Leu Ala
1               5                   10

<210> SEQ ID NO 20
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 20

Phe Ser Leu Ser Ser Tyr Asn Met Gln
1               5

<210> SEQ ID NO 21
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 21

Gln Ala Ser Gln Ser Ile Ser Ser Tyr Leu Asn
1               5                   10

<210> SEQ ID NO 22
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 22

Phe Ser Leu Ser Ser Ser Ser Met Gly
1               5

<210> SEQ ID NO 23
<211> LENGTH: 16
<212> TYPE: PRT
<213> ORGANISM: Artificial Sequence
<220> FEATURE:
```

<223> OTHER INFORMATION: Synthetic polypeptide

<400> SEQUENCE: 23

Arg Ser Ser Gln Ser Leu Val His Ser Asn Gly Asn Thr Tyr Leu His
1               5                   10                  15

<210> SEQ ID NO 24
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 24

Gly Phe Thr Phe Thr Asp Tyr
1               5

<210> SEQ ID NO 25
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 25

Leu Ala Ser Asn Leu Ala Ser
1               5

<210> SEQ ID NO 26
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 26

Tyr Ile Tyr Arg Thr Gly Thr Thr Trp Tyr Ala Asn Trp Val
1               5                   10

<210> SEQ ID NO 27
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 27

Tyr Ala Ser Thr Leu Ala Ser
1               5

<210> SEQ ID NO 28
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 28

Tyr Ile Phe Ser Thr Gly Phe Thr Tyr Tyr Ala Ser Trp Ala
1               5                   10

<210> SEQ ID NO 29
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 29

Arg Ala Ser Asn Leu Arg Ser
1               5

<210> SEQ ID NO 30
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 30

Tyr Ile Tyr Ala Gly Ser Gly Ser Arg Tyr Tyr Ala Ser Trp Ala Asn
1               5                   10                  15

Gly

<210> SEQ ID NO 31
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 31

Lys Val Ser Asn Arg Phe Ser
1               5

<210> SEQ ID NO 32
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 32

Arg Asn Lys Ala Lys Gly Tyr Thr
1               5

<210> SEQ ID NO 33
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 33

Gln Ser Asn Tyr Trp Thr Thr Ser Val Asn Tyr Gly Pro
1               5                   10

<210> SEQ ID NO 34
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 34

Thr Gly Thr Ser Ile Ala Thr Asp Ile
1               5

<210> SEQ ID NO 35
<211> LENGTH: 13
<212> TYPE: PRT
<213> ORGANISM: Artificial Sequence
<220> FEATURE:

```
<223> OTHER INFORMATION: Synthetic polypeptide

<400> SEQUENCE: 35

Ala Gly Ala Tyr Asp Cys Arg Ser Gly Asp Cys Arg Ala
1               5                   10

<210> SEQ ID NO 36
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 36

Gly Ser Thr Ala Lys Gly Asp Arg Asp Ile
1               5                   10

<210> SEQ ID NO 37
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 37

Gln Ser Asn Tyr Tyr Ser Arg Ser Thr Asn Tyr Val Val Pro
1               5                   10

<210> SEQ ID NO 38
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 38

Val Thr Ser Asn Gly Asp Asn Asn Ile
1               5

<210> SEQ ID NO 39
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 39

Ser Gln Gly Thr His Val Pro Leu Thr
1               5

<210> SEQ ID NO 40
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 40

Glu Ala Leu Pro Tyr
1               5

<210> SEQ ID NO 41
<211> LENGTH: 112
<212> TYPE: PRT
<213> ORGANISM: Artificial Sequence
<220> FEATURE:
<223> OTHER INFORMATION: Synthetic polypeptide
```

```
<400> SEQUENCE: 41

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
                20                  25                  30

Asn Gly Asn Thr Tyr Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Gly
                85                  90                  95

Thr His Val Pro Leu Thr Phe Gly Ala Gly Thr Lys Leu Glu Leu Lys
                100                 105                 110

<210> SEQ ID NO 42
<211> LENGTH: 116
<212> TYPE: PRT
<213> ORGANISM: Artificial Sequence
<220> FEATURE:
<223> OTHER INFORMATION: Synthetic polypeptide

<400> SEQUENCE: 42

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
                20                  25                  30

Tyr Met Ser Trp Val Arg Gln Pro Pro Gly Lys Ala Leu Glu Trp Leu
            35                  40                  45

Gly Leu Ile Arg Asn Lys Ala Lys Gly Tyr Thr Thr Glu Tyr Ser Ala
        50                  55                  60

Ser Val Lys Gly Arg Phe Thr Ile Ser Arg Asp Asn Ser Gln Ser Ile
65                  70                  75                  80

Leu Tyr Leu Gln Met Asn Thr Leu Arg Ala Glu Asp Ser Ala Thr Tyr
                85                  90                  95

Tyr Cys Ala Arg Glu Ala Leu Pro Tyr Trp Gly Gln Gly Thr Leu Val
                100                 105                 110

Thr Val Ser Ala
            115
```

PRODUCTS AND METHODS FOR MONITORING ADHERENCE TO NUCLEOSIDE REVERSE TRANSCRIPTASE INHIBITOR THERAPY

RELATED APPLICATIONS

This application is a national stage filing under 35 U.S.C. § 371 of international application number PCT/US2018/055961, filed Oct. 15, 2018, which claims the benefit of U.S. provisional application No. 62/572,126, filed Oct. 13, 2017, each of which is herein incorporated by reference in its entirety.

BACKGROUND

There are 1.2 million people at high-risk of HIV infection in the United States and tens of millions worldwide. In the U.S., an estimated 40,000 people will contract HIV and 14,000 will die in the next year; over 2M will become infected and 1.2 M will die globally (1-4). The U.S. spends about $25 billion on HIV care annually, which will increase dramatically as improvements in HIV treatment increase life expectancies (5).

Pre-exposure prophylaxis (PrEP) with a combination of tenofovir (VIREAD®, Gilead Sciences, Inc., Foster City, Calif.) and emtricitabine (EMTRIVA®, Gilead Sciences, Inc., Foster City, Calif.) effectively prevents HIV infection. In 2010, one clinical trial showed that 2,499 "men who have sex with men" (MSM) and who took PrEP had a 44% reduction in HIV acquisition compared to those who took placebo. That reduction was 99% in those who took PrEP daily (6,7). PrEP has a half-life of 17 hours in blood, and full effectiveness requires daily dosing (8).

Self-reported adherence and pharmacy refill data alone do not correlate well with actual PrEP adherence (9). In young men of color who have sex with men (yMSMc), rates of detectable plasma tenofovir levels dropped to 20% at week 24 after starting PrEP despite high self-reported adherence (10). Similar results were found in trials with women, such as the Fem-PrEP trial (11,12).

Tests for monitoring PrEP adherence, such as plasma, dried blood spot, or hair analysis, can require invasive collection procedures that may not be acceptable to patients, have delays in reporting that prevent implementation of timely interventions, and provide adherence information that may not be reflect recent PrEP use.

Thus, there is a great need for a point-of-care (POC) test for monitoring PrEP adherence that provides noninvasive, painless, quantitative, affordable, and rapid results that can be obtained during a clinical visit in order to provide contemporaneous counsel and improve adherence.

SUMMARY

The present invention depends, in part, upon the development of new products and methods for rapidly testing adherence to PreP therapy or anti-retroviral treatment (ART) in a clinical setting or other POC. In addition, the disclosed products and methods can be used to determine whether elevated viral load is due to non-adherence or resistance, and/or to determine whether drugs contain actual tenofovir (e.g., are not fake), and/or for testing Hepatitis B treatment adherence. The methods involve the use of new antibodies developed against tenofovir using new tenofovir derivatives as immunogens. These antibodies can be employed in immunodiagnostic assays, including lateral flow immunodiagnostic assays, to detect the presence of tenofovir in patient samples, including urine samples.

Thus, in one aspect, the invention provides antibodies that specifically bind to tenofovir or the tenofovir moiety of tenofovir derivatives. In some embodiments, the antibodies have an immunoglobulin heavy chain and an immunoglobulin light chain. In some embodiments, the antibodies are single-chain antibodies, heavy chain only antibodies, Fv fragments, Fab fragments, F(ab)$_2$ fragments, and the like.

In some embodiments, the light chain has a CDR1 region comprising an amino acid sequence selected from the group consisting of SEQ ID NOs: 17, 19, 21, and 30; a CDR2 region comprising an amino acid sequence selected from the group consisting of SEQ ID NOs: 25, 27, 29, and 31; and/or a CDR3 region comprising an amino acid sequence selected from the group consisting of SEQ ID NOs: 33, 35, 37, and 32.

In some embodiments, the antibody comprises a variable light chain amino acid sequence as set forth in SEQ ID NOs: 11, 13, 15, or 41.

In some embodiments, the heavy chain comprises a CDR1 region comprising an amino acid sequence selected from the group consisting of SEQ ID NOs: 18, 20, 22, and 23; a CDR2 region comprising an amino acid sequence selected from the group consisting of SEQ ID NOs: 26, 28, 30, and 31; and/or a CDR3 region comprising an amino acid sequence selected from the group consisting of SEQ ID NOs: 34, 36, 38, and 39.

In some embodiments, the antibody comprises a variable heavy chain amino acid sequence as set forth in SEQ ID NOs: 12, 14, 16, or 42.

Further disclosed are antibody preparations including any one or more of the antibodies disclosed herein. In some embodiments, the preparation is a monoclonal antibody preparation.

Also provided are isolated nucleic acid molecules encoding the heavy chain or light chain of any of the antibodies disclosed herein. In some embodiments, the nucleic acid is selected from the group consisting of a cloning vector, an expression vector, a heterologous recombination vector and a viral integration vector.

In addition, disclosed are cells transformed with any of the nucleic acids provided herein. In some embodiments, the cell is a mammalian cell. Some non-limiting examples of mammalian cells include rabbit, hamster, mouse, rat, chicken, goat, monkey, sheep, pig, horse, cow, or human cell.

In another aspect, the invention provides immunogens and immunogenic preparations for producing antibodies which specifically bind to tenofovir or tenofovir derivatives, or other nucleoside reverse transcriptase inhibitors ("NRTIs") or NRTI-derivatives.

In some embodiments, the immunogens are useful for producing antibodies which specifically bind to tenofovir or tenofovir derivatives. In some embodiments, the immunogens are selected from;

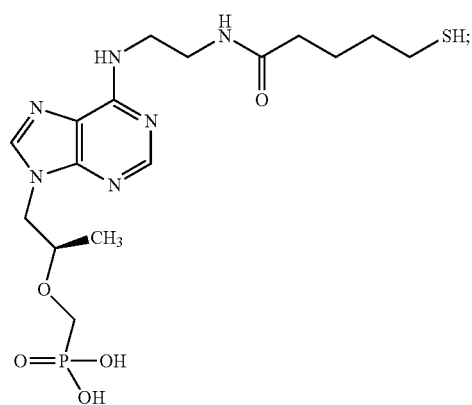
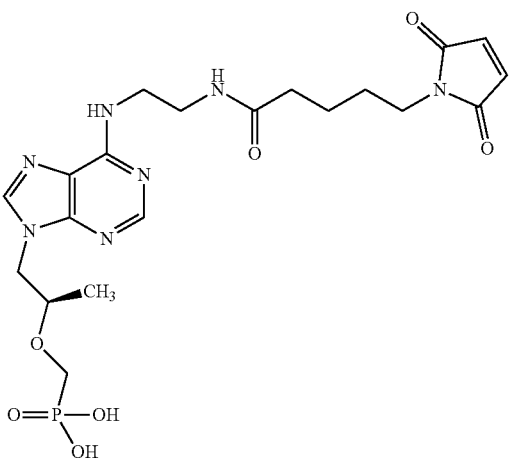
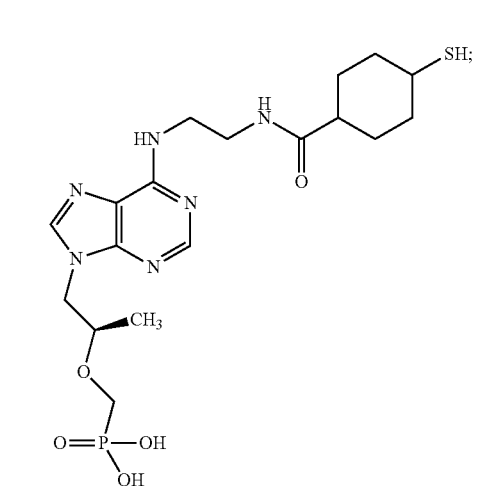
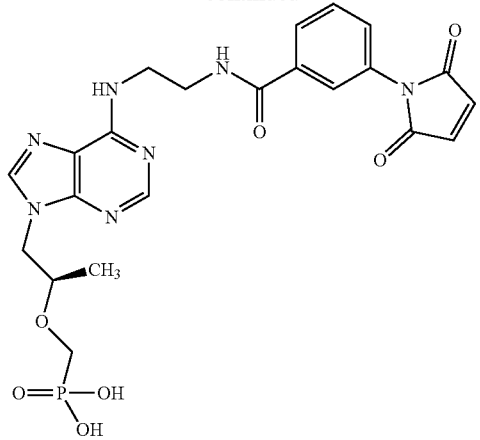
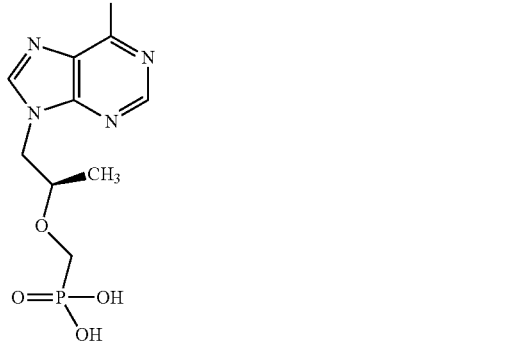
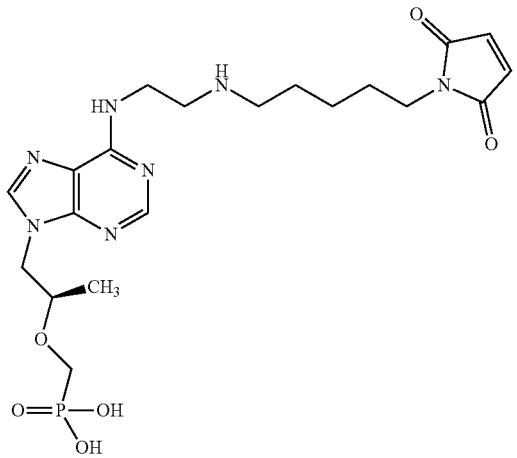
or a pharmaceutically acceptable salt thereof.
In some embodiments, the immunogens are selected from compounds having a structure according to Formula (I);
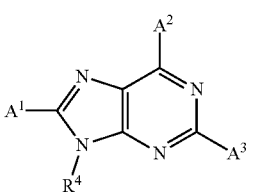

or a pharmaceutically acceptable salt thereof, wherein:
one of $A^1$, $A^2$, or $A^3$ is

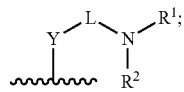

two of $A^1$, $A^2$, and $A^3$ are hydrogen or $NH_2$;
Y is a bond, $NR^3$, O, or S;
L is $C_1$-$C_{12}$-alkylene, $C_3$-$C_7$-cycloalkylene, $C_3$-$C_7$-heterocyclene, arylene, or heteroarylene, each of which can be optionally substituted by one or more substituents selected from =O, —OH, —SH, —$NO_2$, —CN, —$C_1$-$C_4$-alkyl, —$C_1$-$C_4$-haloalkyl, $C_3$-$C_7$-cycloalkyl, $C_3$-$C_7$-heterocyclyl, aryl, heteroaryl, —$OR^5$, —$NR^6R^7$, or —$C(O)X^1$;
$R^1$, $R^2$, $R^3$, and $R^4$ are each independently hydrogen, $C_1$-$C_6$-alkyl, $C_1$-$C_6$-haloalkyl, $C_3$-$C_7$-cycloalkyl, $C_3$-$C_7$-heterocyclyl, aryl, aralkyl, heteroaryl, heteroaralkyl, wherein each of $C_1$-$C_6$-alkyl, $C_1$-$C_6$-haloalkyl, $C_3$-$C_7$-cycloalkyl, $C_3$-$C_7$-heterocyclyl, aryl, aralkyl, heteroaryl, heteroaralkyl can be optionally substituted with one or more substituents selected from halogen =O, —OH, —SH, —$NO_2$, —CN, —$C_1$-$C_4$-alkyl, —$C_1$-$C_4$-haloalkyl, $C_3$-$C_7$-cycloalkyl, $C_3$-$C_7$-heterocyclyl, aryl, heteroaryl, —$OR^5$, —$NR^6R^7$, or —$C(O)X^2$;
$R^5$, $R^8$, and $R^{11}$ are each independently $C_1$-$C_6$-alkyl, aryl, aralkyl, heteroaryl, $C_0$-$C_4$-alkyl-$P(O)(OH)_2$, or —$C(O)X^4$;
$R^6$, $R^7$, $R^9$, $R^{10}$, $R^{12}$, and $R^{13}$ are each independently hydrogen, $C_1$-$C_6$-alkyl, aryl, aralkyl, heteroaryl, or —$C(O)X^5$; or
$R^6$ and $R^7$, $R^9$ and $R^{10}$, and $R^{12}$ and $R^{13}$, together with the atoms to which they are attached, independently form a 3- to 7-membered ring, which can be optionally substituted by one or more substituents selected from halogen =O, —OH, —SH, —$NO_2$, —CN, —$C_1$-$C_4$-alkyl, —$C_1$-$C_4$-haloalkyl, $C_3$-$C_7$-cycloalkyl, $C_3$-$C_7$-heterocyclyl, aryl, heteroaryl, —$OR^{11}$, —$NR^{12}R^{13}$, or —$C(O)X^6$; and
$X^1$, $X^2$, $X^3$, $X^4$, $X^5$, and $X^6$ are each, independently hydrogen, $C_1$-$C_6$-alkyl, $C_1$-$C_6$-haloalkyl, $C_2$-$C_6$-alkenyl, $C_2$-$C_6$-alkynyl, aryl, aralkyl, or heteroaryl;
wherein each of the optional substituents independently may be further substituted by one or more substituents selected from =O, —OH, —SH, —$NO_2$, —CN, —$C_1$-$C_4$-alkyl, —$C_1$-$C_4$-haloalkyl, $C_3$-$C_7$-cycloalkyl, $C_3$-$C_7$-heterocyclyl, aryl, heteroaryl, —$OR^8$, —$NR^9R^{10}$, and —$C(O)X^3$.

In some embodiments, the invention provides an immunogenic composition comprising: (a) any of the aforementioned compounds conjugated to (b) a carrier protein through a linker.

In certain embodiments of the immunogenic compositions, the linker covalently binds an active residue on the carrier protein (e.g., a cysteine or lysine) with the compound.

In certain embodiments of the immunogenic compositions, the carrier protein is selected from the group consisting of tetanus toxoid (TT), diphtheria toxoid (DT), diphtheria toxin cross-reacting material 197 (CRM197), fragment C of TT, Keyhole limpet hemocyanin (KLH), bovine serum albumin (BSA), protein D, outer-membrane protein (OMP), and pneumolysin.

In certain embodiments of the immunogenic compositions, the carrier protein is KLH.

In certain embodiments of the immunogenic compositions, the carrier protein is BSA.

In another aspect, the invention provides methods for producing antibodies, including monoclonal and polyclonal antibodies, raised against any of the aforementioned immunogenic compositions and which selectively bind to any of the aforementioned immunogenic compositions.

In another aspect, the invention provides methods or assays for monitoring adherence by a subject to an NRTI therapy (e.g., tenofovir or tenofovir derivative therapy) by detecting the presence and/or level of the NRTI or a metabolite of the NRTI (e.g., tenofovir or a tenofovir metabolite) in a biological sample from the subject. In some embodiments, the invention provides a method for performing an assay to detect an NRTI or NRTI metabolite in a fluid sample from a patient, wherein the patient has been prescribed or administered an NRTI, comprising:
(a) applying said fluid sample to a sample pad;
(b) allowing said sample to flow laterally along the sample pad to a conjugated label pad; wherein said conjugated label pad comprises a first reagent conjugated to a detectable label, and wherein a portion of the conjugated label pad and a portion of the sample pad forms a first interface;
(c) allowing said sample to flow laterally along the conjugated label pad to a membrane; wherein a portion of the membrane and a portion of the conjugated label pad forms a second interface; and wherein said membrane comprises at least one second reagent bound to the membrane to form a test line;
(d) binding the first reagent to the second reagent to form a second reagent-first reagent complex at the test line, and causing the detectable label to form a detectable signal at the test line,
(e) diagnosing the patient as non-adherent to a treatment or prophylactic regimen in the presence of a detectable signal; or adherent to a treatment or prophylactic regimen in the absence of a detectable signal.

In another aspect, the invention provides diagnostic systems and/or devices for monitoring adherence by a subject to an NRTI therapy (e.g., tenofovir or tenofovir derivative therapy) by detecting the presence and/or level of the NRTI or a metabolite of the NRTI (e.g., tenofovir or a tenofovir metabolite) in a biological sample from the subject. In some embodiments, the invention provides a device for performing an assay to detect an NRTI or NRTI metabolite in a fluid sample of a patient, wherein the patient is prescribed or administered an NRTI, comprising:
(a) a sample pad for contacting the fluid sample;
(b) a conjugated label pad, the conjugated label pad having a first reagent conjugated to a detectable label, a portion of the conjugated label pad and a portion of the sample pad forming a first interface;
(c) an assay comprising a membrane, a portion of the membrane and a portion of the conjugated label pad forming a second interface; and
(d) at least one second reagent bound to the membrane to form a test line, the first interface allowing fluid to flow from the sample pad to the conjugated label pad and contact the detectable label, the second interface allowing fluid to flow from the conjugated label pad to the membrane and to contact the at least one membrane-bound second reagent to form to a second reagent-first reagent complex, and cause the detectable label to form a detectable signal at the test line, wherein the presence of a detectable signal indicates non-adherence to a treatment or prophylactic regimen in the patient, and wherein the absence of a detectable signal indicates adherence to a treatment or prophylactic regimen in the patient.

In some embodiments, the device may have two or more separate test lines. For example, the device may have test lines corresponding to assay cutoffs at different analyte concentrations. Non-limiting examples include 10 ug/ml, 1 ug/ml, 100 ng/ml, 10 ng/ml, 1 ng/ml.

In certain embodiments of the methods or the devices, the detectable signal is modulated to provide that the presence of a detectable signal indicates adherence to a treatment or prophylactic regimen in the patient.

In certain embodiments of the method or the device, the method or device is a lateral flow assay, such as a lateral flow immunoassay.

In certain embodiments of the method or the device, the first reagent is any of the aforementioned compounds, or a conjugated derivative of the same.

In certain embodiments of the method or the device, the first reagent is a conjugated derivative of the compound:

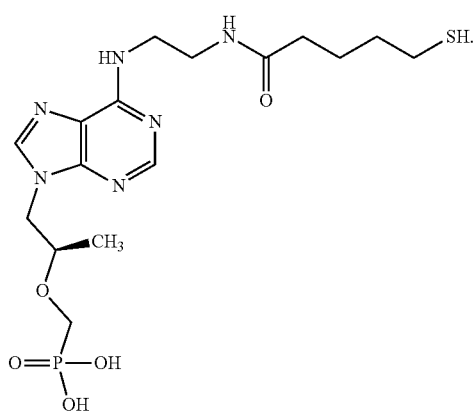 [SMILES: C[C@H](Cn1cnc2c(NCCNC(=O)CCCCS)ncnc21)OCP(=O)(O)O]

In certain embodiments of the method or the device, the first reagent is a conjugated derivative of the compound:

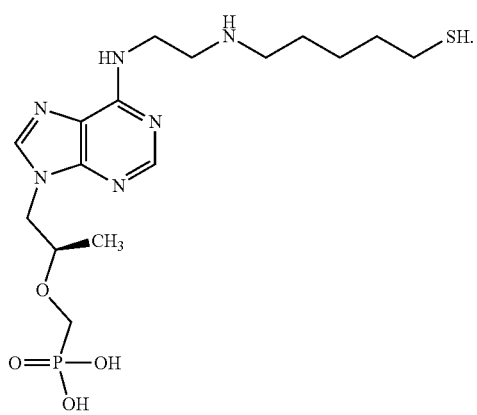 [SMILES: C[C@H](Cn1cnc2c(NCCNCCCCCS)ncnc21)OCP(=O)(O)O]

In certain embodiments of the method or the device, the first reagent is a conjugated derivative of the compound:

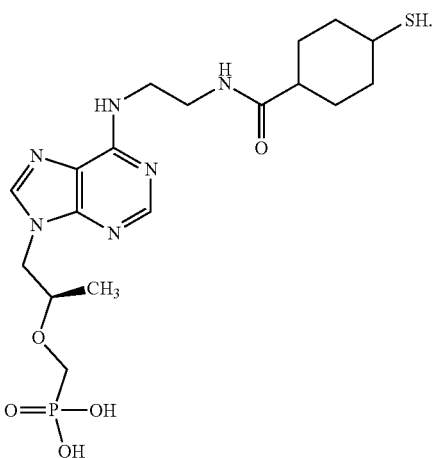 [SMILES: C[C@H](Cn1cnc2c(NCCNC(=O)C3CCC(S)CC3)ncnc21)OCP(=O)(O)O]

In certain embodiments of the method or the device, the first reagent is a conjugated derivative of the compound:

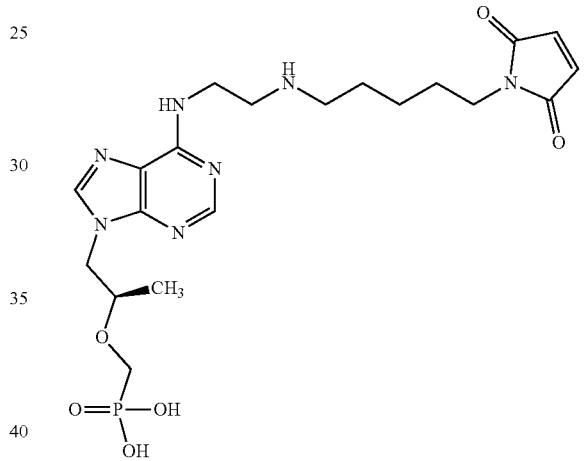

In certain embodiments of the method or the device, the first reagent is a conjugated derivative of the compound:

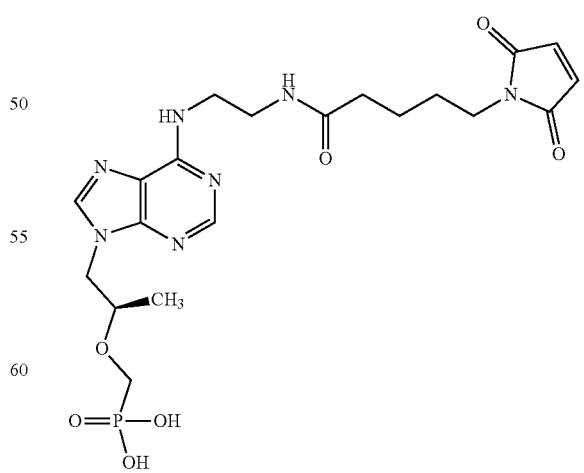

In certain embodiments of the method or the device, the first reagent is a conjugated derivative of the compound of:

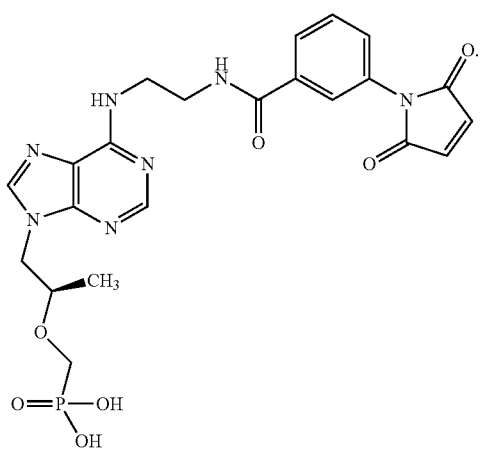 [SMILES: C[C@H](Cn1cnc2c(NCCNC(=O)c3cccc(N4C(=O)C=CC4=O)c3)ncnc21)OCP(=O)(O)O]

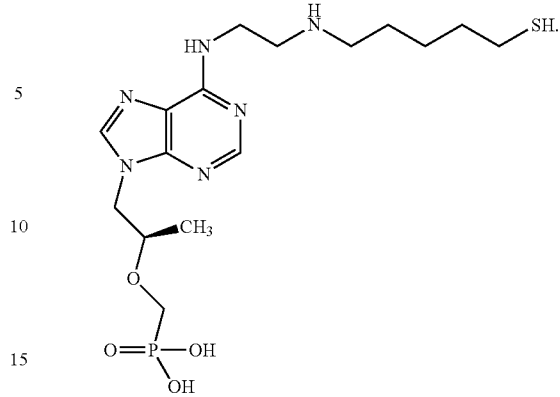

In certain embodiments of the method or the device, the second reagent is a conjugated derivative of the compound:

In certain embodiments of the method or the device, the conjugated derivative is an HRP-conjugated derivative.

In certain embodiments of the method or the device, the second reagent is any of the aforementioned antibodies. In certain embodiments, the second reagent antibody is conjugated to a detectable label.

In certain embodiments of the method or the device, the first reagent is any of the aforementioned antibodies. In certain embodiments, the first reagent antibody is conjugated to a detectable label.

In certain embodiments of the method or the device, the second reagent is any of the aforementioned compounds, or a conjugated derivative of the same.

In certain embodiments of the method or the device, the second reagent is a conjugated derivative of the compound:

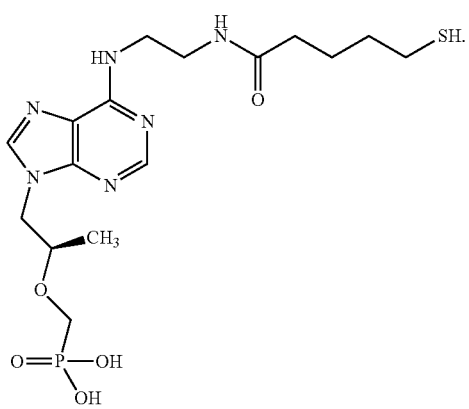 [SMILES: C[C@H](Cn1cnc2c(NCCNC(=O)CCCCS)ncnc21)OCP(=O)(O)O]

In certain embodiments of the method or the device, the second reagent is a conjugated derivative of the compound:

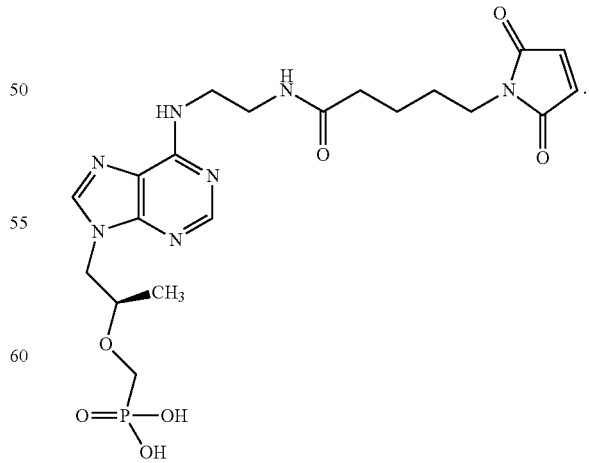

In certain embodiments of the method or the device, the second reagent is a conjugated derivative of the compound:

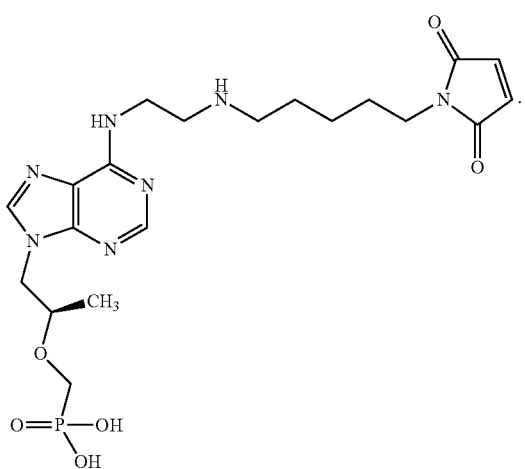 [SMILES: C[C@H](Cn1cnc2c(NCCNCCCCCN3C(=O)C=CC3=O)ncnc21)OCP(=O)(O)O]

In certain embodiments of the method or the device, the second reagent is a conjugated derivative of the compound of:

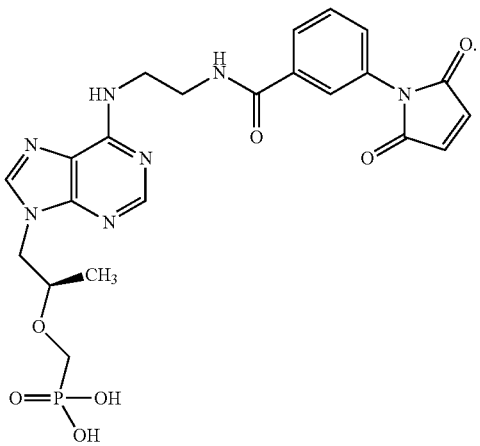 [SMILES: C[C@H](Cn1cnc2c(NCCNC(=O)c3cccc(N4C(=O)C=CC4=O)c3)ncnc21)OCP(=O)(O)O]

In certain embodiments of the method or the device, the conjugated derivative is an HRP-conjugated derivative.

In certain embodiments of the method or the device, the method or device further comprises an absorbent pad downstream of the membrane.

In certain embodiments of the method or the device, the membrane is nitrocellulose.

In certain embodiments, the device is provided in a housing.

In certain embodiments, the housing further comprises an opening for reading the detectable signal.

In certain embodiments of the method or the device, the antibody is a polyclonal antibody.

In certain embodiments of the method or the device, the antibody is a monoclonal antibody. In some embodiments, the monoclonal antibody is one or more of the monoclonal antibodies disclosed herein.

In certain embodiments of the method or the device, the metabolite is TFV.

In certain embodiments of the method or the device, the membrane further comprises a third reagent bound to the membrane downstream or upstream of the test line to form a control line.

In certain embodiments of the method or the device, the third reagent binds to the first reagent to cause a detectable signal at the control line, wherein the presence of the detectable signal at the control line indicates proper performance of the lateral-flow assay. In some embodiments, in a device with more than one test line, a control line may be provided for each test line.

In certain embodiments of the method or the device, the third reagent is an anti-HRP antibody.

In certain embodiments of the method or the device, the third regent is an anti-rabbit IgG antibody.

In certain embodiments of the method or the device, the third reagent is an anti-mouse IgG antibody.

In certain embodiments, the third reagent is an anti-goat, anti-rat, anti-sheep, anti-llama, or any other anti-IgG antibody where that IgG is not a human IgG.

In certain embodiments of the method or the device, the method or device is a point of care test.

In certain embodiments, the device is a cartridge.

In certain embodiments of the method or the device, the fluid sample is urine.

In certain embodiments of the method or the device, the prophylactic regimen is a PrEP to NRTI.

In certain embodiments of the method or the device, the NRTI is selected from the group consisting of TDF, FTC, and TAF, or derivatives thereof or combinations thereof.

In certain embodiments of the method or the device, the NRTI is TAF.

In certain embodiments of the method or the device, the NRTI is TDF.

In certain embodiments of the method or the device, the NRTI is FTC.

In certain embodiments of the method or the device, the NRTI is a combination of TDF/FTC.

In certain embodiments of the method or the device, the NRTI is a combination of TAF/FTC.

In certain embodiments of the method or the device, the NRTI is a combination of TAF/FTC/TAF.

In certain embodiments of the method or the device, the NRTI is a combination of TAF, FTC, TAF and any other NRTI.

In another aspect, the invention provides a kit, comprising:
(a) a sample collection receptacle for receiving a biological sample; and
(b) a device of the invention for assaying the biological sample.

In certain embodiments, the kit further comprises instructions for use.

In certain embodiments, the kit further comprises a hand held device.

In some embodiments, the kit further comprises a dropper to provide a means to place a sample on the strip. In some embodiments, the strip serves as a dipstick. In some embodiments, the strip may be in a plastic cassette.

In certain embodiments, an electronic signal reader is adapted to receive any of the aforementioned devices and measure or detect a reflectance or spectrophotometric signal caused by the presence or absence of the metabolite.

In certain embodiments, the reader is a reflectance reader.

In certain embodiments, the biological sample is urine.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

Figure 1:
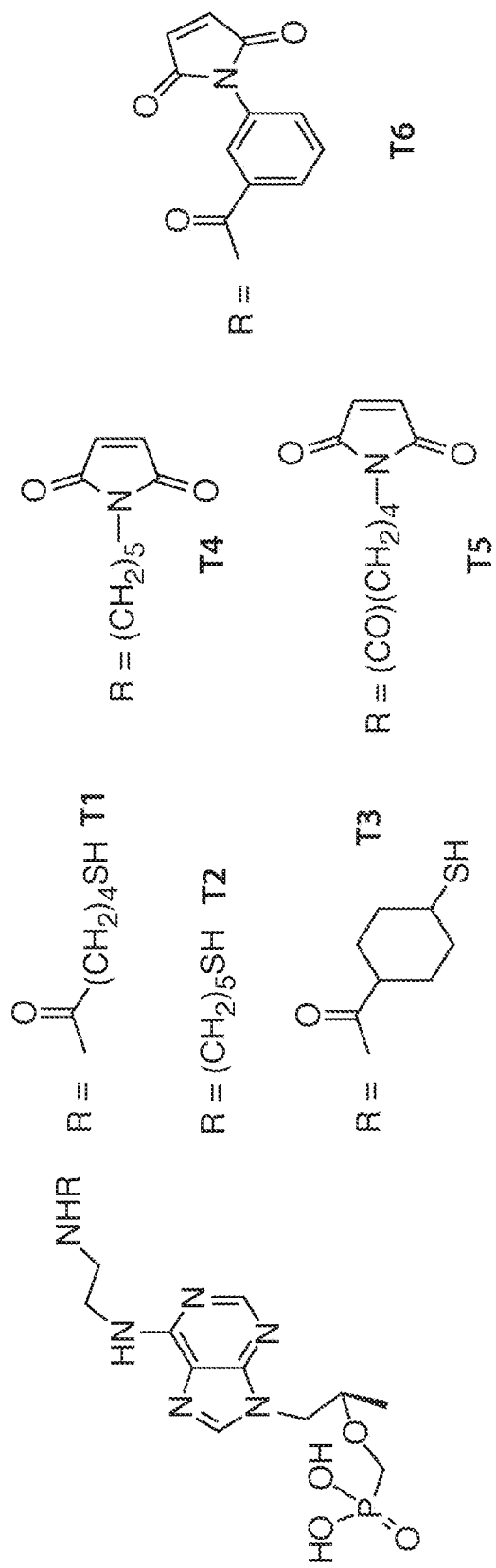
FIG. 1 shows tenofovir derivatives useful for developing antibodies for a POC assay for PrEP and ART that may be used to detect TDF and/or TAF and/or TFV. Side chains T1-T6, among others, are synthesized on the base molecule (left).

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

DETAILED DESCRIPTION

General Definitions

All scientific and technical terms used herein, unless otherwise defined below, are intended to have the same meaning as commonly understood by one of ordinary skill in the art to which this invention belongs. In the case of any conflict, the present specification, including definitions, will control. References to techniques employed herein are intended to refer to the techniques as commonly understood in the art, including variations on those techniques or substitutions of equivalent or later-developed techniques which would be apparent to one of skill in the art. In order to more clearly and concisely describe the subject matter which is the invention, the following definitions are provided for certain terms which are used in the specification and appended claims.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or in some instances ±10%, or in some instances ±5%, or in some instances ±1%, or in some instances ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

The term "antibody," as used herein, refers to an immunoglobulin molecule which specifically binds with an antigen (e.g., metabolite, metabolite derivative, or conjugate of same). Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426). Generally, an intact or full-length antibody comprises two heavy chains and two light chains. Each heavy chain contains a heavy chain variable region (VH) and a first, second and third constant regions (CH1, CH2 and CH3). Each light chain contains a light chain variable region (VL) and a constant region (CL). An "antibody heavy chain," as used herein, refers to the larger of the two types of polypeptide chains present in all mammalian antibody molecules in their naturally occurring conformations. An "antibody light chain," as used herein, refers to the smaller of the two types of polypeptide chains present in all mammalian antibody molecules in their naturally occurring conformations. κ and λ light chains refer to the two major antibody light chain isotypes. Depending on the amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known. For purposes of the present invention, the antibodies need not be of any particular class or any particular species of origin. The term "antibody" as encompasses a "synthetic antibody" as used herein.

By the term "synthetic antibody" as used herein, is meant an antibody which is generated using recombinant DNA technology, such as, for example, an antibody expressed by a bacteriophage. The term should also be construed to mean any antibody which has been generated by the synthesis of a DNA molecule encoding the antibody and expression of the recombinant DNA to produce the antibody protein using synthetic DNA or amino acid sequence technology which is available and well known in the art.

By the term "specifically binds," as used herein with respect to an antibody (e.g., anti-NRTI derivative conjugate antibody such as an anti-TFV antibody), is meant an antibody which recognizes a specific small molecule (e.g., metabolite, NRTI, or any of the compounds described herein, or derivatives or conjugates of same), but does not substantially recognize or bind other molecules in a sample. For example, an antibody that specifically binds to one small molecule (e.g., metabolite, NRTI, or any of the compounds described herein, or derivatives or conjugates of same) may also bind to another small molecule (e.g., metabolite, NRTI, or any of the compounds described herein, or derivatives or conjugates of same). But, such cross-species reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific small molecule (e.g., metabolite, NRTI, or any of the compounds described herein, or derivatives or conjugates of same). If an antibody is specific for a metabolite (e.g., NRTI), then the presence of the metabolite (e.g., NRTI) in a reaction containing labeled NRTI derivative and the antibody, will reduce the amount of labeled NRTI derivative bound to the antibody.

By the term "applicator," as the term is used herein, is meant any device including, but not limited to, a hypodermic syringe, a pipette, an iontophoresis device, a patch, and the like, for administering the compositions of the invention to a subject.

As used herein, "metabolite" or "NRTI" in the context of the present invention encompasses, without limitation, small molecules (e.g., NRTI or any of the compounds described herein, and derivatives or conjugates of same), together with degradation products, protein-ligand complexes, elements, related metabolites, and other small molecule or sample-derived measures.

The terms "metabolite related to NRTI" and "NRTI" are used interchangeably herein. Therefore it should be understood that a reference to "NRTI" should be read as relating to any metabolite specifically associated with an "NRTI". As a non-limiting example, Tenofovir (TFV) is an active metabolite related to the NRTI Tenofovir Disoproxil Fumarate (TDF) and Tenofovir Alafenamide (TAF).

The terms "NRTI derivative" or "NRTI analog" are used interchangeably to describe derivatives of the compound of Formula I, Formula II, and Formula III. In certain embodiments, the NRTI derivative or NRTI analog is a "TFV derivative" or a "TFV analog". In certain embodiments, the NRTI derivative or NRTI analog is a "TAF derivative" or a "TAF analog". In certain embodiments, the NRTI derivative or NRTI analog is a "FTC derivative" or a "FTC analog". In certain embodiments, the NRTI derivative or NRTI analog is a "TDF derivative" or a "TDF analog".

As used herein, the term "tenofovir" and abbreviation "TFV" refer to the composition:

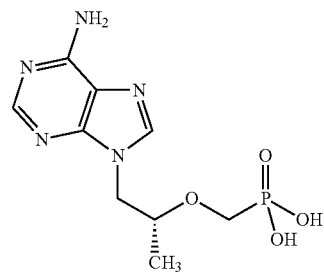 [SMILES: C[C@H](Cn1cnc2c(N)ncnc21)OCP(=O)(O)O]

As used herein, the term "tenofovir disoproxil" and abbreviation "TD" refer to the composition:

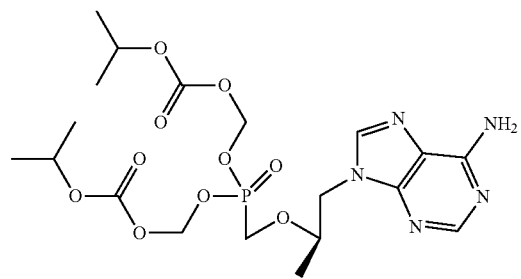 [SMILES: CC(C)OC(=O)OCOP(=O)(CO[C@H](C)Cn1cnc2c(N)ncnc21)OCOC(=O)OC(C)C]

As used herein, the term "tenofovir disoproxil fumarate" and abbreviation "TDF" refer to the composition:

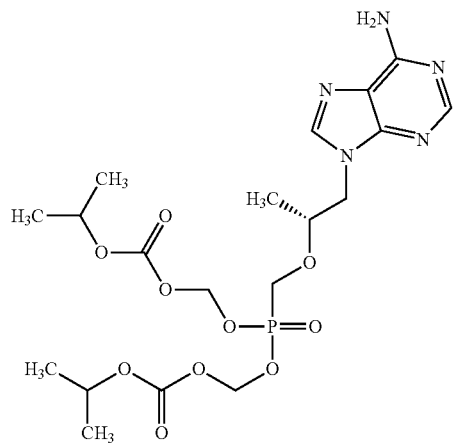

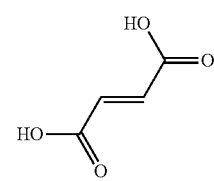

As used herein, the term "tenofovir alafenamide" and abbreviation "TA" refer to the composition:

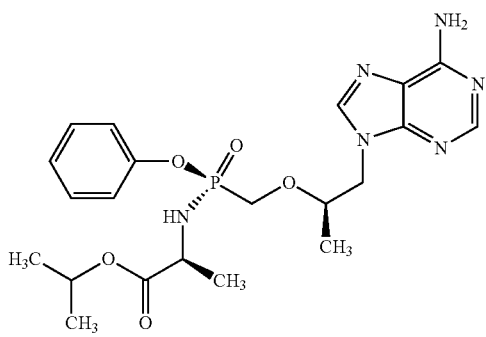 [SMILES: CC(C)OC(=O)[C@H](C)N[P@](=O)(CO[C@H](C)Cn1cnc2c(N)ncnc21)Oc1ccccc1]

As used herein, the term "tenofovir alafenamide fumarate" and abbreviation "TAF" refer to the composition:

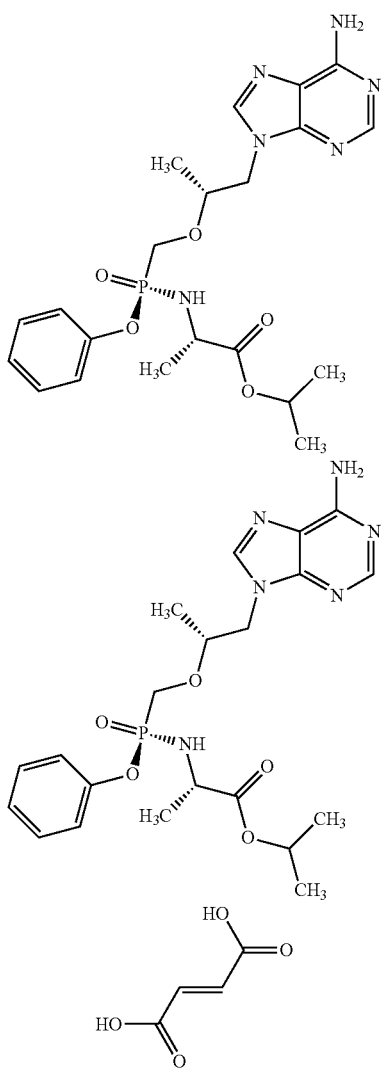

As used herein, the term "emtricitabine" and abbreviation "FTC" refer to the composition:

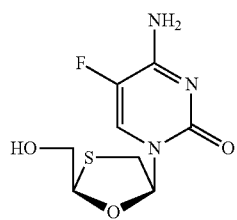 [SMILES: Nc1nc(=O)n([C@@H]2CS[C@H](CO)O2)cc1F]

The terms "NRTI-derivative conjugate" or "NRTI-analog conjugate" are used interchangeably to describe NRTI derivatives conjugated to carrier proteins (such as KLH, BSA, etc.) for generating immunogenic compositions described herein. In certain embodiments, the NRTI-derivative conjugate is a "TFV-derivative conjugate". In certain embodiments, the NRTI-derivative conjugate is a "TAF-derivative conjugate". In certain embodiments, the NRTI-derivative conjugate is a "TDF-derivative conjugate". In certain embodiments, the NRTI-derivative conjugate is a "FTC-derivative conjugate". In certain embodiments, the "NRTI-derivative conjugate" describes an "HRP-NRTI derivative" which comprises an NRTI derivative conjugated to HRP for use in any of the immunoassays described herein.

The terms "anti-NRTI-derivative conjugate antibody" or "anti-NRTI-analog conjugate antibody" refers to antibodies (e.g., polyclonal, monoclonal, etc.) raised against a NRTI-derivative conjugate. Such "anti-NRTI-derivative conjugate antibody" may specifically bind with high specificity to the NRTI-derivative, and/or conjugate of same. In certain embodiments, the "anti-NRTI-derivative conjugate antibody" is an "anti-TFV-derivative conjugate antibody" (or "anti-TFV antibody" in short form). In certain embodiments, the "anti-NRTI-derivative conjugate antibody" is an "anti-TAF-derivative conjugate antibody" (or "anti-TAF antibody" in short form). In certain embodiments, the "anti-NRTI-derivative conjugate antibody" is an "anti-TDF-derivative conjugate antibody" (or "anti-TAF antibody" in short form). In certain embodiments, the "anti-NRTI-derivative conjugate antibody" is an "anti-FTC-derivative conjugate antibody" (or "anti-FTC antibody" in short form).

As used herein, a "biosensor" is an analytical device for the detection of a small molecule (such as the metabolite, NRTI, or any of the compounds described herein) in a sample. Biosensors can comprise a recognition element, which can recognize or capture a specific small molecule (such as the metabolite, NRTI, or any of the compounds described herein), and a transducer, which transmits the presence or absence of a small molecule (such as the metabolite, NRTI, or any of the compounds described herein) into a detectable signal.

As used herein, the term "data" in relation to one or more metabolites, or the term "metabolite data" generally refers to data reflective of the absolute and/or relative abundance (level) of a product of a metabolite in a sample. As used herein, the term "dataset" in relation to one or more metabolites refers to a set of data representing levels of each of one or more metabolite products of a panel of metabolites in a reference population of subjects. A dataset can be used to generate a formula/classifier of the invention. According to one embodiment, the dataset need not comprise data for each metabolite product of the panel for each individual of the reference population. For example, the "dataset" when used in the context of a dataset to be applied to a formula can refer to data representing levels of each metabolite for each individual in one or more populations, but as would be understood can also refer to data representing levels of each metabolite for 99%, 95%, 90%, 85%, 80%, 75%, 70% or less of the individuals in each of said one or more populations and can still be useful for purposes of applying to a formula.

The term "control" or "reference standard" describes a material comprising none, or a normal, low, or high level of one of more of the small molecules (e.g., metabolite, NRTI, or any of the compounds describe herein, or conjugates or derivatives of same) of the invention, such that the control or reference standard may serve as a comparator against which a sample can be compared.

As used herein, the term "detection reagent" refers to an agent comprising an affinity moiety that specifically binds to a small molecule (e.g., metabolite, NRTI, or any of the compounds described herein) or other targeted molecule to be detected in a sample. Detection reagents may include, for example, a detectable moiety, such as a radioisotope, a fluorescent label, a magnetic label, and enzyme, or a chemical moiety such as biotin or digoxigenin. The detectable moiety can be detected directly, or indirectly, by the use of a labeled specific binding partner of the detectable moiety. Alternatively, the specific binding partner of the detectable moiety can be coupled to an enzymatic system that produces a detectable product.

As used herein, a "detector molecule" is a molecule that may be used to detect a compound of interest. Non-limiting examples of a detector molecule are molecules that bind specifically to a compound of interest, such as, but not limited to, an antibody, a cognate receptor, and a small molecule.

By the phrase "determining the level of small molecule (e.g., metabolite, NRTI, or any of the compounds describe herein, or conjugates or derivatives of same) concentration" is meant an assessment of the amount of a small molecule (e.g., metabolite, NRTI, or any of the compounds describe herein, or conjugates or derivatives of same) in a sample using technology available to the skilled artisan to detect a sufficient portion of any small molecule (e.g., metabolite, NRTI, or any of the compounds describe herein, or conjugates or derivatives of same).

A "disease" is a state of health of an animal wherein the animal cannot maintain homeostasis, and wherein if the disease is not ameliorated then the animal's health continues to deteriorate.

As used herein, an "immunoassay" refers to a biochemical test that measures the presence or concentration of a substance in a sample, such as a biological sample, using the reaction of an antibody to its cognate antigen, for example the specific binding of an antibody to a small molecule (e.g., NRTI, any of the compounds described herein, or derivatives, conjugates, and analogs thereof). Both the presence of the small molecule (e.g., NRTI, any of the compounds described herein, or derivatives, conjugates, and analogs thereof) or the amount of the small molecule (e.g., NRTI, any of the compounds described herein, or derivatives, conjugates, and analogs thereof) present can be measured.

As used herein, an "instructional material" includes a publication, a recording, a diagram, or any other medium of expression which can be used to communicate the usefulness of a component of the invention in a kit for detecting metabolites disclosed herein. The instructional material of the kit of the invention can, for example, be affixed to a container which contains the component of the invention or be shipped together with a container which contains the component. Alternatively, the instructional material can be shipped separately from the container with the intention that the instructional material and the component be used cooperatively by the recipient.

The term "label" when used herein refers to a detectable compound or composition that is conjugated directly or indirectly to a probe to generate a "labeled" probe. The label may be detectable by itself (e.g., radioisotope labels or fluorescent labels) or, in the case of an enzymatic label, may catalyze chemical alteration of a substrate compound or composition that is detectable (e.g., avidin-biotin). In some instances, primers can be labeled to detect a PCR product. In some embodiments, the label is HRP.

The "level" of one or more metabolites means the absolute or relative amount or concentration of the metabolite in the sample.

"Measuring" or "measurement," or alternatively "detecting" or "detection," means assessing the presence, absence, quantity or amount (which can be an effective amount) of either a given substance within a clinical or subject-derived sample, including the derivation of qualitative or quantitative concentration levels of such substances, or otherwise evaluating the values or categorization of a subject's clinical parameters.

As used herein, the term "monitoring adherence" refers to determining compliance of a patient with a prescribed course of treatment. Adherence encompasses compliance with aspects including dosage amounts and frequencies of a prescribed course of treatment.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

"Polypeptide," as used herein refers to a polymer in which the monomers are amino acid residues which are joined together through amide bonds. When the amino acids are alpha-amino acids, either the L-optical isomer or the D-optical isomer can be used, the L-isomers being preferred. The terms "polypeptide" or "protein" or "peptide" as used herein are intended to encompass any amino acid sequence and include modified sequences. The term "polypeptide" or "protein" or "peptide" is specifically intended to cover naturally occurring proteins, as well as those which are recombinantly or synthetically produced. It should be noted that the term "polypeptide" or "protein" includes naturally occurring modified forms of the proteins or glycosylate forms.

As used herein, the term "providing a prognosis" refers to providing a prediction of the probable course and outcome of a disease, disorder or condition, including prediction of severity, duration, chances of recovery, etc. The methods can also be used to devise a suitable therapeutic plan, e.g., by indicating whether or not the condition is still at an early stage or if the condition has advanced to a stage where aggressive therapy would be ineffective.

A "reference level" of a metabolite means a level of the metabolite that is indicative of a therapeutic level of the drug.

The term "risk" according to the invention, comprises finding a particular patient who is not currently diagnosed with HIV may become exposed to bodily fluid from an individual currently diagnosed with HIV or otherwise become exposed to HIV.

"Sample", "specimen" or "biological sample" as used herein means a biological material isolated from an individual. The biological sample may contain any biological material suitable for detecting the desired metabolites, and may comprise cellular and/or non-cellular material obtained from the individual.

The term "solid support," "support," and "substrate" as used herein are used interchangeably and refer to a material or group of materials having a rigid or semi-rigid surface or surfaces. In one embodiment, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. See U.S. Pat. No. 5,744,305 for exemplary substrates.

The "therapeutic concentration" or "therapeutic level" is the concentration of a substance at which therapeutic benefits are gained. For the NRTIs of the invention, for example those illustrated in the Examples, the therapeutic concentration is about 1,000 ng/mL or more. The invention could be applied to other NRTIs and designed to address the appropriate therapeutic threshold that may be more or less than 1,000 ng/mL, as appropriate for that drug.

The term "treatment regimen" or "medical regimen" as used herein relates to at least the frequency and dosage of any pharmaceutical agent being taken by an individual for treatment or prevention of a disease or condition.

Chemical Definitions

The term "pharmaceutically acceptable salts" refers to inorganic and organic acid addition salts of the compounds of the invention. These salts can be prepared in situ during the final isolation and purification of the compound(s), or by separately reacting the purified compound(s) in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts, and the like. See, for example, Berge et al. (1977), "Pharmaceutical Salts", *J. Pharm. Sci.* 66:1-19.

In other cases, the compounds useful in the methods of the present invention may contain one or more acidic functional groups and, thus, are capable of forming pharmaceutically acceptable salts with pharmaceutically acceptable bases. The term "pharmaceutically acceptable salts" in these instances refers to the inorganic and organic base addition salts of a compound of the invention. These salts can likewise be prepared in situ during the final isolation and purification of the compound(s), or by separately reacting the purified compound(s) in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, e.g., Berge et al., supra).

One skilled in the art may make chemical modifications to the desired compound in order to make reactions of that compound more convenient for purposes of preparing conjugates of the invention.

Certain compounds of the present invention may exist in particular geometric or stereoisomeric forms. The present invention contemplates all such compounds, including cis- and trans-isomers, R- and S-enantiomers, diastereomers, (d)-isomers, (l)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis or by derivation with a chiral auxiliary, where the resulting diastereomeric mixture is separated and the auxiliary group cleaved to provide the pure desired enantiomer. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomer.

"Alkyl" refers to a fully saturated cyclic or acyclic, branched or unbranched carbon chain moiety having the number of carbon atoms specified, or up to 30 carbon atoms if no specification is made. For example, alkyl of 1 to 8 carbon atoms refers to moieties such as methyl, ethyl, propyl, butyl, pentyl, hexyl, heptyl, and octyl, and those moieties that are positional isomers of these moieties. Alkyl of 10 to 30 carbon atoms includes decyl, undecyl, dodecyl, tridecyl, tetradecyl, pentadecyl, hexadecyl, heptadecyl, octadecyl, nonadecyl, eicosyl, heneicosyl, docosyl, tricosyl and tetracosyl. In certain embodiments, a straight chain or branched chain alkyl has 30 or fewer carbon atoms in its backbone (e.g., $C_1$-$C_{30}$ for straight chains, $C_3$-$C_{30}$ for branched chains), and more preferably 20 or fewer.

"Cycloalkyl" means mono- or bicyclic or bridged saturated carbocyclic rings, each having from 3 to 12 carbon atoms. Likewise, preferred cycloalkyls have from 5-12 carbon atoms in their ring structure, and more preferably have 6-10 carbons in the ring structure.

Unless the number of carbons is otherwise specified, "lower alkyl," as used herein, means an alkyl group, as defined above, but having from one to ten carbons, more preferably from one to six carbon atoms in its backbone structure such as methyl, ethyl, n-propyl, isopropyl, n-butyl, isobutyl, sec-butyl, and tert-butyl. Likewise, "lower alkenyl" and "lower alkynyl" have similar chain lengths. Throughout the application, preferred alkyl groups are lower alkyls. In certain embodiments, a substituent designated herein as alkyl is a lower alkyl.

The term "aryl" as used herein includes 3- to 12-membered substituted or unsubstituted single-ring aromatic groups in which each atom of the ring is carbon (i.e., carbocyclic aryl) or where one or more atoms are heteroatoms (i.e., heteroaryl). Preferably, aryl groups include 5- to 12-membered rings, more preferably 6- to 10-membered rings. In certain embodiments, aryl includes ($C_6$-$C_{10}$)aryl. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Carbocyclic aryl groups include benzene, naphthalene, phenanthrene, phenol, aniline, and the like. Heteroaryl groups include substituted or unsubstituted aromatic 3- to 12-membered ring structures, more preferably 5- to 12-membered rings, more preferably 6- to 10-membered rings, whose ring structures include one to four heteroatoms. In certain embodiments, heteroaryl includes ($C_2$-$C_9$)heteroaryl. Heteroaryl groups include, for example, pyrrole, furan, thiophene, imidazole, oxazole, thiazole, triazole, pyrazole, pyridine, pyrazine, pyridazine and pyrimidine, and the like.

The term "aralkyl" is art-recognized and refers to an alkyl group substituted with an aryl group.

The term "heteroatom" is art-recognized and refers to an atom of any element other than carbon or hydrogen. Illustrative heteroatoms include boron, nitrogen, oxygen, phosphorus, sulfur and selenium.

The terms "heterocyclyl" or "heterocyclic group" refer to 3- to 12-membered ring structures, more preferably 5- to 12-membered rings, more preferably 6- to 10-membered rings, whose ring structures include one to four heteroatoms. Heterocycles can also be polycycles. In certain embodiments, heterocyclyl includes ($C_2$-$C_9$)heterocyclyl. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, sulfamoyl, sulfinyl, ether, alkylthio, sulfonyl, ketone, aldehyde, ester, a heterocyclyl, an aromatic or heteroaromatic moiety, —$CF_3$, —CN, and the like. The term "heteroaryl" includes substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "halogen" designates —F, —Cl, —Br, or —I.

The term "haloalkyl" means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

As used herein, the definition of each expression, e.g., alkyl, m, n, etc., when it occurs more than once in any structure, is intended to be independent of its definition elsewhere in the same structure.

Principles of the Invention

The present invention depends, in part, upon the development of new products and methods for rapidly testing adherence to PreP therapy in a clinical setting, other POC, or home. The methods involve the use of new antibodies developed against tenofovir using new tenofovir derivatives as immunogens. These antibodies can be employed in immunodiagnostic assays, including lateral flow immunodiagnostic assays, to detect the presence of tenofovir in patient samples, including urine samples.

More generally, the present invention relates to reagents (including but not limited to antibodies and immunogens) and methods for conveniently monitoring the presence or absence of NRTI in a biological fluid sample. Such reagents can be used with any of the systems, devices, kits, and methods as described in WO201714786A1 (PCT/US17/018945) (incorporated herein by reference in its entirety).

In some embodiments, the invention can be used to assess the level of adherence to a prescribed treatment plan for a patient prescribed an NRTI. In some embodiments, the invention can be used to assess the NRTI level in a biological fluid sample from an individual who has previously taken an NRTI before an episode wherein the individual is at risk of contracting HIV. Preferably, the sample is urine and the NRTI in a patient's urine is an indicator that the patient has taken a prescribed NRTI. In some embodiments, the sample is whole blood, plasma, serum, or saliva. Accordingly, the method of the invention provides new reagents (e.g., NRTI derivatives, and conjugates and antibodies of same) for monitoring adherence and response to a particular treatment.

Using the new reagents, the invention provides methods and systems for detecting an NRTI in urine wherein the system also includes a control in order to ensure that the test sample is indeed urine. The NRTI and the control for urine may be identified by any suitable assay. A suitable assay may include one or more of an enzyme assay, an immunoassay, mass spectrometry, chromatography, electrophoresis, a biosensor, an antibody microarray, or any combination thereof. If an immunoassay is used it may be an enzyme-linked immunosorbent immunoassay (ELISA), a competitive assay, a radioimmunoassay (RIA), a lateral flow immunoassay, a Western Blot, an immunoassay using a biosensor, an immunoprecipitation assay, an agglutination assay, a turbidity assay or a nephelometric assay. A preferred method is an immunoassay that utilizes a rapid immunoassay platform such as lateral flow.

Accordingly, the invention includes any platform for detecting a NRTI in a biological sample such as urine. In one embodiment, the system provides a convenient POC device which can quickly detect the presence or absence of a NRTI in an at home or clinical setting. One non-limiting example of a point of care device is a lateral flow immunoassay.

NRTI-Derivative Immunogens

In one aspect, the invention provides for the production of antibodies or binding partners with high specificity to the NRTI or NRTI metabolite of interest, or conjugates of same, for utilization in the immunoassay. The antibody should have high specificity to the target NRTI or NRTI metabolite to permit the design of an immunoassay that allows monitoring of compliance of drug dosing. The production of the antibody requires the synthesis of a derivative (e.g., NRTI derivative conjugates such as TFV derivative conjugates) that can be utilized to immunize animals. The derivative is designed in a manner to maximize the recognition of the target molecule with minimal cross reactivity to other substances that may be present in the sample. The derivative is linked to a carrier protein to enhance the immune recognition and allow the production of antibodies.

Thus, in some embodiments, the invention provides NRTI-derivatives immunogens comprising compounds having the structure according to Formula (I):

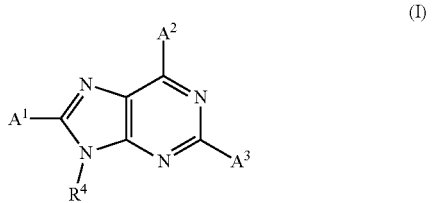

(I)

or a pharmaceutically acceptable salt thereof, wherein:
one of $A^1$, $A^2$, or $A^3$ is

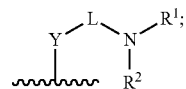

two of $A^1$, $A^2$, and $A^3$ are hydrogen or $NH_2$;
Y is a bond, $NR^3$, O, or S;
L is $C_1$-$C_{12}$-alkylene, $C_3$-$C_7$-cycloalkylene, $C_3$-$C_7$-heterocyclene, arylene, or heteroarylene, each of which can be optionally substituted by one or more substituents selected from =O, —OH, —SH, —NO$_2$, —CN, —C$_1$-C$_4$-alkyl, —C$_1$-C$_4$-haloalkyl, C$_3$-C$_7$-cycloalkyl, C$_3$-C$_7$-heterocyclyl, aryl, heteroaryl, —OR$^5$, —NR$^6$R$^7$, or —C(O)X$^1$;
$R^1$, $R^2$, $R^3$, and $R^4$ are each independently hydrogen, $C_1$-$C_6$-alkyl, $C_1$-$C_6$-haloalkyl, $C_3$-$C_7$-cycloalkyl, $C_3$-$C_7$-heterocyclyl, aryl, aralkyl, heteroaryl, heteroaralkyl, wherein each of $C_1$-$C_6$-alkyl, $C_1$-$C_6$-haloalkyl, $C_3$-$C_7$-cycloalkyl, $C_3$-$C_7$-heterocyclyl, aryl, aralkyl, heteroaryl, heteroaralkyl can be optionally substituted with one or more substituents selected from halogen =O, —OH, —SH, —NO$_2$, —CN, —C$_1$-C$_4$-alkyl, —C$_1$-C$_4$-haloalkyl, C$_3$-C$_7$-cycloalkyl, C$_3$-C$_7$-heterocyclyl, aryl, heteroaryl, —OR$^5$, —NR$^6$R$^7$, or —C(O)X$^2$;
$R^5$, $R^8$, and $R^{11}$ are each independently $C_1$-$C_6$-alkyl, aryl, aralkyl, heteroaryl, $C_0$-$C_4$-alkyl-P(O)(OH)$_2$, or —C(O)X$^4$;

$R^6$, $R^7$, $R^9$, $R^{10}$, $R^{12}$, and $R^{13}$ are each independently hydrogen, $C_1$-$C_6$-alkyl, aryl, aralkyl, heteroaryl, or —C(O)X$^5$; or
$R^6$ and $R^7$, $R^9$ and $R^{10}$, and $R^{12}$ and $R^{13}$, together with the atoms to which they are attached, independently form a 3- to 7-membered ring, which can be optionally substituted by one or more substituents selected from halogen =O, —OH, —SH, —NO$_2$, —CN, —C$_1$-C$_4$-alkyl, —C$_1$-C$_4$-haloalkyl, C$_3$-C$_7$-cycloalkyl, C$_3$-C$_7$-heterocyclyl, aryl, heteroaryl, —OR$^{11}$, —NR$^{12}$R$^{13}$, or —C(O)X$^6$; and
$X^1$, $X^2$, $X^3$, $X^4$, $X^5$, and $X^6$ are each, independently hydrogen, $C_1$-$C_6$-alkyl, $C_1$-$C_6$-haloalkyl, $C_2$-$C_6$-alkenyl, $C_2$-$C_6$-alkynyl, aryl, aralkyl, or heteroaryl;
wherein each of the optional substituents independently may be further substituted by one or more substituents selected from =O, —OH, —SH, —NO$_2$, —CN, —C$_1$-C$_4$-alkyl, —C$_1$-C$_4$-haloalkyl, C$_3$-C$_7$-cycloalkyl, C$_3$-C$_7$-heterocyclyl, aryl, heteroaryl, —OR$^8$, —NR$^9$R$^{10}$, and —C(O)X$^3$.

In some embodiments, the compound of Formula (I) has a structure according to Formula (II):

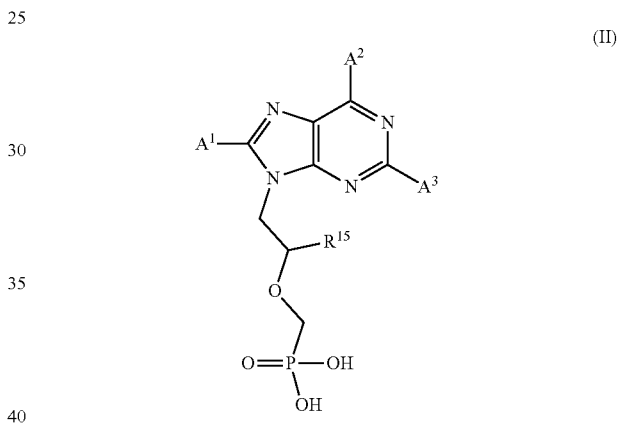

(II)

or a pharmaceutically acceptable salt thereof, wherein $R^{15}$ is $C_1$-$C_4$-alkyl. Preferably, $R^{15}$ is methyl.

In some embodiments, the compound of Formula (I) or (II) has a structure according to Formula (IIa):

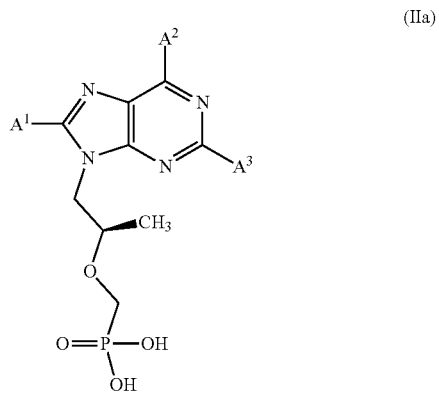

(IIa)

or a pharmaceutically acceptable salt thereof.

In some embodiments, the compound of Formula (I), (II), or (IIa) has a structure according to Formula (III):

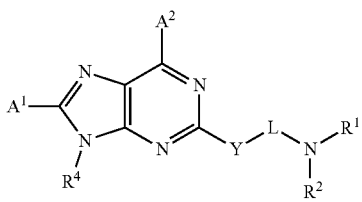
(III)

or a pharmaceutically acceptable salt thereof. Preferably, $A^1$ and $A^2$ are hydrogen.

In some embodiments, the compound of Formula (I), (II), or (IIa) has a structure according to Formula (IV):

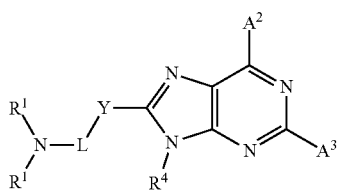
(IV)

or a pharmaceutically acceptable salt thereof. Preferably, $A^2$ and $A^3$ are hydrogen In some embodiments, the compound of Formula (I), (II), or (IIa) has a structure according to Formula (V):

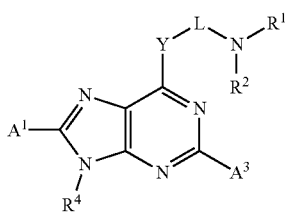
(V)

or a pharmaceutically acceptable salt thereof. Preferably, $A^1$ and $A^3$ are hydrogen.

In some embodiments, provided herein is a compound of Formula (I), (II), (IIa), (III), (IV), or (V), or a pharmaceutically acceptable salt thereof, wherein Y is $NR^3$. Preferably, $R^3$ is hydrogen.

In other embodiments, provided herein is a compound of Formula (I), (II), (IIa), (III), (IV), or (V), or a pharmaceutically acceptable salt thereof, wherein L is $(CH_2)_n$, wherein n is 1 to 6. Preferably, n is 2.

In certain embodiments, provided herein is a compound of Formula (I), (II), (IIa), (III), (IV), or (V), or a pharmaceutically acceptable salt thereof, wherein $R^1$ is $C_1$-$C_6$-alkyl optionally substituted with one or more substituents selected from halogen =O, —OH, —SH, $C_3$-$C_7$-cycloalkyl, $C_3$-$C_7$-heterocyclyl, aryl, and heteroaryl. In some such embodiments, each of the optional substituents independently may be further substituted by one or more substituents selected from —OH, —SH, —$C_1$-$C_4$-alkyl, $C_3$-$C_7$-cycloalkyl, $C_3$-$C_7$-heterocyclyl, aryl, and heteroaryl.

In certain other embodiments, provided herein is a compound of Formula (I), (II), (IIa), (III), (IV), or (V), or a pharmaceutically acceptable salt thereof, wherein $R^1$ is

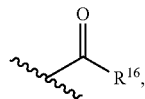

wherein $R^{16}$ is $C_1$-$C_6$-alkyl, $C_3$-$C_7$-cycloalkyl, or aryl, each of which may be optionally substituted by —SH, $C_3$-$C_7$-cycloalkyl, $C_3$-$C_7$-heterocyclyl, aryl, or heteroaryl. In some such embodiments, $R^1$ is

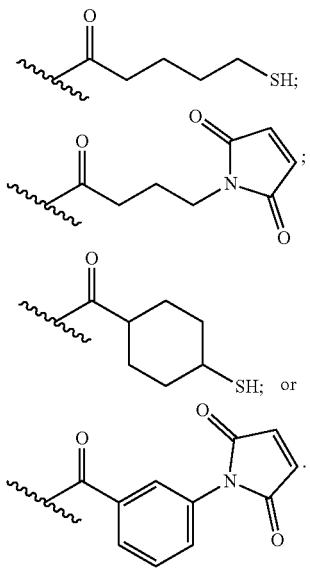

In alternative embodiments, provided herein is a compound of Formula (I), (II), (IIa), (III), (IV), or (V), or a pharmaceutically acceptable salt thereof, wherein $R^1$ is

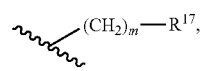

wherein m is 1 to 6; and $R^{17}$ is $C_3$-$C_7$-cycloalkyl, $C_3$-$C_7$-heterocyclyl, aryl, or heteroaryl. In some such embodiments, $R^1$ is

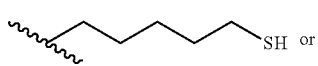

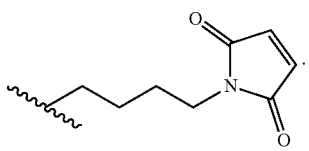

In particular embodiments, the NRTI is a tenofovir derivative and the immunogen comprises a compound is selected from:

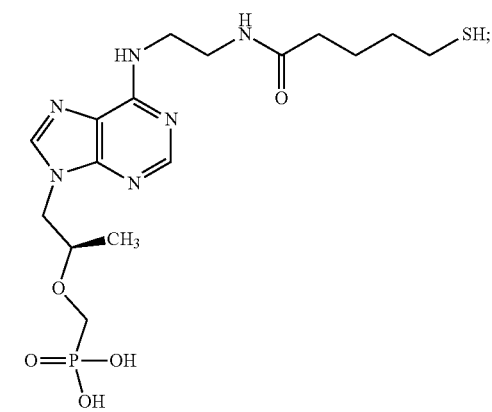

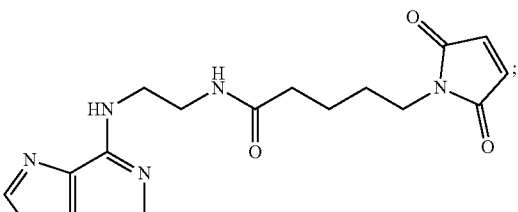

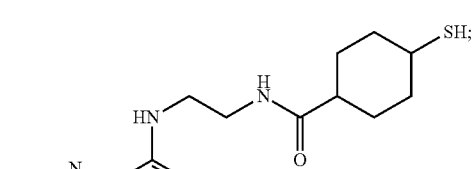

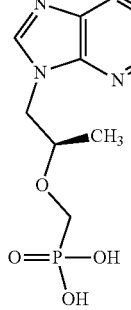

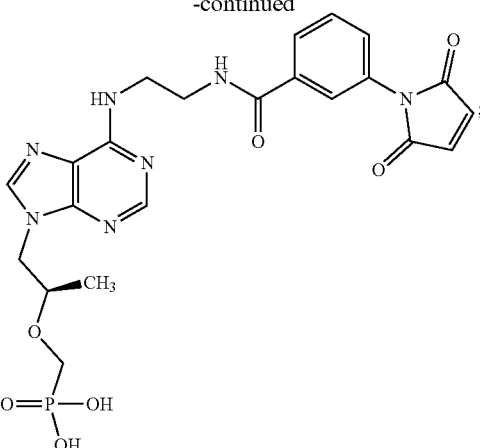

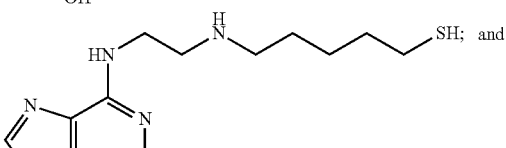

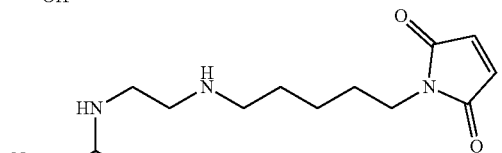

or a pharmaceutically acceptable salt thereof.

Any of the metabolites described herein may be used to generate metabolite derivatives. In certain embodiments, TFV metabolites (or TFV analogs) are generated. In certain embodiments, TAF metabolites (or TAF analogs) are generated. In certain embodiments, TDF metabolites (or TDF analogs) are generated. In certain embodiments, FTC metabolites (or TFV analogs) are generated.

Immunogenic Conjugates for Antibody Production

Any of the aforementioned compounds (e.g., NRTI derivatives) may be conjugated to an immunogenic composition to generate suitable immunogens for antibody production. Such immunogens may comprise carrier proteins. The carrier may be a protein, a lipid, a lipolized protein, a virus, a peptide, or a dendrimer of glycopeptides.

Examples of carrier proteins are tetanus toxoid (TT), diphtheria toxoid (DT), diphtheria toxin cross-reacting material 197 (CRM197), fragment C of TT. Keyhole limpet hemocyanin (KLH), bovine serum albumin (BSA), protein D, outer-membrane protein (OMP) and pneumolysin, diphtheria toxin cross-reacting material 197 (CRM197) or other DT point mutants, such as CRM176, CRM228, CRM45 (Uchida et al *J. Biol. Chem.* 218; 3838-3844, 1973), CRM 9, CRM 45, CRM102, CRM 103, and CRM107 and other mutations described in the art.

In certain embodiments, the carrier protein is KLH. In certain embodiments, the carrier protein is BSA.

Numerous linker compounds can be used to conjugate compounds of the present invention to a carrier protein. The linkers merely need to covalently bind with the reactive residue on the carrier protein (e.g., a cysteine or lysine) and the selected compound. Accordingly, any linker that reacts with the carrier protein residue and may be used to provide the relatively stable conjugates (site-specific or otherwise) of the instant invention is compatible with the teachings herein.

Numerous compatible linkers can advantageously bind to reduced cysteines and lysines, which are nucleophilic. Conjugation reactions involving reduced cysteines and lysines include, but are not limited to, thiol-maleimide, thiol-halogeno (acyl halide), thiol-ene, thiol-yne, thiol-vinylsulfone, thiol-bisulfone, thiol-thiosulfonate, thiol-pyridyl disulfide and thiol-parafluoro reactions. As further discussed herein, thiol-maleimide bioconjugation is one of the most widely used approaches due to its fast reaction rates and mild conjugation conditions.

The linkers of the instant invention can be linked to reactive thiol nucleophiles on cysteines, including free cysteines. To this end, the cysteines may be made reactive for conjugation with linker reagents by treatment with various reducing agent such as DTT or TCEP or mild reducing agents as set forth herein. In other embodiments, the linkers of the instant invention can be linked to a lysine.

In some embodiments, the linker contains an electrophilic functional group for reaction with a nucleophilic functional group on the carrier protein. Nucleophilic groups on carrier proteins include, but are not limited to: (i) N-terminal amine groups, (ii) side chain amine groups, e.g., lysine, (iii) side chain thiol groups, e.g., cysteine, and (iv) sugar hydroxyl or amino groups where the carrier protein is glycosylated. Amine, thiol, and hydroxyl groups are nucleophilic and capable of reacting to form covalent bonds with electrophilic groups on linker moieties and linker reagents including: (i) maleimide groups (ii) activated disulfides, (iii) active esters such as NHS (N-hydroxysuccinimide) esters, HOBt (N-hydroxybenzotriazole) esters, haloformates, and acid halides; (iv) alkyl and benzyl halides such as haloacetamides; and (v) aldehydes, ketones, carboxyl, and, some of which are exemplified as follows:

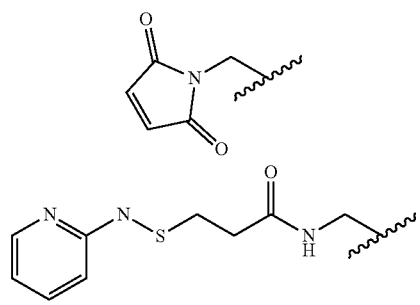

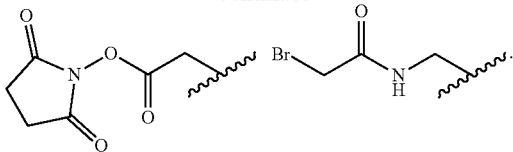

Antibodies of the Invention

Antibodies reactive with (e.g., raised against and/or specifically binds to) any one of the NRTI derivatives, or conjugates of same, described herein can be used. In certain embodiments, the antibodies may bind to any of the compounds (e.g., NRTI derivatives) described herein, and/or immunogenic conjugates of same. The antibodies can be polyclonal, chimeric, humanized, or monoclonal, and the term antibody is intended to encompass polyclonal, chimeric, humanized, and monoclonal antibodies, and functional fragments thereof. The terms polyclonal and monoclonal refer to the degree of homogeneity of an antibody preparation, and are not intended to be limited to particular methods of production.

Anti-NRTI derivative conjugate antibodies can be raised against appropriate immunogens, such as the immunogen compounds of the present invention, analogs or derivatives thereof, and conjugates of same.

An immunogenic composition comprising any of the compounds described herein (e.g., NRTI derivatives, or analogs) typically is used to prepare antibodies by immunizing a suitable subject, (e.g., rabbit, goat, mouse or other mammal) with the immunogen. An appropriate immunogenic preparation can contain, for example, chemically synthesized NRTI derivatives conjugated to a carrier protein. The preparation can further include an adjuvant, such as Freund's complete or incomplete adjuvant, or similar immunostimulatory agent. Immunization of a suitable subject with an immunogenic composition comprising any of the compounds described herein (e.g., NRTI derivatives, or analogs) induces a polyclonal anti-NRTI derivative conjugate antibody response.

Another aspect of the invention pertains to the use of anti-NRTI derivative conjugate antibodies. The term "antibody" as used herein refers to immunoglobulin molecules and immunologically active portions of immunoglobulin molecules, i.e., molecules that contain an antigen binding site which specifically binds (immunoreacts with) an NRTI derivative, or conjugate of same. Examples of immunologically active portions of immunoglobulin molecules include F(ab) and F(ab')₂ fragments which can be generated by treating the antibody with an enzyme such as pepsin. The invention provides polyclonal and monoclonal antibodies that bind NRTI derivative, or conjugate of same. The term "monoclonal antibody" or "monoclonal antibody composition", as used herein, may refer to a population of antibody molecules that contain only one species of an antigen binding site capable of immunoreacting with a particular chemical group of the NRTI derivative, or conjugate of same. A monoclonal antibody composition thus typically displays a single binding affinity for a particular NRTI derivative, or conjugate of same, with which it immunoreacts.

Polyclonal anti-NRTI derivative conjugate antibodies can be prepared as described above by immunizing a suitable subject with an immunogenic composition comprising the NRTI derivative conjugate. The antibody molecules directed against the NRTI derivative conjugate can be isolated from the mammal (e.g., from the blood) and further purified by well-known techniques, such as protein A chromatography to obtain the IgG fraction. At an appropriate time after immunization, i.e., when the anti-NRTI derivative conjugate antibody titers are highest, antibody-producing cells can be obtained from the subject and used to prepare monoclonal antibodies by standard techniques, such as the hybridoma technique originally described by Kohler and Milstein (1975) *Nature* 256:495-497) (see also, Brown et al. (1981) *J. Immunol.* 127:539-46; Brown et al. (1980) *J. Biol. Chem.* 255:4980-83; Yeh et al. (1976) *Proc. Natl. Acad. Sci. USA* 76:2927-31; and Yeh et al. (1982) *Int. J. Cancer* 29:269-75), the more recent human B cell hybridoma technique (Kozbor et al. (1983) *Immunol. Today* 4:72), the EBV-hybridoma technique (Cole et al. (1985), *Monoclonal Antibodies and Cancer Therapy*, Alan R. Liss, Inc., pp. 77-96) or trioma techniques. The technology for producing monoclonal antibody hybridomas is well-known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387-402; M. L. Gefter et al. (1977) *Somatic Cell Genet.* 3:231-36). Briefly, an immortal cell line (typically a myeloma) is fused to lymphocytes (typically splenocytes) from a mammal immunized with an immunogenic composition as described above, and the culture supernatants of the resulting hybridoma cells are screened to identify a hybridoma producing a monoclonal antibody that binds the NRTI derivative, or conjugate of same.

Any of the many well-known protocols used for fusing lymphocytes and immortalized cell lines can be applied for the purpose of generating an anti-NRTI derivative conjugate monoclonal antibody (see, i.e., G. Galfre et al. (1977) *Nature* 266:550-52; Gefter et al. *Somatic Cell Genet.*, cited supra; Lerner, *Yale J. Biol. Med.*, cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, i.e., the P3-NS1/1-Ag4-1, P3-x63-Ag8.653 or Sp2/O—Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind NRTI derivative, or conjugate of same, i.e., using an ELISA assay as described herein.

As an alternative to preparing monoclonal antibody-secreting hybridomas, a monoclonal anti-NRTI derivative conjugate antibody can be identified and isolated by screening a recombinant combinatorial immunoglobulin library (e.g., an antibody phage display library) with NRTI derivative conjugate to thereby isolate immunoglobulin library members that bind NRTI derivative, or conjugate of same. Kits for generating and screening phage display libraries are commercially available (e.g., the Pharmacia *Recombinant Phage Antibody System*, Catalog No. 27-9400-01; and the Stratagene SurfZAP™ *Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1369-1372; Hay et al. (1992) *Hum. Antibod. Hybridomas* 3:81-85; Huse et al. (1989) *Science* 246:1275-1281; Griffiths et al. (1993) *EMBO J.* 12:725-734; Hawkins et al. (1992) *J. Mol. Biol.* 226:889-896; Clackson et al. (1991) *Nature* 352:624-628; Gram et al. (1992) *Proc. Natl. Acad. Sci. USA* 89:3576-3580; Garrard et al. (1991) *Bio/Technology* 9:1373-1377; Hoogenboom et al. (1991) *Nucleic Acids Res.* 19:4133-4137; Barbas et al. (1991) *Proc. Natl. Acad. Sci. USA* 88:7978-7982; and McCafferty et al. *Nature* (1990) 348:552-554.

Additionally, recombinant anti-NRTI derivative conjugate antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Canc. Res.* 47:999-1005; Wood et al. (1985) *Nature* 314:446-449; and Shaw et al. (1988) *J. Natl. Cancer Inst.* 80:1553-1559); Morrison, S. L. (1985) *Science* 229:1202-1207; Oi et al. (1986) *BioTechniques* 4:214; Winter U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060.

Any of the aforementioned antibodies, or conjugates of same, may be linked using standard drug-antibody linkers, such as a disulfide linker (see certain embodiments below).

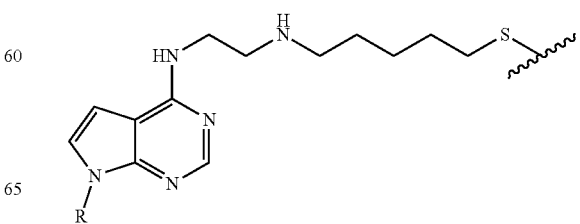

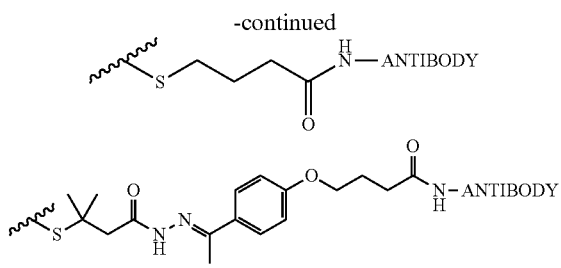

In another aspect, the invention provides antibodies that specifically bind to tenofovir or the tenofovir moiety of tenofovir derivatives. In some embodiments, the antibodies have an immunoglobulin heavy chain and an immunoglobulin light chain. In some embodiments, the antibodies are single-chain antibodies, heavy chain only antibodies, Fv fragments, Fab fragments, F(ab)$_2$ fragments, and the like. In some embodiments, the antibodies are polyclonal or, preferably, monoclonal antibodies. The design and production of antibodies is well known to those skilled in the art.

As described in the examples below, polyclonal and monoclonal antibodies have been developed for detecting metabolites of the tenofovir-derivative NRTIs. The monoclonal antibodies comprise the following amino acid sequences:

TABLE 1

Antibody Sequences

| Antibody | Full Length Sequence | Variable Region | CDR1 | CDR2 | CDR3 |
|---|---|---|---|---|---|
| 237L | MDMRAPTQLLGLLLLWLPGA RCADIVMTQTPSSVSAAVGG TVTINCQASQSIGNYCSWYQ QKPGQPPKLLIYLASNLASG VPSRFKGSGSGTQFTLTISD LECADAATYYCQSNYWTTSV NYGPFGGGTEVVVEGDPVAP TVLIFPPAADQVATGTVTIV CVANKYFPDVTVTWEVDGTT QTTGIENSKTPQNSADCTYN LSSTLTLTSTQYNSHKEYTC KVTQGTTSVVQSFNRGDC (SEQ ID NO: 1) | ASQSIGNYCSWYQQKPG QPPKLLIYLASNLASGV PSRFKGSGSGTQFTLTI SDLECADAATYYCQSNY WTTSVNYGP (SEQ ID NO: 11) | QASQSIGNYCS (SEQ ID NO: 17) | LASNLAS (SEQ ID NO: 25) | QSNYWTTSV NYGP (SEQ ID NO: 33) |
| 237H | METGLRWLLLVAVLKGVQCQ SLEESGGRLVTPGTPLTLTC TVSGIDLNRYSVGWVRQAPG EGLEWIGYIYRTGTTWYANW VKGRFTISKTSTTVDLKMTS LTTEDTATYFCARTGTSIAT DIWGPGTLVTVSSGQPKAPS VFPLAPCCGDTPSSTVTLGC LVKGYLPEPVTVTWNSGTLT NGVRTFPSVRQSSGLYSLSS VVSVTSSSQPVTCNVAHPAT NTKVDKTVAPSTCSKPTCPP PELLGRSSVFIFPPKPKDTL MISRTPEVTCVVVDVSQDDP EVQFTWYINNEQVRTARPPL REQQFNSTIRVVSTLPIAHQ DWLRGKEFKCKVHNKALPAP IEKTISKARGQPLEPKVYTM GPPREELSSRSVSLTCMING FYPSDISVEWEKNGKAEDNY KTTPTVLDSDGSYFLYSKLS VPTSEWQRGDVFTCSVMHEA LHNHYTQKSISRSPGK (SEQ ID NO: 2) | IDLNRYSVGWVRQAPGE GLEWIGYIYRTGTTWYA NWVKGRFTISKTSTTVD LKMTSLTTEDTATYFCA RTGTSIATDI (SEQ ID NO: 12) | IDLNRYSVG (SEQ ID NO: 18) | YIYRTGT TWYANWV (SEQ ID NO: 26) | TGTSIATDI (SEQ ID NO: 34) |
| 145L | MDTRAPTQLLGLLLLWLPGA TFAQVLTQTPSSVSAAVGGT VTINCQSSQNVYKDNYLAWY QQKPGQPPKRLIYYASTLAS GVPSRFSGSGSGTQFTLTIS DVQCDDAATYYCAGAYDCRS GDCRAFGGGTEVVVKGDPVA PTVLIFPPAADQVATGTVTI VCVANKYFPDVTVTWEVDGT TQTTGIENSKTPQNSADCTY NLSSTLTLTSTQYNSHKEYT CKVTQGTTSVVQSFNRGDC (SEQ ID NO: 3) | SSQNVYKDNYLAWYQQK PGQPPKRLIYYASTLAS GVPSRFSGSGSGTQFTL TISDVQCDDAATYYCAG AYDCRSGDCRA (SEQ ID NO: 13) | QSSQNVYKDNY LA (SEQ ID NO: 19) | YASTLAS (SEQ ID NO: 27) | AGAYDCRSG DCRA (SEQ ID NO: 35) |
| 145H | METGLRWLLLVAVLKGVQCQ SVEESGGRLVTPGGSLTLTC TASGFSLSSYNMQWVRQAPG KGLEYIGYIFSTGFTYYASW AKGRFTISKTSTTVDLKMTS | FSLSSYNMQWVRQAPGK GLEYIGYIFSTGFTYYA SWAKGRFTISKTSTTVD LKMTSLTTEDTATYFCA RGSTAKGDRDI | FSLSSYNMQ (SEQ ID NO: 20) | YIFSTGF TYYASWA (SEQ ID NO: 28) | GSTAKGDRD I (SEQ ID NO: 36) |

TABLE 1-continued

Antibody Sequences

| Antibody | Full Length Sequence | Variable Region | CDR1 | CDR2 | CDR3 |
|---|---|---|---|---|---|
| | LTTEDTATYFCARGSTAKGD RDIWGPGTLVTVSLGQPKAP SVFPLAPCCGDTPSSTVTLG CLVKGYLPEPVTVTWNSGTL TNGVRTFPSVRQSSGLYSLS SVVSVTSSSQPVTCNVAHPA TNTKVDKTVAPSTCSKPTCP PPELLGRSSVFIFPPKPKDT LMISRTPEVTCVVVDVSQDD PEVQFTWYINNEQVRTARPP LREQQFNSTIRVVSTLPIAH QDWLRGKEFKCKVHNKALPA PIEKTISKARGQPLEPKVYT MGPPREELSSRSVSLTCMIN GFYPSDISVEWEKNGKAEDN YKTTPTVLDSDGSYFLYSKL SVPTSEWQRGDVFTCSVMHE ALHNHYTQKSISRSPGK (SEQ ID NO: 4) | (SEQ ID NO: 14) | | | |
| 33L | MDTRAPTQLLGLLLLWLPGA RCAEVVMTQTPASVEAAVGD TVTIKCQASQSISSYLNWYQ QKPGQPPKLLIYRASNLRSG VPSRFKGSGSGTQFTLTISD LECADAATYYCQSNYYSRST NYVVPFGGGTEVVVKGDPVA PTVLIFPPSADLVATGTVTI VCVANKYFPDVTVTWEVDGT TQTTGIENSKTPQNSADCTY NLSSTLTLTSTQYNSHKEYT CKVTQGTTSVVQSFNRGDC (SEQ ID NO: 5) | ASQSISSYLNWYQQKPG QPPKLLIYRASNLRSGV PSRFKGSGSGTQFTLTI SDLECADAATYYCQSNY YSRSTNYVVP (SEQ ID NO: 15) | QASQSISSYLN (SEQ ID NO: 21) | RASNLRS (SEQ ID NO: 29) | QSNYYSRST NYVVP (SEQ ID NO: 37) |
| 33H | METGLRWLLLVAVLKGVQCQ SLEESGGRLVTPGTPLTLTC TVSGFSLSSSSMGWVRQAPG KGLEWIGYIYAGSGSRYYAS WANGRFTISKTSTTVDLKIT SPTTEDTATYFCGRVTSNGD NNIWGPGTLVTVSSGQPKAP SVFPLAPCCGDTPSSTVTLG CLVKGYLPEPVTVTWNSGTL TNGVRTFPSVRQSSGLYSLS SVVSVTSSSQPVTCNVAHPA TNTKVDKTVAPSTCSKPTCP PPELLGRSSVFIFPPKPKDT LMISRTPEVTCVVVDVSQDD PEVQFTWYINNEQVRTARPP LREQQFNSTIRVVSTLPIAH QDWLRGKEFKCKVHNKALPA PIEKTISKARGQPLEPKVYT MGPPREELSSRSVSLTCMIN GFYPSDISVEWEKNGKAEDN YKTTPTVLDSDGSYFLYSKL SVPTSEWQRGDVFTCSVMHE ALHNHYTQKSISRSPGK (SEQ ID NO: 6) | FSLSSSSMGWVRQAPGK GLEWIGYIYAGSGSRYY ASWANGRFTISKTSTTV DLKITSPTTEDTATYFC GRVTSNGDNNI (SEQ ID NO: 16) | FSLSSSSMG (SEQ ID NO: 22) | YIYAGSG SRYYASW ANG (SEQ ID NO: 30) | VTSNGDNNI (SEQ ID NO: 38) |
| MHC 2900LC | DVVMTQTPLSLPVSLGDQAS ISCRSSQSLVHSNGNTYLHW YLQKPGQSPKLLIYKVSNRF SGVPDRFSGSGSGTDFTLKI SRVEAEDLGVYFCSQGTHVP LTFGAGTKLELKRADAAPTV SIFPPSSEQLTSGGASVVCF LNNFYPKDINVKWKIDGSER QNGVLNSWTDQDSKDSTYSM SSTLTLTKDEYERHNSYTCE ATHKTSTSPIVKSFNRNEC (SEQ ID NO: 7) | DVVMTQTPLSLPVSLGD QASISCRSSQSLVHSNG NTYLHWYLQKPGQSPKL LIYKVSNRFSGVPDRFS GSGSGTDFTLKISRVEA EDLGVYFCSQGTHVPLT FGAGTKLELK (SEQ ID NO: 41) | RSSQSLVHSNG NTYLH (SEQ ID NO: 23) | KVSNRFS (SEQ ID NO: 31) | SQGTHVPLT (SEQ ID NO: 39) |
| MHC 2900HC | EVKLVESGGGLVQPGGSLRL SCATSGFTFTDYYMSWVRQP PGKALEWLGLIRNKAKGYTT EYSASVKGRFTISRDNSQSI | EVKLVESGGGLVQPGGS LRLSCATSGFTFTDYYM SWVRQPPGKALEWLGLI RNKAKGYTTEYSASVKG | GFTFTDY (SEQ ID NO: 24) | RNKAKGY T (SEQ ID NO: 32) | EALPY (SEQ ID NO: 40) |

TABLE 1-continued

Antibody Sequences

| Antibody | Full Length Sequence | Variable Region | CDR1 | CDR2 | CDR3 |
|---|---|---|---|---|---|
| | LYLQMNTLRAEDSATYYCAR<br>EALPYWGQGTLVTVSAAKTT<br>PPSVYPLAPGSAAQTNSMVT<br>LGCLVKGYFPEPVTVTWNSG<br>SLSSGVHTFPAVLQSDLYTL<br>SSSVTVPSSTWPSETVTCNV<br>AHPASSTKVDKKIVPRDCGC<br>KPCICTVPEVSSVFIFPPKP<br>KDVLTITLTPKVTCVVVDIS<br>KDDPEVQFSWFVDDVEHTA<br>QTQPREEQFNSTFRSVSELP<br>IMHQDWLNGKEFKCRVNSAA<br>FPAPIEKTISKTKGRPKAPQ<br>VYTIPPPKEQMAKDKVSLTC<br>MITDFFPEDITVEWQWNGQP<br>AENYKNTQPIMDTDGSYFVY<br>SKLNVQKSNWEAGNTFTCSV<br>LHEGLHNHHTEKSLSHSPGK<br>(SEQ ID NO: 9) | RFTISRDNSQSILYLQM<br>NTLRAEDSATYYCAREA<br>LPYWGQGTLVTVSA<br>(SEQ ID NO: 42) | | | |

In some embodiments, the light chain has a CDR1 region comprising an amino acid sequence selected from the group consisting of SEQ ID NOs: 17, 19, 21, and 30; a CDR2 region comprising an amino acid sequence selected from the group consisting of SEQ ID NOs: 25, 27, 29, and 31; and/or a CDR3 region comprising an amino acid sequence selected from the group consisting of SEQ ID NOs: 33, 35, 37, and 32.

In some embodiments, the antibody comprises a variable light chain amino acid sequence as set forth in SEQ ID NOs: 11, 13, 15, or 41.

In some embodiments, the heavy chain comprises a CDR1 region comprising an amino acid sequence selected from the group consisting of SEQ ID NOs: 18, 20, 22, and 23; a CDR2 region comprising an amino acid sequence selected from the group consisting of SEQ ID NOs: 26, 28, 30, and 31; and/or a CDR3 region comprising an amino acid sequence selected from the group consisting of SEQ ID NOs: 34, 36, 38, and 39.

In some embodiments, the antibody comprises a variable heavy chain amino acid sequence as set forth in SEQ ID NOs: 12, 14, 16, or 42.

Further disclosed are antibody preparations including any one or more of the antibodies disclosed herein. In some embodiments, the preparation is a monoclonal antibody preparation.

Also provided are isolated nucleic acid molecules encoding the heavy chain or light chain of any of the antibodies disclosed herein. In some embodiments, the nucleic acid is selected from the group consisting of a cloning vector, an expression vector, a heterologous recombination vector and a viral integration vector.

In addition, disclosed are cells transformed with any of the nucleic acids provided herein. In some embodiments, the cell is a mammalian cell. Some non-limiting examples of mammalian cells include rabbit, hamster, mouse, rat, chicken, goat, monkey, sheep, pig, horse, cow, or human cell.

An oligonucleotide or peptide with binding specificity (i.e., an aptamer) for the target epitopes discussed above for antibodies could also be used of the antibodies described herein.

Lateral Flow Immunoassays

Lateral flow immunoassays utilize strips of a membrane, preferably a cellulose membrane such as nitrocellulose, as the solid support for the immunoassay, onto which lines of reagent (e.g., anti-NRTI derivative conjugate antibody, such as an anti-TFV derivative conjugate or anti-TFV antibody) can be applied. Multiple small molecules (e.g., NRTIs such as TFV, TAF, or TDF) can be assayed by spatially separating the location of the application areas of the reagents. Additional reagent pads can be used below the test line(s) for other critical reagents and sample conditioning materials. When sample is added to the test device, the solution will flow across the pads below the test lines and rehydrate the sample conditioning compound and the critical reagents (e.g., NRTI derivative conjugates, such as HRP-NRTI derivative or HRP-TFV derivative, or antibodies to such NRTI derivatives, coupled to a detection label, such as those antibodies disclosed herein) for the assay and then pass across the specific test line and deposit a detection label which can be a visual indication (colloidal gold, colored latex or other labels known to those skilled in the art) or a label that requires an instrument to measure the signal (fluorescence, chemiluminesence). An additional material can be added above the test line to absorb fluid that passes by the test lines.

The end result is the appearance or absence of a colored line or spot, which can be compared to a control line. In some instances, the control line is useful for the detection of a marker of urine in order to ensure that the sample tested is indeed urine. Preferably, the marker of urine is present at a concentration significantly different in urine compared to the amount in other common matrices (i.e., blood) so as to validate that the sample tested is urine.

In one embodiment, the system may include a base or support layer and an absorbent matrix comprising at least one absorbent layer through which a liquid sample can flow along a flow path by force or by capillary action. The base layer may also be absorbent and be in fluid communication with the absorbent matrix, such that the flow path of liquid sample passes through both the absorbent matrix and the base layer. The flow path includes at least two regions, where the first region is a sample application region, and the second region is a detection region.

Smaller molecules can be detected using a competitive format where only one antibody or binding partner is utilized to detect the drug of interest. The assays can be formatted in a method that provides a positive read, in which a line appears when drug is present, or a negative read, in which the line disappears when the drug is present.

In one embodiment of the invention, the test device is a competitive immunoassay utilizing a lateral flow format with a negative read out that measures a single drug substance. The lateral flow strip has a sample pad that contains the buffering and sample treatment materials. The sample pad is in contact with a conjugate pad that contains a label linked to a derivative of the drug substance. The conjugate pad is in contact with a solid support, such as nitrocellulose, that has had an antibody striped onto it and also has a control line that has an antibody or binding partner that will bind the conjugate in both the presence and absence of the target drug. The test device may have an absorbent pad downstream from the test zones to facilitate flow through the device. The device may optionally have a device housing to contain the strip and create an opening for the addition of sample to the device. The presence of a line in the test zone and the control zone would indicate that the subject had not been routinely taking the target drug and the absence of a line would indicate that they had been taking the drug.

In one embodiment of the invention, the test device is a competitive immunoassay utilizing a lateral flow format with a negative read out that measures a single drug substance. The lateral flow strip has a sample pad that contains the buffering and sample treatment materials. The sample pad is in contact with a conjugate pad that contains a label linked to an antibody made to the drug substance. The conjugate pad is in contact with a solid support, such as nitrocellulose, that has had a derivative of the target drug striped onto it and also has a control line that has an antibody or binding partner that will bind the conjugate in both the presence and absence of the target drug. The test device may have an absorbent pad downstream from the test zones to facilitate flow through the device. The device may optionally have a device housing to contain the strip and create an opening for the addition of sample to the device. The presence of a line in the test zone and the control zone would indicate that the subject had not been routinely taking the target drug and the absence of a line would indicate that they had been taking the drug.

In one embodiment of the invention, the test device is a competitive immunoassay utilizing a lateral flow format with a positive read out that measures a single drug substance. The lateral flow strip has a sample pad that contains the buffering and sample treatment materials. The sample pad is in contact with a conjugate pad that contains a label that is linked to an antibody made to the drug substance. The conjugate pad is in contact with a solid support, such as nitrocellulose, that has had a derivative of the target drug striped onto it at a position that is not visible to the user and a binding partner for the conjugate not related to the drug at the test line (ex Avidin/Biotin). The solid support also has a control line that has an antibody or binding partner that will bind a secondary conjugate to indicate that the device has been run. The test device may have an absorbent pad downstream from the test zones to facilitate flow through the device. The device may optionally have a device housing to contain the strip and create an opening for the addition of sample to the device. The presence of a line in the test zone and the control zone would indicate that the subject had been routinely taking the target drug and the absence of a line would indicate that they had not been taking the drug.

In one embodiment of the invention, the test device is a competitive immunoassay utilizing a lateral flow format with a negative read out that measures a combination of drug substances. The lateral flow strip has a sample pad that contains the buffering and sample treatment materials. The sample pad is in contact with a conjugate pad that contains a label linked to 2 or more derivatives of drug substances. The conjugate pad is in contact with a solid support, such as nitrocellulose, that has had an antibodies striped onto it at 2 or more test positions and also has a control line that has an antibody or binding partner that will bind the conjugate in both the presence and absence of the target drug. The test device may have an absorbent pad downstream from the test zones to facilitate flow through the device. The device may optionally have a device housing to contain the strip and create an opening for the addition of sample to the device. In this embodiment, the pattern of reactivity of the 2 or more drugs could indicate the adherence to the recommended dosing for the drugs. In one potential outcome, a lateral flow test readout of two positive test lines or spots could indicate that the individual providing the sample was taking a NRTI according to the prescribed dosage schedule, whereas a lateral flow test readout of one positive test line or spot could indicate that the individual providing the sample was taking a NRTI but not according to the prescribed dosage schedule, and a lateral flow test readout of zero positive test lines or spots could indicate that the individual providing the sample was not taking a NRTI.

In one embodiment, the NRTI of the invention can be detected in a system that takes the form of a laboratory test, for example a type of numbered well plate (e.g., 96 well plate). In one embodiment, the lateral flow device can be in the form of a cartridge that can be read by a machine. Preferably, the machine is automated.

In one embodiment, the system of the invention includes (i) a POCT and (ii) a digital device. In one embodiment, a digital device interacts with a POCT. In one embodiment, a digital device analyzes the results from a POCT. In one embodiment, a digital device records the results from a POCT. In one embodiment, a digital device reports the results from a POCT. In one embodiment, a digital device analyzes, records and/or reports the results from multiple POCT.

In some embodiments, the digital device is a camera equipped smartphone or tablet. In some embodiments, uses the system of the invention includes a smart phone camera and an app. YouFor example, one holds the smartphone camera over the lateral flow test, and the camera quantifies the level of the drug in the urine based on the intensity of the line. That number can then be shared with Electronic Medical Record, other apps, or hosted to a database., In some embodiments, the test can be administered on an immunoassay platform. Non-limiting examples include the Alere reader (etc.http://www.clpmag.com/2017/04/fda-clears-alere-immunoassay-analyzer) or the Abbott I-Stat (https://www.pointofcare.abbott/us/en/offerings/istat).

The invention disclosed is not limited to the platform chosen to measure the NRTI concentrations. Rapid tests are well known and can be formatted in a lateral flow, flow through, capillary, biosensor and a number of other formats.

Biological Samples

Biological samples to be analyzed using the invention may be of any biological tissue or fluid containing the NRTI. Frequently the sample will be a "clinical sample" which is a sample derived from a patient. Typical samples for analysis include, but are not limited to, biological fluid samples such as sputum (a.k.a saliva), blood, plasma, milk, semen and urine.

Methods for collection of biological fluids from patients are well known in the art. In one embodiment, collection of a biological fluid for use in a lateral flow rapid visual NRTI test is with a sample cup or other receptacle. In one embodiment, a lateral flow device of the invention is inserted into a sample cup or other receptacle containing a biological fluid specimen. Receptacles appropriate for use in collecting biological fluid samples for use with the invention are not necessarily limited and are well known in the art. In one embodiment, a patient places an absorbent wick of a lateral flow device of the invention into their urine flow to collect the biological fluid for analysis. In one embodiment, a lateral flow device of the invention is inserted into an oral cavity and contacts the oral mucosa to collect the biological fluid for analysis.

In one embodiment, biological samples or aliquots of biological samples are shipped to a lab for analysis using a lab based test. In one embodiment, biological samples or aliquots of biological samples are frozen for shipment to a lab for analysis using a lab based test.

Test Results

In some embodiments, a lateral flow device provides results within 1 to 40 minutes. In some embodiments, a lateral flow device provides results within 1, 2, 3, 4, 5, 6, 7, 8, 9, 10, 11, 12, 13, 14, 15, 20, 25, 30 or 40 minutes. In these embodiments, the results can be read by the patient or provider and interpreted. In one embodiment, the patient sample is analyzed using a lab based test and results are sent by confidential electronic record or by confidential fax back to the patient or provider. Other methods of providing results to providers and patients are well known.

In one embodiment, the results are used by a provider to monitor the adherence of a patient to a prescribed dosing schedule. In one embodiment, the test results are interpreted by a provider and used to inform a counseling strategy with the patient either in person or by phone, email, text message, or other communication medium. This includes but is not limited to a discussion with the patient, formulating a care plan, adjusting insurance coverage, addressing barriers to medication adherence, assigning an individual to check on compliance, using a digital solution such as text messaging to improve adherence, or a mechanical solution such as a pill dispenser that records and/or transmits data on pill consumption. Additionally, the provider can use this information to flag patients in which urine testing has shown that they are either not protected (e.g., urine TFV concentration <10 ng/mL, if using the LC-MS/MS based assay) or incompletely protected (e.g., urine TFV concentration between 10 and 1000 ng/mL, if using the LC-MS/MS based assay) from HIV acquisition based on their most recent urine TFV levels.

Additional cut-offs for TFV using any of the immunoassays (e.g., lateral flow assays) may be determined using the procedures as described in Koenig et al. *HIV Med.* 2017 July; 18(6):412-418. Likewise, cut-offs for other metabolites, such as TAF, in any of the assays (e.g., lateral flow assays) described herein can be determined using the methodology described in Koenig et al. *HIV Med.* 2017 July; 18(6):412-418.

In one embodiment, the patient could use the system outside of a clinical setting. In one embodiment, the patient could use the system at the direction of a provider. In one embodiment, the patient could inform their provider of their results. This could include but is not limited to informing the provider after each individual test through a phone call, messaging, or digital app or performing multiple tests and providing the results to the provider at intermittent visits.

In an alternative embodiment, the patient could use the system independently of provider oversight. In this embodiment, the results could used by a patient to confirm the presence of a NRTI prior to an encounter wherein they are at risk of contracting HIV.

In one embodiment, testing can be performed daily. In one embodiment, testing can be performed before a high-risk encounter in which the patient is at risk of becoming HIV infected. In one embodiment, testing can be performed at a frequency determined by a provider or research director.

In one embodiment, a point-of-care test (POCT) of the invention can be used along with a handheld device. In one embodiment, a handheld device for use with a POCT of the invention analyzes the results of the POCT. In one embodiment, the analysis is performed using an electronic detection method incorporated into the handheld device. In one embodiment, the handheld device of the invention interfaces with a computer program. In one embodiment, a computer program is an application or web-based evaluation tool. In one embodiment, a user accesses a computer program to analyze, track, or visualize the test results. In one embodiment, a computer program for analyzing, tracking, or visualizing the test results from a POCT also serves to report test results to a physician or other party.

Metabolites

In some embodiments, the system disclosed herein includes application of a biological fluid obtained from a test sample to a system for the detection of one or more metabolites that are associated with a pharmaceutical. In one embodiment, the pharmaceutical is used to treat a disease. In one embodiment, the pharmaceutical is used as a preventative measure. Such metabolites include, but are not limited to small molecules, metabolic products, degradation products, or related metabolites of one or more NRTIs (e.g., TFV, TAF, TDF, FTC).

In some embodiments, a pharmaceutical is comprised of one or more NRTIs. In one embodiment, the pharmaceutical is used to treat HIV infection. In one embodiment, the pharmaceutical is used to prevent HIV infection. In some embodiments, the pharmaceutical is used to treat or prevent Hepatitis B infection. Such metabolites include, but are not limited to small molecules, metabolic products, degradation products, or related metabolites of one or more NRTIs (e.g., TFV, TAF, TDF, FTC).

In some embodiments, the present disclosure relates to immunoassays for assessing (e.g., detecting or quantifying) at least one NRTI of interest in a test sample. In one embodiment, the invention relates to an immunoassay to detect TFV. In one embodiment, the invention relates to an immunoassay to detect FTC. In one embodiment, the invention relates to an immunoassay to detect both TFV and FTC.

Controls with respect to the presence or absence of the NRTI or concentration of the NRTI may be to metabolites abundant in the sample to be tested. In one embodiment, controls may be to markers abundant in at least one of urine, saliva, blood or plasma. As described elsewhere herein, comparison of the test patterns of the NRTI to be tested with those of the controls can be used to identify the presence of the NRTI. In this context, the control or control group is used for purposes of establishing proper use and function of the systems and assay of the invention. Therefore, mere detection of a NRTI of the invention without the requirement of comparison to a control group can be used to identify the presence of the NRTI. In this manner, the system according to the present invention may be used for qualitative, semi-quantitative or quantitative answers.

The concentration or level of a NRTI in urine is associated with plasma concentration levels of the NRTI. Thus, the concentration level of NRTIs in urine serves as a signpost for the increased or decreased risk of contracting HIV upon exposure that is afforded by the NRTI. For example using the LC-MS/MS based assay, a urine TFV concentration <10 ng/mL may indicate that a patient is at high risk of contracting HIV upon an exposure incident, whereas a urine TFV concentration between 10 and 1000 ng/mL may indicate that a patient is at some risk of contracting HIV upon an exposure incident and a urine TFV concentration >1000 ng/mL may indicate that a patient is at low risk of contracting HIV upon an exposure incident.

Additional cut-offs for TFV using any of the immunoassays (e.g., lateral flow assays) may be determined using the procedures as described in Koenig et al. *HIV Med.* 2017 July; 18(6):412-418. Likewise, cut-offs for other metabolites, such as TAF, in any of the assays (e.g., lateral flow assays) described herein can be determined using the methodology described in Koenig et al. *HIV Med.* 2017 July; 18(6):412-418.

Detecting a Small Molecule

The concentration of the small molecule (e.g., metabolite, NRTI, or any of the compounds described herein, or derivatives or conjugates of same) in a sample may be determined by any suitable assay. A suitable assay may include one or more of the following methods, an enzyme assay, an immunoassay, mass spectrometry, chromatography, electrophoresis or an antibody microarray, or any combination thereof. Thus, as would be understood by one skilled in the art, the system and methods of the invention may include any method known in the art to detect a metabolite in a sample.

In one embodiment, the sample of the invention is a biological sample. The biological sample can originate from solid or fluid samples. Preferably the sample is a fluid sample. The sample of the invention may comprise urine, whole blood, blood serum, blood plasma, sweat, mucous, saliva, milk, semen and the like.

Immunoassays

In one embodiment, the systems and methods of the invention can be performed in the form of various immunoassay formats, which are well known in the art. Immunoassays, in their most simple and direct sense, are binding assays involving binding between antibodies and antigen. Many types and formats of immunoassays are known and all are suitable for detecting the disclosed metabolites. Examples of immunoassays are enzyme linked immunosorbent assays (ELISAs), enzyme linked immunospot assay (ELISPOT), radioimmunoassays (RIA), radioimmune precipitation assays (RIPA), immunobead capture assays, Western blotting, dot blotting, gel-shift assays, Flow cytometry, protein arrays, multiplexed bead arrays, magnetic capture, in vivo imaging, fluorescence resonance energy transfer (FRET), fluorescence recovery/localization after photobleaching (FRAP/FLAP), a competitive assay, an immunoassay using a biosensor, an immunoprecipitation assay, an agglutination assay, a turbidity assay, a nephlelometric assay, etc.

In general, immunoassays involve contacting a sample suspected of containing a molecule of interest (such as the disclosed metabolites) with an antibody to the molecule of interest or contacting an antibody to a molecule of interest (e.g., anti-NRTI derivative conjugate antibodies described herein) with a molecule that can be bound by the antibody, as the case may be, under conditions effective to allow the formation of immunocomplexes. Contacting a sample with the antibody to the molecule of interest or with the molecule that can be bound by an antibody to the molecule of interest under conditions effective and for a period of time sufficient to allow the formation of immune complexes (primary immune complexes) is generally a matter of simply bringing into contact the molecule or antibody and the sample and incubating the mixture for a period of time long enough for the antibodies to form immune complexes with, i.e., to bind to, any molecules (e.g., metabolites) present to which the antibodies can bind. In many forms of immunoassay, the sample-antibody composition, such as a tissue section, ELISA plate, dot blot or Western blot, can then be washed to remove any non-specifically bound antibody species, allowing only those antibodies specifically bound within the primary immune complexes to be detected.

Immunoassays can include methods for detecting or quantifying the amount of a molecule of interest (such as the disclosed metabolites or their antibodies) in a sample, which methods generally involve the detection or quantitation of any immune complexes formed during the binding process. In general, the detection of immunocomplex formation is well known in the art and can be achieved through the application of numerous approaches. These methods are generally based upon the detection of a label, such as any radioactive, fluorescent, biological or enzymatic tags or any other known label. See, for example, U.S. Pat. Nos. 3,817,837; 3,850,752; 3,939,350; 3,996,345; 4,277,437; 4,275,149 and 4,366,241, each of which is incorporated herein by reference in its entirety and specifically for teachings regarding immunodetection methods and labels.

As used herein, a label can include a fluorescent dye, a member of a binding pair, such as biotin/streptavidin, a metal (e.g., gold), or an epitope tag that can specifically interact with a molecule that can be detected, such as by producing a colored substrate or fluorescence. Substances suitable for detectably labeling antibodies, or NRTI derivatives, or conjugates and derivatives thereof, include fluorescent dyes (also known herein as fluorochromes and fluorophores) and enzymes that react with colorometric substrates (e.g., horseradish peroxidase (HRP)). The use of fluorescent dyes is generally preferred in the practice of the invention as they can be detected at very low amounts. Furthermore, in the case where multiple small molecules (e.g., metabolites or NRTI) are reacted with a single array, each small molecules (e.g., metabolites or NRTI) can be labeled with a distinct fluorescent compound for simultaneous detection. Labeled spots on the array are detected using a fluorimeter, the presence of a signal indicating a labeled small molecule (e.g., metabolites or NRTI) bound to a specific antibody.

Fluorophores are compounds or molecules that luminesce. Typically fluorophores absorb electromagnetic energy at one wavelength and emit electromagnetic energy at a second wavelength.

There are two main types of immunoassays, homogeneous and heterogeneous. In homogeneous immunoassays, both the immunological reaction between an antigen and an antibody and the detection are carried out in a homogeneous reaction. Heterogeneous immunoassays include at least one separation step, which allows the differentiation of reaction products from unreacted reagents. A variety of immunoassays can be used to detect one or more of the small molecules disclosed (e.g., NRTI, any of the compounds described herein, or derivatives, conjugates, and analogs thereof) or incorporated by reference herein.

ELISA is a heterogeneous immunoassay, which can be used in the methods disclosed herein. The assay can be used to detect in various formats.

ELISA can also be used as a competitive assay. In the competitive assay format, the test specimen containing the antigen (e.g., metabolite such as TFV) to be determined is mixed with a precise amount of enzyme-labeled antigen (e.g., HRP-TFV or HRP-TFV derivative) and both compete for binding to an anti-antigen antibody (e.g., anti-NRTI derivative conjugate antibody) attached to a solid surface. Excess free enzyme-labeled antigen is washed off before the substrate for the enzyme is added. The amount of color intensity resulting from the enzyme-substrate interaction is a measure of the amount of antigen in the sample tested. A heterogeneous immunoassay, such as an ELISA, can be used to detect any of the small molecule disclosed (e.g., NRTI, any of the compounds described herein, or derivatives, conjugates, and analogs thereof) or incorporated by reference herein.

Homogeneous immunoassays include, for example, the Enzyme Multiplied Immunoassay Technique (EMIT), which typically includes a biological sample comprising the metabolites to be measured, enzyme-labeled molecules of the metabolites to be measured, specific antibody or antibodies binding the metabolites to be measured, and a specific enzyme chromogenic substrate. In a typical EMIT, excess of specific antibodies is added to a biological sample. If the biological sample contains the small molecule (e.g., metabolite or NRTI) to be detected, such small molecule (e.g., metabolite or NRTI) bind to the antibodies. A measured amount of the corresponding enzyme-labeled small molecule (e.g., metabolite- or NRTI-conjugate derivative) is then added to the mixture. Antibody binding sites not occupied by such small molecule (e.g., metabolite or NRTI) in the sample are occupied with molecules of the added enzyme-labeled small molecule (e.g., metabolite- or NRTI-conjugate derivative). A high concentration of the small molecule (e.g., metabolite or NRTI) to be detected in the sample causes lower absorbance readings. Less small molecule (e.g., metabolite or NRTI) in the sample results in more enzyme activity and consequently higher absorbance readings. A homogenous immunoassay, such as an EMIT, can be used to detect any of the small molecule (e.g., metabolite or NRTI) disclosed or incorporated by reference herein.

In many immunoassays, as described elsewhere herein, detection of antigen is made with the use of antigens specific antibodies as detector molecules. However, immunoassays and the systems and methods of the present invention are not limited to the use of antibodies as detector molecules. Any substance that can bind or capture the antigen within a given sample may be used. Aside from antibodies, suitable substances that can also be used as detector molecules include but are not limited to enzymes, peptides, proteins, and nucleic acids. Further, there are many detection methods known in the art in which the captured antigen may be detected. In some assays, enzyme-linked antibodies produce a color change. In other assays, detection of the captured antigen is made through detecting fluorescent, luminescent, chemiluminescent, or radioactive signals. The system and methods of the current invention is not limited to the particular types of detectable signals produced in an immunoassay.

Immunoassay kits are also included in the invention. These kits include, in separate containers monoclonal or polyclonal. antibodies having binding specificity for the compounds of the present invention, or analogs or derivatives. This immunoassay kit may be utilized for the practice of the various methods provided herein. The monoclonal antibodies and the anti-antibody immunoglobulins can be provided in an amount of about 0.001 mg to 100 grams, and more preferably about 0.01 mg to 1 gram. The anti-antibody immunoglobulin may be a polyclonal immunoglobulin, protein A or protein G or functional fragments thereof, which may be labeled prior to use by methods known in the art. In several embodiments, the immunoassay kit includes two, three or four of: antibodies that specifically bind a small molecule (such as the metabolite, NRTI, or any of the compounds described herein) disclosed or incorporated herein.

In one embodiment, the immunoassay kit of the invention can comprise (a) a sample pad, (b) a conjugated label pad, the conjugated label pad having a detectable label, a portion of the conjugated label pad and a portion of the sample pad forming a first interface, (c) a lateral-flow assay comprising a membrane, a portion of the membrane and a portion of the conjugated label pad forming a second interface, and (d) at least one antibody bound to the membrane, the first interface allowing fluid to flow from the sample pad to the conjugated label pad and contact the detectable label wherein the metabolite present in the sample forms an metabolite-conjugated label complex, the second interface allowing fluid to flow from the conjugated label pad to the membrane and to contact the at least one membrane-bound antibody to form to an metabolite-antibody complex and cause the detectable label to form a detectable signal.

In one embodiment, the immunoassay kit of the invention includes an additional component including but not limited to one or more of instructional material and sample collection receptacles. In one embodiment, the kit of the invention includes a single immunoassay system. In one embodiment, the kit of the invention includes more than one immunoassay system.

In one embodiment, the kit of the invention includes a handheld device. In one embodiment, the kit includes a system for or access to a computer software for analyzing, recording, monitoring, tracking and/or reporting the results of the POCT of the invention.

Point-of-Use Devices

Point-of-use analytical tests have been developed for the routine identification or monitoring of health-related conditions (such as pregnancy, cancer, endocrine disorders, infectious diseases or drug abuse) using a variety of biological samples (such as urine, serum, plasma, blood, saliva). Some of the point-of-use assays are based on highly specific interactions between specific binding pairs, such as small molecule (e.g., metabolite, NRTI, or any of the compounds described herein, or derivatives and conjugates thereof)/antibody, antigen/antibody, hapten/antibody, lectin/carbohydrate, apoprotein/cofactor and biotin/(strept)avidin. In some point-of use devices, assays are performed with test strips in which a specific binding pair member is attached to a mobilizable material (such as a metal sol or beads made of latex or glass) or an immobile substrate (such as glass fibers, cellulose strips or nitrocellulose membranes). Other point-of use devices may comprise optical biosensors, photometric biosensors, electrochemical biosensor, or other types of biosensors. Suitable biosensors in point-of-use devices for performing methods of the invention include "cards" or "chips" with optical or acoustic readers. Biosensors can be configured to allow the data collected to be electronically transmitted to the physician for interpretation and thus can form the basis for e-medicine, where diagnosis and monitoring can be done without the need for the patient to be in proximity to a physician or a clinic.

Detection of a metabolite in a sample can be carried out using a sample capture device, such as a lateral flow device (for example a lateral flow test strip) that allows detection of one or more metabolites, such as those described herein.

The test strips of the present invention include a flow path from an upstream sample application area to a test site. For example, the flow path can be from a sample application area through a mobilization zone to a capture zone. The mobilization zone may contain a mobilizable antibody that interacts with a small molecule (e.g., metabolite, NRTI, or compounds described herein, or conjugates or derivatives of same), and the capture zone contains a reagent that binds the small molecule (e.g., metabolite, NRTI, or compounds described herein, or conjugates or derivatives of same) to detect the presence (or absence) of a small molecule (e.g., metabolite, NRTI, or compounds described herein, or conjugates or derivatives of same) in the sample.

The test strips disclosed herein are not limited to NRTI adherence monitoring, but could be combined with other tests in a single lateral flow strip or immunoassay cartridge. In a non-limiting example, the test strips disclosed herein could be combined with other tests in a single lateral flow strip or immunoassay cartridge to measure both TFV adherence and implement another test of clinical relevance, such as HIV infection status.

Examples of migration assay devices, which usually incorporate within them reagents that have been attached to colored labels, thereby permitting visible detection of the assay results without addition of further substances are found, for example, in U.S. Pat. No. 4,770,853 (incorporated herein by reference). Multiple zone lateral flow test strips are disclosed in U.S. Pat. Nos. 5,451,504, 5,451,507, and U.S. Pat. No. 5,798,273 (incorporated by reference herein). U.S. Pat. No. 6,656,744 (incorporated by reference) discloses a lateral flow test strip in which a label binds to an antibody through a streptavidin-biotin interaction.

Flow-through type assay devices were designed, in part, to obviate the need for incubation and washing steps associated with dipstick assays. Flow-through immunoassay devices involve a capture reagent (such as one or more antibodies) bound to a porous membrane or filter to which a liquid sample is added. As the liquid flows through the membrane, target small molecule (such as the metabolite, NRTI, or any of the compounds described herein) binds to the capture reagent. The addition of sample is followed by (or made concurrent with) addition of detector reagent, such as labeled antibody (e.g., gold-conjugated or colored latex particle-conjugated antibody). Alternatively, the detector reagent may be placed on the membrane in a manner that permits the detector to mix with the sample and thereby label the small molecule (such as the metabolite, NRTI, or any of the compounds described herein). The visual detection of detector reagent provides an indication of the absence of target small molecule (e.g., metabolite, NRTI, or compounds described herein, or conjugates or derivatives of same) in the sample. Representative flow-through assay devices are described in U.S. Pat. Nos. 4,246,339; 4,277,560; 4,632,901; 4,812,293; 4,920,046; and 5,279,935; U.S. Patent Application Publication Nos. 20030049857 and 20040241876; and WO 08/030,546. Migration assay devices usually incorporate within them reagents that have been attached to colored labels, thereby permitting visible detection of the assay results without addition of further substances. See, for example, U.S. Pat. No. 4,770,853; PCT Publication No. WO 88/08534.

Devices described herein generally include a strip of absorbent material (such as a microporous membrane), which, in some instances, can be made of different substances each joined to the other in zones, which may be abutted and/or overlapped. In some examples, the absorbent strip can be fixed on a supporting non-interactive material (such as nonwoven polyester), for example, to provide increased rigidity to the strip. Zones within each strip may differentially contain the specific binding partner(s) and/or other reagents required for the detection and/or quantification of the particular small molecule (e.g., metabolites or NRTI) being tested for, for example, one or more small molecules (e.g., metabolites or NRTI) disclosed herein. Thus these zones can be viewed as functional sectors or functional regions within the test device.

In general, a fluid sample is introduced to the strip at the proximal end of the strip, for instance by dipping or spotting. A sample is collected or obtained using methods well known to those skilled in the art. The sample containing the particular metabolites or NRTI to be detected may be obtained from any biological source. In a particular example, the biological source is urine. The sample may be diluted, purified, concentrated, filtered, dissolved, suspended or otherwise manipulated prior to assay to optimize the immunoassay results. The fluid migrates distally through all the functional regions of the strip. The final distribution of the fluid in the individual functional regions depends on the adsorptive capacity and the dimensions of the materials used.

In some embodiments, porous solid supports, such as nitrocellulose, described elsewhere herein are preferably in the form of sheets or strips. The thickness of such sheets or strips may vary within wide limits, for example, from about 0.01 to 0.5 mm, from about 0.02 to 0.45 mm, from about 0.05 to 0.3 mm, from about 0.075 to 0.25 mm, from about 0.1 to 0.2 mm, or from about 0.11 to 0.15 mm. The pore size of such sheets or strips may similarly vary within wide limits, for example from about 0.025 to 15 microns, or more specifically from about 0.1 to 3 microns; however, pore size is not intended to be a limiting factor in selection of the solid support. The flow rate of a solid support, where applicable, can also vary within wide limits, for example from about 12.5 to 90 sec/cm (i.e., 50 to 300 sec/4 cm), about 22.5 to 62.5 sec/cm (i.e., 90 to 250 sec/4 cm), about 25 to 62.5 sec/cm (i.e., 100 to 250 sec/4 cm), about 37.5 to 62.5 sec/cm (i.e., 150 to 250 sec/4 cm), or about 50 to 62.5 sec/cm (i.e., 200 to 250 sec/4 cm).

Another common feature to be considered in the use of assay devices is a means to detect the formation of a complex between a small molecule (such as one or more metabolite, NRTI, or compounds described herein) and a capture reagent (such as one or more antibodies). A detector (also referred to as detector reagent) serves this purpose. A detector may be integrated into an assay device (for example includes in a conjugate pad), or may be applied to the device from an external source.

A detector may be a single reagent or a series of reagents that collectively serve the detection purpose. In some instances, a detector reagent is a labeled binding partner specific for the small molecule (e.g., metabolite, NRTI, or compounds described herein, or conjugates or derivatives of same) (such as a gold-conjugated antibody for a particular metabolite, or NRTI, of interest).

In other instances, a detector reagent collectively includes an unlabeled first binding partner specific for the small molecule (e.g., metabolite, NRTI, or compounds described herein, or conjugates or derivatives of same) and a labeled second binding partner specific for the first binding partner and so forth. Thus, the detector can be a labeled antibody specific for a small molecule (e.g., metabolite, NRTI, or any of the compounds described herein). The detector can also be an unlabeled first antibody specific for the small molecule (e.g., metabolite, NRTI, or any of the compounds described herein) of interest and a labeled second antibody that specifically binds the unlabeled first antibody. In each instance, a detector reagent specifically detects bound small molecule (e.g., metabolite, NRTI, or compounds described herein, or conjugates or derivatives of same) of a small molecule (e.g., metabolite, NRTI, or compounds described herein, or conjugates or derivatives of same)-capture reagent complex and, therefore, a detector reagent preferably does not substantially bind to or react with the capture reagent or other components localized in the small molecule (e.g., metabolite, NRTI, or compounds described herein, or conjugates or derivatives of same) capture area. Such non-specific binding or reaction of a detector may provide a false positive result. Optionally, a detector reagent can specifically recognize a positive control molecule (such as a non-specific human IgG for a labeled Protein A detector, or a labeled Protein G detector, or a labeled anti-human Ab(Fc)) that is present in a secondary capture area.

Flow-Through Device Construction and Design

A flow-through device involves a capture reagent (such as one or more antibodies) immobilized on a solid support, typically, microtiter plate or a membrane (such as, nitrocellulose, nylon, or PVDF). In a simple representative format, the membrane of a flow-through device is placed in functional or physical contact with an absorbent layer, which acts as a reservoir to draw a fluid sample through the membrane. Optionally, following immobilization of a capture reagent, any remaining small molecule- (e.g., metabolite, NRTI, or any of the compounds described herein) binding sites on the membrane can be blocked (either before or concurrent with sample administration) to minimize nonspecific interactions.

In operation of a flow-through device, a fluid sample is placed in contact with the membrane. Typically, a flow-through device also includes a sample application area (or reservoir) to receive and temporarily retain a fluid sample of a desired volume. The sample passes through the membrane matrix. In this process, a small molecule in the sample (such as the metabolite, NRTI, or any of the compounds described herein) can specifically bind to the immobilized capture reagent (such as one or more antibodies). Where detection of a small molecule (e.g., metabolite, NRTI, or any of the compounds described herein)-capture reagent complex is desired, a detector reagent (such as labeled antibodies that specifically bind one or more small molecule (e.g., metabolite, NRTI, or any of the compounds described herein)) can be added with the sample or a solution containing a detector reagent can be added subsequent to application of the sample. If a small molecule (e.g., metabolite, NRTI, or compounds described herein, or conjugates or derivatives of same) is specifically bound by capture reagent, a characteristic attributable to the particular detector reagent can be observed on the surface of the membrane. Optional wash steps can be added at any time in the process, for instance, following application of the sample, and/or following application of a detector reagent.

Lateral Flow Device Construction and Design

Lateral flow devices are commonly known in the art. Briefly, a lateral flow device is an analytical device having as its essence a test strip, through which flows a test sample fluid that is suspected of containing small molecule (e.g., metabolite, NRTI, or compounds described herein, or conjugates or derivatives of same) of interest. The test fluid and any suspended small molecule (e.g., metabolite, NRTI, or compounds described herein, or conjugates or derivatives of same) can flow along the strip to a detection zone in which the small molecule (e.g., metabolite, NRTI, or compounds described herein, or conjugates or derivatives of same) (if present) interacts with a capture agent and a detection agent to indicate a presence, absence, and/or quantity of the small molecule (e.g., metabolite, NRTI, or compounds described herein, or conjugates or derivatives of same).

Numerous lateral flow analytical devices have been disclosed, and include those shown in U.S. Pat. Nos. 4,313,734; 4,435,504; 4,775,636; 4,703,017; 4,740,468; 4,806,311; 4,806,312; 4,861,711; 4,855,240; 4,857,453; 4,943,522; 4,945,042; 4,496,654; 5,001,049; 5,075,078; 5,126,241; 5,451,504; 5,424,193; 5,712,172; 6,555,390; 6,258,548; 6,699,722; 6,368,876 and 7,517,699, each of which is incorporated by reference.

Many lateral flow devices are one-step lateral flow assays in which a biological fluid is placed in a sample area on a bibulous strip (though non-bibulous materials can be used, and rendered bibulous, e.g., by applying a surfactant to the material), and allowed to migrate along the strip until the liquid comes into contact with a specific binding partner (such as an antibody) that interacts with a small molecule (such as the metabolite, NRTI, or any of the compounds described herein) in the liquid. Once a labeled small molecule (such as the metabolite, NRTI, or any of the compounds described herein) interacts with the binding partner, a signal (such as a fluorescent or otherwise visible dye) indicates that the interaction has occurred. Multiple discrete binding partners (such as antibodies) can be placed on the strip (for example in parallel lines) to detect multiple small molecules (such as the metabolites, NRTIs, or any of the compounds described herein) in the liquid. The test strips can also incorporate control indicators, which provide a signal that the test has adequately been performed, even if a positive signal indicating the presence (or absence) of a small molecule (such as the metabolite, NRTI, or any of the compounds described herein) is not seen on the strip.

Lateral flow devices have a wide variety of physical formats that are equally well known in the art. Any physical format that supports and/or houses the basic components of a lateral flow device in the proper function relationship is contemplated by this disclosure.

The basic components of a particular embodiment of a lateral flow device a sample pad, a conjugate pad, a migration membrane, and an absorbent pad.

The sample pad is a component of a lateral flow device that initially receives the sample, and may serve to remove particulates from the sample. Among the various materials that may be used to construct a sample pad (such as glass fiber, woven fibers, screen, non-woven fibers, cellosic fibers or paper) or a cellulose sample pad may be beneficial if a large bed volume is a factor in a particular application. Sample pads may be treated with one or more release agents, such as buffers, salts, proteins, detergents, and surfactants. Such release agents may be useful, for example, to promote resolubilization of conjugate-pad constituents, and to block non-specific binding sites in other components of a lateral flow device, such as a nitrocellulose membrane. Representative release agents include, for example, trehalose or glucose (1%-5%), PVP or PVA (0.5%-2%), Tween 20® (polysorbate 20) or Triton X-100 (polyethylene glycol p-(1,1,3,3-tetramethylbutyl)-phenyl ether) (0.1%-1%), casein (1%-2%), SDS (0.02%-5%), and PEG (0.02%-5%).

With respect to the migration membrane, the types of membranes useful in a lateral flow device include but are not limited to nitrocellulose (including pure nitrocellulose and modified nitrocellulose) and nitrocellulose direct cast on polyester support, polyvinylidene fluoride, or nylon).

The conjugate pad serves to, among other things, hold a detector reagent. Suitable materials for the conjugate pad include glass fiber, polyester, paper, or surface modified polypropylene.

Detector reagent(s) contained in a conjugate pad is typically released into solution upon application of the test sample. A conjugate pad may be treated with various substances to influence release of the detector reagent into solution. For example, the conjugate pad may be treated with PVA or PVP (0.5% to 2%) and/or Triton X-100 (0.5%). Other release agents include, without limitation, hydroxypropylmethyl cellulose, SDS, Brij and β-lactose. A mixture of two or more release agents may be used in any given application.

With respect to the absorbent pad, the pad acts to increase the total volume of sample that enters the device. This increased volume can be useful, for example, to wash away unbound small molecule (e.g., metabolite, NRTI, or any of the compounds described herein, or conjugates or derivatives of same) from the membrane. Any of a variety of materials is useful to prepare an absorbent pad, for example, cellulosic filters or paper. In some device embodiments, an absorbent pad can be paper (i.e., cellulosic fibers). One of skill in the art may select a paper absorbent pad on the basis of, for example, its thickness, compressibility, manufacturability, and uniformity of bed volume. The volume uptake of an absorbent made may be adjusted by changing the dimensions (usually the length) of an absorbent pad.

In operation of the particular embodiment of a lateral flow device, a fluid sample containing a small molecule (such as the metabolite, NRTI, or any of the compounds described herein) of interest, such as one or more small molecule (such as the metabolite, NRTI, or any of the compounds described herein) described herein, is applied to the sample pad. In some examples, the sample may be applied to the sample pad by dipping the end of the device containing the sample pad into the sample (such as urine) or by applying the sample directly onto the sample pad.

From the sample pad, the sample passes, for instance by capillary action, to the conjugate pad. In the conjugate pad, the small molecule (such as the metabolite, NRTI, or any of the compounds described herein), may bind (or be bound by) a mobilized or mobilizable detector reagent, such as an antibody (such as an antibody that recognizes one or more of the small molecule (such as the metabolite, NRTI, or any of the compounds described herein) described herein). For example, a small molecule (such as the metabolite, NRTI, or any of the compounds described herein) may bind to a labeled (e.g., gold-conjugated or colored latex particle-conjugated) antibody contained in the conjugate pad. The small molecule (such as the metabolite, NRTI, or any of the compounds described herein) complexed with the detector reagent may subsequently flow to the test line where the complex may further interact with an small molecule (such as the metabolite, NRTI, or any of the compounds described herein)-specific binding partner (such as an antibody that binds a particular protein, an anti-hapten antibody, or streptavidin), which is immobilized at the proximal test line. In some examples, a small molecule (such as the metabolite, NRTI, or any of the compounds described herein) complexed with a detector reagent (such as gold-conjugated antibody) may further bind to unlabeled, oxidized antibodies immobilized at the proximal test line. The formation of a complex, which results from the accumulation of the label (e.g., gold or colored latex) in the localized region of the proximal test line, is detected. The control line may contain an immobilized, detector-reagent-specific binding partner, which can bind the detector reagent in the presence or absence of the small molecule (such as the metabolite, NRTI, or any of the compounds described herein). Such binding at the control line indicates proper performance of the test, even in the absence of the small molecule (such as the metabolite, NRTI, or any of the compounds described herein) of interest.

In one embodiment, the control line detects the presence of one of IgG, IgD, IgA or another constituent of urine. In one embodiment, the control line detects the presence of one of glycoproteins, secretory IgA, lactoferrin, lysozyme and peroxidase, or another constituent of saliva.

The test results may be visualized directly, or may be measured using a reader (such as a scanner). The reader device may detect color, fluorescence, luminescence, radioactivity, or any other detectable marker derived from the labeled reagent from the readout area (for example, the test line and/or control line).

In another embodiment of a lateral flow device, there may be a second (or third, fourth, or more) test line located parallel or perpendicular (or in any other spatial relationship) to the test line in the test result. The operation of this particular embodiment is similar to that described elsewhere herein with the additional considerations that (i) a second detector reagent specific for a second small molecule (such as the metabolite, NRTI, or any of the compounds described herein), such as another antibody, may also be contained in the conjugate pad, and (ii) the second test line will contain a second specific binding partner having affinity for a second small molecule (such as the metabolite, NRTI, or any of the compounds described herein), such as a second small molecule (such as the metabolite, NRTI, or any of the compounds described herein) in the sample. Similarly, if a third (or more) test line is included, the test line will contain a third (or more) specific binding partner having affinity for a third (or more) small molecule (such as the metabolite, NRTI, or any of the compounds described herein).

In one embodiment, a comparison of the control line to the test line yields the test result from the diagnostic system of the invention. In some instances, a valid result occurs when the control line is detected at a higher intensity level than the test line. For example, a valid result occurs when the control line is at least 5% or more, for example, 10%, 20%, 30%, 40%, 50%, 60%, 70%, 80%, 90%, 100% or more darker than the test line. In some instances, a valid result occurs when the control line is at least 0.5 fold or more, for example, 1 fold, 2 fold, 3 fold, 4 fold, 5 fold, 6 fold, 7 fold, 8 fold, 9 fold, 10 fold or more darker than the test line.

Point of Care Diagnostic and Risk Assessment Systems

The system of the invention can be applied to a point-of-care scenario. U.S. Pat. Nos. 6,267,722, 6,394,952 and 6,867,051 disclose and describe systems for diagnosing and assessing certain medical risks, the contents of which are incorporated herein. The systems are designed for use on site at the point of care, where patients are examined and tested, as well as for operation remote from the site. The systems are designed to accept input in the form of patient data, including, but not limited to biochemical test data, physical test data, historical data and other such data, and to process and output information, such as data relating to a medical diagnosis or a disease risk indicator. The patient data may be contained within the system, such as medical records or history, or may be input as a signal or image from a medical test or procedure, for example, immunoassay test data, blood pressure reading, ultrasound, X-ray or MRI, or introduced in any other form. Specific test data can be digitized, processed and input into the medical diagnosis expert system, where it may be integrated with other patient information. The output from the system is a disease risk index or medical diagnosis.

Point of care testing refers to real time diagnostic testing that can be done in a rapid time frame so that the resulting test is performed faster than comparable tests that do not employ this system. For example, the exemplified immunoassay disclosed and described herein can be performed in significantly less time than the corresponding ELISA assay, e.g., in less than half an hour. In addition, point of care testing refers to testing that can be performed rapidly and on site, such as in a doctor's office, at a bedside, in a stat laboratory, emergency room or other such locales, particularly where rapid and accurate results are required.

In an exemplary embodiment, a point of care diagnostic and risk assessment system includes a reader for reading patient data, a test device designed to be read in the reader, and software for analysis of the data. A test strip device in a plastic housing is designed for use with the reader, optionally including a symbology, such as an alphanumeric character bar code or other machine-readable code, and software designed for analysis of the data generated from the test strip are also provided.

In one embodiment, a reader refers to an instrument for detecting and/or quantitating data, such as on test strips. The data may be visible to the naked eye, but does not need to be visible. Such readers are disclosed and described in the above-incorporated U.S. Pat. Nos. 6,267,722, 6,394,952 and 6,867,051. A reflectance reader refers to an instrument adapted to read a test strip using reflected light, including fluorescence, or electromagnetic radiation of any wavelength. Reflectance can be detected using a photodetector or other detector, such as charge coupled diodes (CCD). An exemplary reflectance reader includes a cassette slot adapted to receive a test-strip, light-emitting diodes, optical fibers, a sensing head, including means for positioning the sensing head along the test strip, a control circuit to read the photodetector output and control the on and off operation of the light-emitting diodes, a memory circuit for storing raw and/or processed data, and a photodetector, such as a silicon photodiode detector. It will be appreciated that a color change refers to a change in intensity or hue of color or may be the appearance of color where no color existed or the disappearance of color.

In one embodiment, a sample is applied to a diagnostic immunoassay test strip, and colored or dark bands are produced. The intensity of the color reflected by the colored label in the test region (or detection zone) of the test strip is, for concentration ranges of interest, directly proportional or otherwise correlated with an amount of small molecule (e.g., metabolite, NRTI, or any of the compounds describe herein, or conjugates or derivatives of same) present in the sample being tested. The color intensity produced is read, in accordance with the present embodiment, using a reader device, for example, a reflectance reader, adapted to read the test strip. The intensity of the color reflected by the colored label in the test region (or detection zone) of the test strip is directly proportional to the amount of small molecule (e.g., metabolite, NRTI, or any of the compounds describe herein, or conjugates or derivatives of same) present in the sample being tested. In other words, a darker colored line in the test region indicates a smaller amount of small molecule (e.g., metabolite, NRTI, or any of the compounds describe herein, or conjugates or derivatives of same), whereas a lighter colored line in the test region indicates a greater amount of small molecule (e.g., metabolite, NRTI, or any of the compounds describe herein, or conjugates or derivatives of same). The color intensity produced, i.e., the darkness or lightness of the colored line, is read visually or using a reader device, for example, a reflectance reader, adapted to read the test strip.

A reflectance measurement obtained by the reader device is correlated to the presence, absence, and/or quantity of small molecule (e.g., metabolite, NRTI, or any of the compounds describe herein, or conjugates or derivatives of same) present in the sample. The reader takes a plurality of readings along the strip, and obtains data that are used to generate results that are an indication of the presence, absence, and/or quantity of small molecule (e.g., metabolite, NRTI, or any of the compounds describe herein, or conjugates or derivatives of same) present in the sample. The system may correlate such data with the presence of a disorder, condition or risk thereof.

As mentioned elsewhere herein, in addition to reading the test strip, the reader may (optionally) be adapted to read a symbology, such as a bar code, which is present on the test strip or housing and encodes information relating to the test strip device and/or test result and/or patient, and/or reagent or other desired information. Typically the associated information is stored in a remote computer database, but can be manually stored. Furthermore, the symbology can be imprinted when the device is used and the information encoded therein.

Health Profile

In one embodiment, the present invention relates to the identification of factors including adherence to one or more medical regimens to generate a health profile for a subject. In one embodiment, a medical regimen is a prophylactic regimen. Accordingly, the present invention features methods for identifying subjects who are at risk of developing the condition(s) for which one or more prophylactic medications are prescribed by detection of the factors and assessing the health profile disclosed herein. These factors or otherwise health profile are also useful for monitoring subjects undergoing treatments and therapies, and for selecting or modifying therapies and treatments to alternatives that would be efficacious in subjects having low rates of adherence when an acceptable alternative is available.

The risk of developing HIV can be assessed by measuring one or more of the factors described herein, and comparing the presence and values of the factors to reference or index values. Such a comparison can be undertaken with mathematical algorithms or formula in order to combine information from results of multiple individual factors and other parameters into a single measurement or index. Subjects identified as having an increased risk of HIV can optionally be selected to receive counseling, an increased frequency of monitoring, or treatment regimens, such as administration of therapeutic compounds. Subjects with HIV can optionally be selected to receive counseling or an increased frequency of monitoring relative to their individual health profile.

The factors of the present invention can thus be used to generate a health profile or signature of subjects: (i) who do not have and are not expected to develop HIV and/or (ii) who have or expected to develop HIV. The health profile of a subject can be compared to a predetermined or reference profile to diagnose or identify subjects at risk for developing HIV, to monitor the adherence to a prophylactic regimen, and to monitor the effectiveness of NRTI or other prophylactic pharmaceuticals. Data concerning the factors of the present invention can also be combined or correlated with other data or test results, such as, without limitation, measurements of clinical parameters or other algorithms for HIV.

Information obtained from the methods of the invention described herein can be used alone, or in combination with other information (e.g., age, race, sexual orientation, vital signs, blood chemistry, etc.) from the subject or from a biological sample obtained from the subject.

Various embodiments of the present invention describe mechanisms configured to monitor, track, and report levels of a prophylactic pharmaceutical in an individual at multiple time points. In one embodiment, the system allows for the collection of data for the presence of a metabolite associated with a prophylactic treatment regimen from multiple samples from an individual. The system can notify the user/evaluator about the likelihood of risk of developing the disorder or condition for which the prophylactic was prescribed when a change (i.e. increase or decrease) in the level of a metabolite associated with a prophylactic pharmaceutical is detected in subsequent samples from a single individual. For example, in some implementations, the system records the presence of a metabolite entered into the system by the user/evaluator or automatically recorded by the system on days 1, 2, 3 and 4 following taking a prophylactic pharmaceutical and applies algorithms to recognize patterns that predict the day at which the individual is at high risk of contracting a disorder in the absence of intervening administration of additional prophylactic. The algorithmic analysis, for example, may be conducted in a central (e.g., cloud-based) system. Data uploaded to the cloud can be archived and collected, such that learning algorithms refine analysis based upon the collective data set of all patients. In some implementations, the system combines quantified clinical features and physiology to aid in diagnosing risk objectively, early, and at least semi-automatically based upon collected data.

In some embodiments, the system is for personal use and tracking by the individual subject. In some embodiment, the data from the system is uploaded to a central system and a provider evaluates the data and makes a diagnosis or recommendation. Providers, in some implementations, may perform a live analysis through real-time data feed between a POCT system and a remote evaluator computing system.

The system has several advantages. The system can be in a form of a kit or an application in the context of an electronic device, such as an electronic hand held device or even a wearable data collection device for convenience. The system is beneficial to providers as well. The providers can evaluate adherence to a treatment regimen from home, during commute, or otherwise away from the office. Further, providers can approve of continued use of a prophylactic without an office visit provided the individual has been adhering to a prescribed regimen. Providers or the individuals themselves may also be altered by the system to transient lapses in a treatment adherence that would suggest an individual may be at increased risk.

In some implementations, the system is used to track an individual's ongoing progress. To enable such ongoing assessment, in some embodiments, applications for assessment may be made available for download to or streaming on a wearable data collection device via a network-accessible content store other content repositories, or other content collections. Content can range in nature from simple text, images, or video content or the like, to fully elaborated software applications ("apps") or app suites. Content can be freely available or subscription based. Content can be stand-alone, can be playable on a wearable data-collection device based on its existing capabilities to play content (such as in-built ability to display text, images, videos, apps, etc., and to collect data), or can be played or deployed within a content-enabling framework or platform application that is designed to incorporate content from content providers. Content consumers, furthermore, can include individuals at risk of contracting HIV or their families as well as clinicians, physicians, and/or educators who wish to incorporate system modules into their professional practices.

In one embodiment, the system for assessing the risk of contracting HIV of the invention can be implemented on a cell phone, tablet computer, a desk top computer, and the likes. In some implementations, in addition to assessment, one or more modules of the system provide training mechanisms for supporting the individual's coping with HIV and its characteristics such as, in some examples, training mechanisms to assist in actions to take when receiving or providing First AID to an individual with HIV.

In one embodiment, the system of the invention can be in a medium that operates automatically behind the scenes in an electronic medical records database/software so that a notice automatically occurs if the data is designated to prompt an alert.

In another embodiment, the system of the invention can be in a format that encompasses "machine learning" so the process and comparator are update and improved as more information is entered and new analogs are developed.

In some embodiments, the invention can be applied to evaluating patient compliance with regimens containing TFV for treatment or prevention of Hepatitis B Virus. Disease In one embodiment, a person diagnosed with HIV may be prescribed a pharmaceutical comprising one or more NRTIs for treatment of HIV. In one embodiment, an individual at risk of contracting HIV may be prescribed a pharmaceutical comprising one or more NRTIs to be taken daily as a preventative measure to reduce the risk of contracting HIV from an exposure incident. Such an individual may be a relative of an individual diagnosed with HIV. Such an individual may be a long term care provider for an individual diagnosed with HIV. Such an individual may be a short term care provider for an individual diagnosed with HIV. Such an individual may be a residential or non-residential partner of an individual diagnosed with HIV. In certain cases, such an individual may participate in research involving HIV or pharmaceuticals for the treatment or prevention of HIV. In some embodiments, a person may be diagnosed with Hepatitis B virus and be prescribed an NRTI for reasons analogous to those given above for HIV.

In one embodiment, the invention provides a system for quickly determining whether an individual has recently (e.g., within one week) taken a NRTI. In one embodiment, the test results can be used to determine whether an individual has taken a pharmaceutical comprising one or more NRTI as prescribed by a provider or research study manager. In one embodiment, the test results can be used to determine whether an individual is at high risk of contracting HIV upon an exposure incident.

In one aspect, the invention is useful because determination of an individual's level of compliance with a prescribed preventative or treatment plan can inform a physician as to future treatment plans for the individual. In one aspect, the invention is useful because determination of an individual's level of compliance with a research study can inform a researcher as to the validity of data gathered for the efficacy of a new NRTI pharmaceutical. For example, if an individual participating in a research study testing a new NRTI uses the invention and the test results indicate that the person has taken the NRTI as prescribed then confidence is provided for the research study results. Alternatively, if the test results indicate that the individual has not taken the NRTI as prescribed then the researcher may determine that the individual should be removed from the ongoing study.

In one embodiment, incentive methods may be provided to improve adherence to a prescription plan wherein an individual is incentivized in any manner to take a pharmaceutical comprising a NRTI and the invention is used to monitor adherence to the prescription plan. Incentive methods are well known in the art and include but are not limited to monetary compensation and gamification.

In one embodiment, the invention relates to urine assays for other medications, including other medications ultimately used as prophylactic or PrEP agents. In one embodiment, the invention relates to point of care assays for other medications, including other medications ultimately used as prophylactic or PrEP agents.

Administration

In some embodiments, the assays or systems as described herein are administered to patients taking a prophylaxis. In some embodiments, the assays or systems as described herein are administered to patients taking a pre-exposure prophylaxis. In some embodiments, the assays or systems as described herein are administered to patients taking an NRTI such as TDF and/or FTC. In some embodiments, the assays or systems as described herein are administered to patients taking a NRTI such as TAF and/or FTC. In some embodiments, the assays or systems as described elsewhere herein are administered to patients taking Truvada™, or any other drug product formulated to contain TDF and/or TAF.

In some embodiments, the assays or systems of the invention are administered to a patient by a provider in a clinical setting during a visit to a healthcare provider or facility. In some embodiments, the assays or systems are used by the patient outside of a clinical setting. In some embodiments, a patient using the assays or systems outside of the clinical setting informs a physician of the results. In some embodiments, a patient using the assays or systems outside of the clinical setting does so independent of reporting the results to a physician.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1

TFV Derivatives (or TFV Analogs)

The TFV derivative T1 was synthesized by Organix, Inc. (Woburn, Mass.), which validated the synthetic route for the TFV derivatives shown in FIG. 1.

Figure 2:
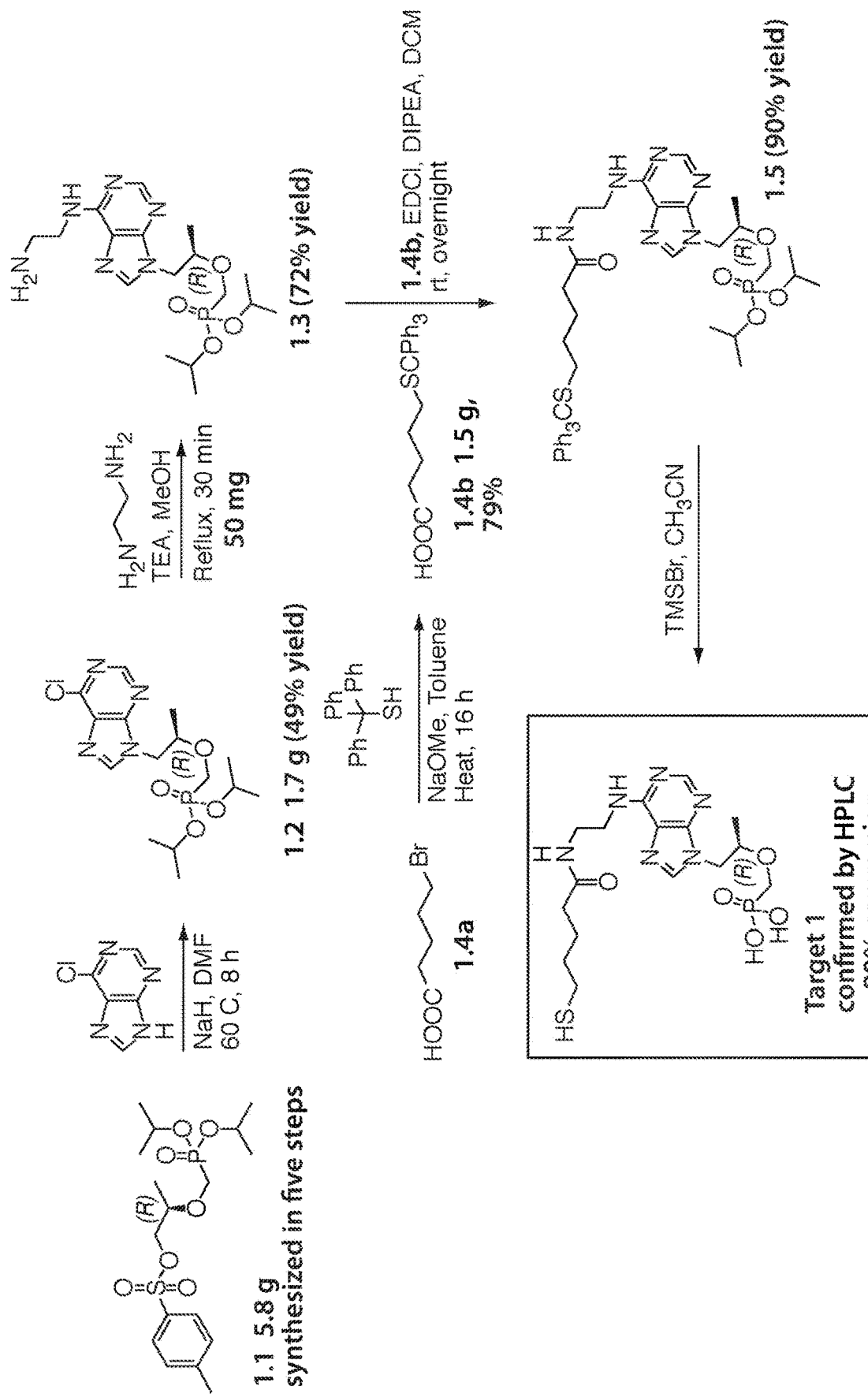
FIG. 2 shows the synthetic route of a tenofovir derivative of the invention, designated Target 1 or T1.

Analog synthesis has been previously described (27,29). The synthetic route to T1 is shown in FIG. 2. Compound 1.1, (R)-2-((diisopropoxyphosphoryl)meth-oxy)propyl 4-methylbenzene-sulfonate compound, was synthesized in five steps per published literature procedures (27,28). Condensation of 1.1 with 6-chloro-9H-purine followed by treatment with ethylene diamine gave amine derivative 1.3 with excellent yield (72%). Coupling of the amino moiety in intermediate 1.3 with acid derivative 1.4b gave the corresponding amide derivative 1.5 with 90% yield. Deprotection of the isopropyl and trityl protecting groups in intermediate 1.5 gave the desired target T1.

This general synthetic route, has also been validated and used to synthesize targets T2-T6. Each TFV derivative yielded approximately >50 mg, and was verified analytically by $^1$H-NMR, LC-MS/MS, and elemental analysis to confirm that their structures and molecular weights are consistent with the TFV derivative. Each TFV derivative yielded ≥95% purity prior to biological evaluation and subsequent use as immunogens.

Example 2

Conjugate of TFV Derivatives (or TFV Analogs) for Generating Antibodies

TFV derivatives as described in Example 1 were conjugated to a carrier protein for rabbit immunization and preparation of detector conjugates. Other animals suitable for immunization and antibody generation are well known in the art and are commercially available, including but not limited to mice, rats, guinea pigs, chickens, and goats.

To make immunogens, the TFV derivatives were conjugated to Keyhole limpet hemocyanin (KLH). KLH and BSA are carrier proteins for small molecule Ab production and generated using published methods (30,31). Other suitable carrier proteins are well known in the art and are commercially available.

TFV derivatives were also used to make HRP conjugates for ELISA use. The proteins (haptens and HRP conjugates) and drug derivatives were linked using standard thiol/maleimide coupling chemistry. The HRP was generated by linking the derivative to a maleimide labeled HRP. The conjugates were prepared utilizing well-established procedures (32).

For antiserum production, rabbits were subsequently immunized with the TFV derivative as soon as they were synthesized and conjugated to KLH. The performance of all TFV derivatives were evaluated as HRP conjugates with the antibodies generated.

Example 3

Production and Screening of Polyclonal Antibodies Raised Against TFV Derivative Conjugates Immunogenic compositions of TFV-derivative conjugates from Example 2 were used to develop polyclonal antibodies (pAbs). The production and screening of pAbs were performed by Calico BioLabs (Pleasanton, Calif.). These pAbs and the ELISA were further develop to qualify raw materials and select rabbits that will be used for the monoclonal antibody (mAbs) production.

Rabbit antibodies are suitable for clinical assays, and generally surpass their rodent counterparts in specificity, affinity, and stability (33-36). Although larger animals such as sheep, goats and donkeys are sometimes preferred because they provide larger blood volumes for pAb production, the specificity of rabbit mAbs is generally higher than that of other species. Rabbit mAbs may be produced rapidly and cost-effectively and new technologies are being used to streamline and improve these processes. Mouse mAbs typically have affinities in the nm range ($10^{-9}$ M), but rabbit mAbs can be produced routinely with affinities of $10^{-10}$ M or even $10^{-12}$ M, in the pm range, 10 to >1000 times higher than mouse mAbs. Rabbits are an excellent species of choice and a current industry standard for producing both polyclonal and monoclonal assay reagents.

Two rabbits were immunized for each of two immunogens comprising the TFV derivative conjugates. Rabbits were boosted using standard protocol, and antisera were collected from each rabbit. pAbs were harvested from the rabbits at 12-day intervals post injection. An acceptable titer of about a 4-fold signal-to-noise ratio at 1:16,000 dilution was utilized. Generally, pAbs with specificity to target small molecules (e.g., metabolites, NRTIs, or any of the compounds described herein, or derivatives and conjugates of same) of over 95% were raised.

pAbs were isolated from the sera by affinity purification using standard procedures of conjugation of the TFV derivatives to agarose beads followed by column chromatography. Approximately 50 mg of affinity-purified pAb were produced from two rabbits. The isolated pAbs were designated "312" and "313".

pAbs were tested in the ELISA assays described below. The final pAbs had an assay curve with adequate slope to allow the separation of +/−25% around the target cut-off concentration. An acceptable PAb also has separation of +/−50% around the target cut-off.

Example 4

Validation of the Polyclonal Antibodies and ELISA Assay

To validate the pAbs generated in Example 3, purified pAbs from Example 3 were used for prototype assay development. Early bleeds for antibody specificity and affinity were screened and evaluated, using the HRP reagents produced in Example 2 and pure TFV as the control. A curve was generated, and the antibodies that have a limit of detection at 1% of the cut-off (10 ng/mL since the cut-off for protective levels of TFV was determined to be 1000 ng/mL by LC-MS/MS) were identified.

Biological Samples

Urine samples including 50 known TFV-positive samples and 50 negative samples from individuals not taking PrEP were collected and de-identified. De-identified samples were quantified for TFV levels on the CHOP LC-MS/MS machine (17). The cut-off for a positive sample was TFV levels >1000 ng/mL. 133 remnant urine samples were collected over a 3-month period. Urine samples from patients known to not be taking TFV were used as a negative control to assess antibody cross-reactivity to any components in urine.

Competition ELISA assay

To test the polyclonal antibodies, a competition assay was performed using the following assay protocol. In this assay, the drug concentration is inversely proportional to the signal generated. The microtiter plate was coated with anti-TFV antibody, and TFV standard or patient sample (with or without drug), or TFV-positive urine, was mixed with an HRP-TFV derivative conjugate and allowed to freely compete for the antibodies on the plate. The solution was detected utilizing a 3,3',5,5'-Tetramethylbenzidine (TMB) substrate followed by stopping the reaction with acid. Absorbance was measured at 450 nm, and drug concentration was determined by color intensity in comparison with a TFV standard curve.

Since the assay uses a competitive format, the random background binding seen with sandwich assays is not a concern. The main issue is cross-reactivity that may occur from substances that do not have apparent structural similarity. The specificity of the ELISA was evaluated with clinical samples in the urine bank, which was confirmed to be TFV-negative to establish baseline specificity performance. Issues related to cross reactivity or matrix interference were identified and a "problematic" sample bank was generated. This bank was further used as part of the final criteria to select from the series of mAb clones that were generated. The sensitivity of the assay was evaluated by testing 100 samples known to be positive for TFV: 50 TVF-negative serum samples spiked with purified TVF at 50% of the cut-off concentration, and 50 samples spiked at 150% of the cut-off. Interim performance was established for the polyclonal assay to provide a baseline to judge the improvement of performance of the mAbs.

The competitive ELISA was further validated against the urine TFV Mass Spectrometry test, which has a previously validated cut-off of 1000 ng/mL. The MS test can serve as a standard to generate sufficient power for our sensitivity and specificity goals with 50 banked clinical samples positive for TFV and 50 banked negative samples in addition to the 100 unique spiked samples.

An ELISA can detect TFV in urine bank samples with known concentrations with sensitivity >90% and specificity >90%. This ELISA can be used as a control system to evaluate and qualify mAbs.

Assay Protocol and Procedure

A. Conjugate HRP

Conjugate:
1. Reconstitute 5 mg of EZ-Link™ Maleimide Activated HRP powder in 5 ml of
2. Add 1 mg of HRP=>1 mL to Eppendorf tube
3. Add 1 mg of derivative=>50 uL to tube
4. Allow to incubate at RT for 3 hrs Gravity Filter-PD10 Column:
5. Remove top cap and pour off column storage
6. Cut sealed end of column notch
7. Fill up column with equilibration buffer—5 mL
8. Allow buffer to enter packed bed completely
9. Repeat 4 times
10. Add sample and add equilibration buffer to total 2.5 mL
11. Let sample enter bed completely and collect flow thru in collection tube
12. Place and eluate collection tube under apparatus
13. Elute with 3.5 mL of buffer
14. Collect eluate and store at 4 C
15. Dilute with StabilZyme® HRP Conjugate to appropriate concentration=>1:1,000

B. Tenofovir (TFV) Standards Series

Tenofovir-SigmaAldrich® #SML1795
1. Measure 10 mg of powder into 15 mL conical tube
2. Add 10 mL of water=>Concentration of lmg/mL
3. Prepare appropriate dilutions in PBS
   2,000 ng/mL standard
   1,000 ng/mL standard
   500 ng/mL standard
   10 ng/mL standard C. ELISA Protocol—Antibody Coated Plate Format
1. Coat Greiner Bio-one polystyrene 96 well plate with 0.5 ug/well of antibody—50 μl/well of a 1:100 antibody 313 dilution in PBS
2. Allow to incubate for 2 hrs at Room Temperature or overnight at 4° C.
3. Wash plate 200 μl/well 4× in TBST (0.1% Tween20®/TBS) with Aqua Max® 2000 plate washer
4. Block with 200 μl/well of 2% BSA in TBST for 1 hour at RT
5. Aspirate Blocking Buffer from wells
6. Add 50 μl of TFV standard or sample to well—Plate each sample or standard in duplicates
7. Incubate 30 minutes at room temperature
8. Add 50 μl of HRP conjugate at concentration of 1:1,000
9. Mix well and incubate at Room Temperature 1 hr
10. Aspirate volume from wells
11. Wash plate 200 μl/well 4×in TBST (.1 % Tween20LVTBS) with AquaMax® 2000 plate washer
12. Add 50 μl of TMB
13. Incubate 5 minutes at RT
14. Add 50 μl of Stop Solution (0.25M Sulphuric Acid)
15. Read plate at 450 nm with SpectraMax® 13×

Results

Figure 3:
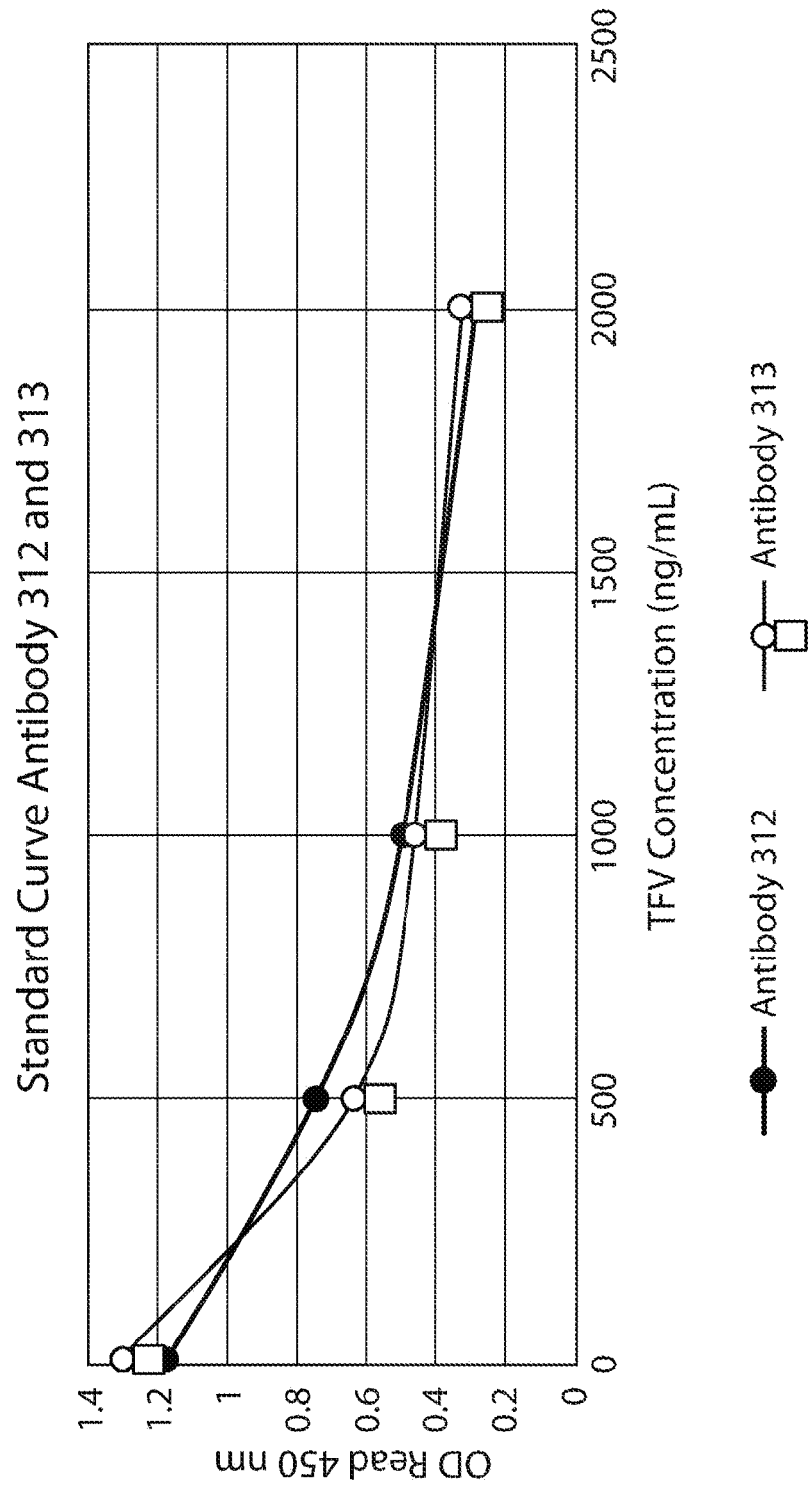
FIG. 3 depicts competition ELISA assays using anti-TFV derivative conjugate polyclonal antibodies. In this assay, anti-TFV derivative conjugate polyclonal antibodies "312" and "313" are coated on a microplate and TFV standard was mixed with an HRP-TFV conjugate and allowed to freely compete for antibodies on the plate. The solution was detected utilizing TMB substrate followed by stopping the reaction with acid. Absorbance was measured at 450 nm, and drug concentration was determined by color intensity in comparison with a TFV standard curve. Antibodies 312 and 313 were able to produce an acceptable calibration curve and allowed resolution around the cut-off of 1,000 ng/ml. There was 7.54 standard deviation separation between 500 and 1,000 ng/ml (CV=12.0%) and 6.28 standard deviation between 1,000 and 2,000 ng/ml (CV=4.4%) for antibody 313. This indicates that antibodies 312 and 313 have sufficient sensitivity to tenofovir.

ELISA results are depicted in Table 2 and FIG. 3. The data in Table 2 represents the standard curve of free drug (tenofovir) diluted in PBS at the designated concentrations. Antibody "312" and "313" were able to produce an acceptable calibration curve and allowed resolution around the cut-off of 1,000 ng/ml. There was 7.54 standard deviation separation between 500 and 1,000 ng/ml (CV=12.0%) and 6.28 standard deviation between 1,000 and 2,000 ng/ml (CV=4.4%) for antibody 313. This indicates that antibody 312 and 313 have sufficient sensitivity to tenofovir.

TABLE 2

ELISA results

| Standards | pAb 312 | pAb 313 |
|---|---|---|
| 10 | 1.18 | 1.306 |
| 500 | 0.749 | 0.642 |
| 1,000 | 0.493 | 0.463 |
| 2,000 | 0.286 | 0.328 |

Example 5

Specificity of the Polyclonal Antibodies for Tenofovir

The data in Table 3 compares the specificity of each antibody based on 50 clinical urine samples that were positive for tenofovir (urine TFV level>1,000 ng/mL on validated LC-MS) and 50 clinical urine samples that were negative for Tenofovir (urine TFV level<10 ng/mL on validated LC-MS). Both polyclonal antibodies 312 and 313 correctly identified 50 out of 50 samples as TFV positive. For the TFV negative samples, Antibody 312 was cross reactive with 27 samples out of 50 while Antibody 313 was cross reactive with 24 samples out of 50. This indicates that pAb 313 has slightly less cross reactivity than pAb 312.

TABLE 3

Comparison of antibody 312 and 313 specificity

|  | LC-MS(+) | LC-MS(−) |
|---|---|---|
| Antibody 312 (+) |  |  |
| (+) | 50 | 27 |
| (−) | 0 | 23 |
| Antibody 313 (+) |  |  |
| (+) | 50 | 24 |
| (−) | 0 | 26 |

To identify which compounds were causing cross reactivity, potentially cross reactive compounds (compounds with similar chemical structure to TFV) were spiked in buffer and tested that with the pAbs. We tested 11 compounds and their percent cross reactivity was calculated for each of the substances in Table 3 to each antibody. Four compounds were identified that exhibited some measure of cross reactivity with pAb 313 versus three in pAb 312. Since the recombinant and subclone monoclonal antibodies described herein can be screened against these compounds, this data provided further justification for proceeding to mAb development with pAb 313 over pAb 312.

TABLE 4

Cross reactivity of pAbs 313 and 312
Cross Reactive Compound Bank

| Compound | Cross Reactivity of 313 (vs TFV standard) | Cross Reactivity of 312 (vs TFV standard) |
|---|---|---|
| Adefovir | Slightly Cross Reactive (0.1%) | Slightly Cross Reactive (0.1%) |
| Adenosine | Slightly Cross Reactive (0.1%) | None |
| Adenosine 3' Monophosphate | Slightly Cross Reactive (0.1%) | Slightly Cross Reactive (0.1%) |
| Adenosine 5' Monophosphate Monohydrate | None | None |
| Adenosine 5' Triphosphate Disodium | None | None |
| Cidofovir Hydrate | Moderately Cross Reactive (5%) | None |
| Guanosine 5' Monophosphate Disodium | None | None |
| N6 Methyladenosine 5'Monophosphate | None | Slightly Cross Reactive (0.1%) |
| N6 Methyladenosine | None | None |
| 2' Deoxyadenosine 5' Triphosphate | None | None |
| 2'Deoxyguanosine 5'Triphosphate | None | None |

Conclusion:

Based on the results of these validation studies, it was confirmed that the antibodies generated by the derivative conjugates described herein were sensitive for both free TFV and for TFV in clinical samples of urine. Further pAb "313" was chosen as the candidate for producing an mAb, with the option of returning to pAb "312" if needed.

Example 6

Validation of a Urine Assay to Measure Tenofovir Level in Patients Taking Tenofovir Alafenamide Blood and urine samples were collected from 3 cohorts of patients: (1) 10 HIV positive participants with suppressed virus on a TAF-based regimen, (2) 10 HIV-participants administered 1 dose of FTC/TAF followed by urine and plasma sampling for 7 days starting 1-3 hours post-dose, and (3) 10 HIV-participants administered 7 daily doses of FTC/TAF followed by urine and plasma sampling for 10 days starting 1-3 hours after the last dose. Samples were analyzed using liquid chromatography-tandem mass spectrometry (LC-MS/MS) with high sensitivity and specificity for TFV. Samples from cohort 2 were compared to a historical cohort administered one dose of FTC/TDF.

Figure 4:
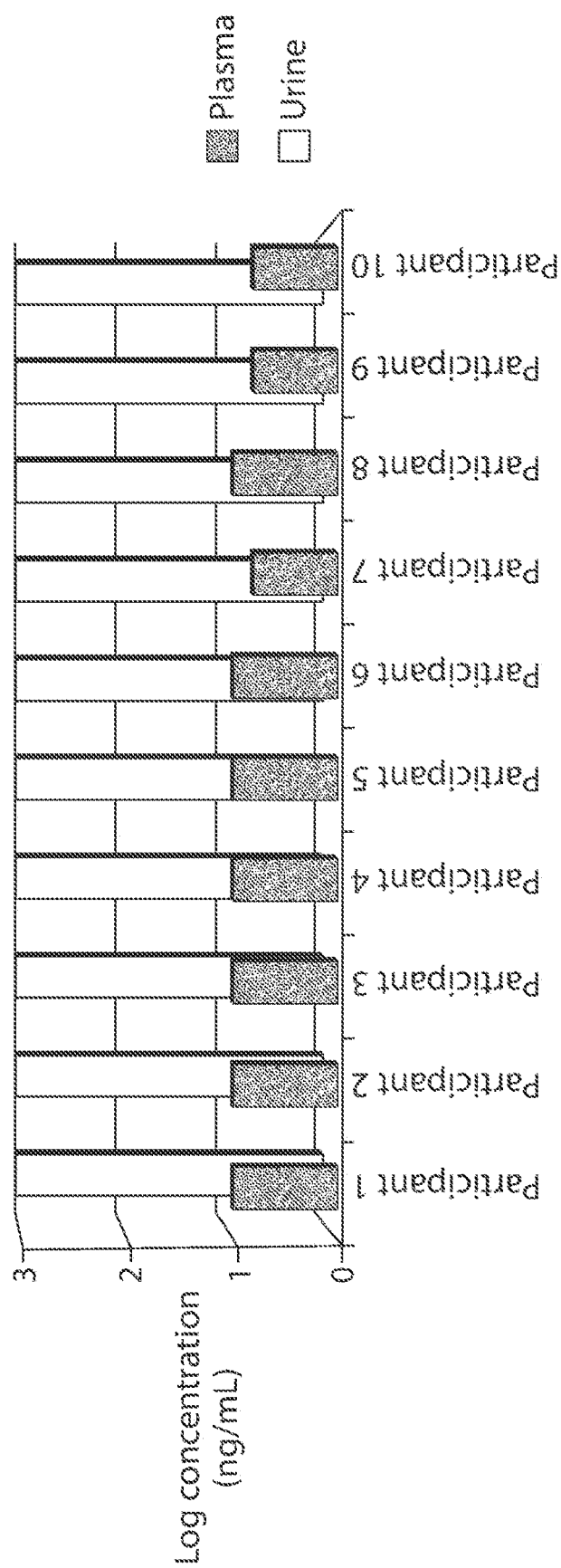
FIG. 4 shows the relationship between urine and plasma TFV concentrations in HIV+ patients taking TAF (Cohort 1).
Figure 5:
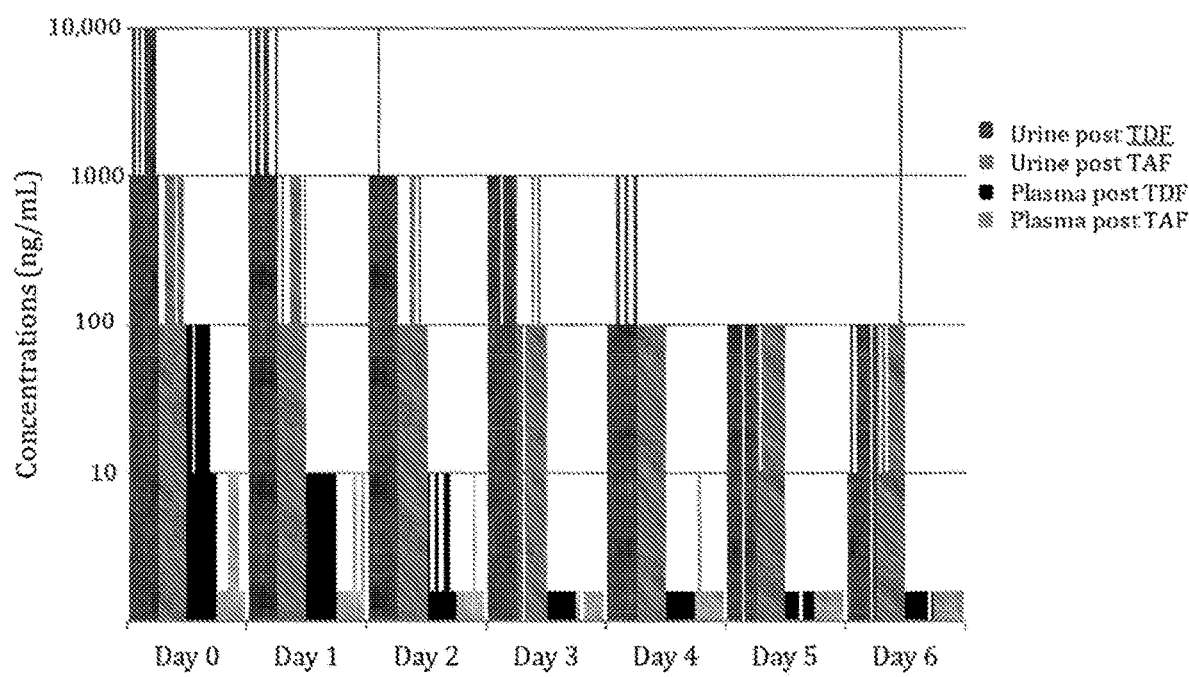
FIG. 5 shows urine/plasma TFV concentrations after single dose of FTC/TAF in 10 HIV-negative subjects, with comparison to historical cohort of subjects given one single dose of FTC/TDF.
Figure 6:
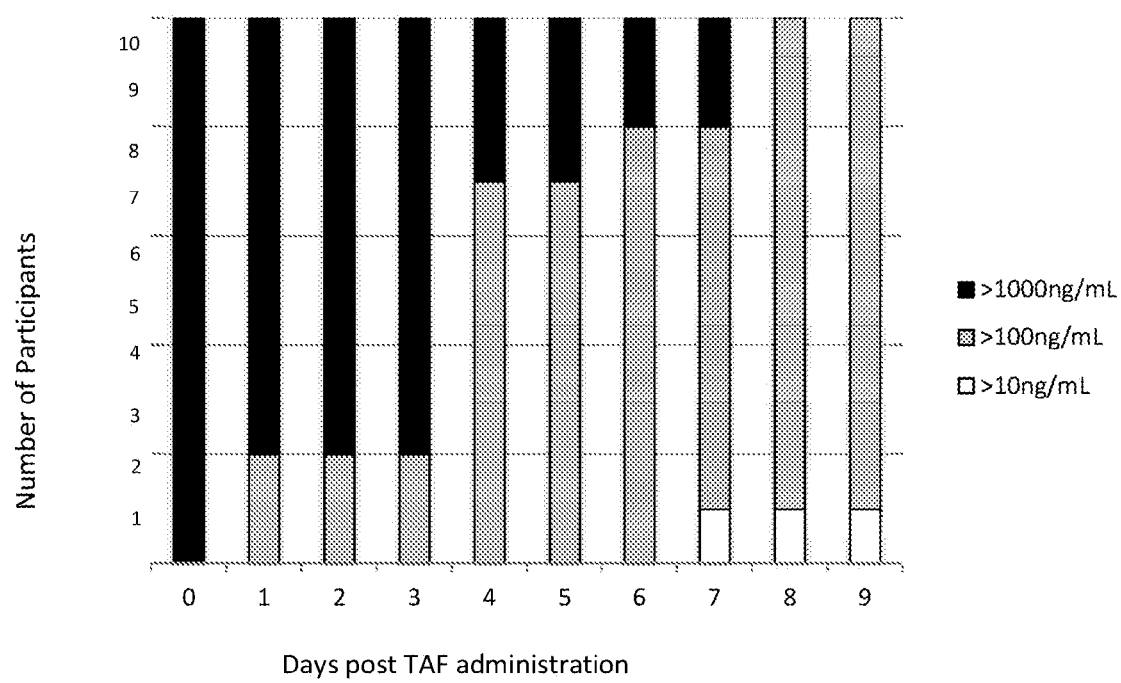
FIG. 6 shows urine TAF concentrations following 7 consecutive doses of FTC/TAF in 10 HIV-negative subjects (Cohort 3).

HIV positive participants were 90% male, 40% African American, and 10% Hispanic (median age=53.5y; Range=51-79y). HIV treatment regimens included TAF plus one of the following: dolutegravir (3), boosted elvitegravir (3), boosted darunavir (2), raltegravir (1), or rilpivirine (1). HIV negative participants were 55% male and 70% Caucasian (median age=30.5y; Range=23-47y). Urine samples from HIV-positive participants demonstrated TFV concentrations 2 logs higher in urine than plasma (1000 ng/mL vs. 10 ng/mL, respectively) (FIG. 4). Urine samples following a single dose of FTC/TAF in HIV-subjects yielded TFV concentrations ranging from 100-1000 ng/mL 1-3 hours post-dose, with TFV concentration remaining >100 ng/mL for 6 days in 8 of 10 participants. These concentrations were comparable to those from a historical cohort administered FTC/TDF, although urine TFV concentration rose more rapidly after medication ingestion in subjects receiving FTC/TDF and were, on average, higher for the first 4 days after discontinuation of medication compared to those receiving FTC/TAF (FIG. 5). Urine samples collected after 7 consecutive doses of FTC/TAF yielded TFV concentrations >1000 ng/mL 1-3 hours after discontinuation of dosing with TFV levels >100 ng/mL up to 7 days post discontinuation in 8 out of 10 participants (FIG. 6). Plasma TFV concentrations were low (≤10 ng/mL) in both HIV-negative cohorts at all time points.

TFV persists in urine at detectable concentrations in patients taking FTC/TAF for at least 7 days despite largely undetectable plasma levels, with urine TFV concentrations comparable to patients taking FTC/TDF. This study demonstrates the feasibility of using a urine TFV assay to assess TAF adherence with reduced opportunity for "white-coat" adherence given a difference in single dose vs steady state TFV concentration patterns in this study. Future studies should address the differences in urinary TFV clearance patterns between TDF- and TAF-based regimens.

REFERENCES

1. HIV Surveillance Report, 2014 [Internet]. Centers for Disease Control and Prevention; 2016 November [cited 2017 Aug. 12].
2. FACT SHEET JULY 2017 [Internet]. UNAIDS; 2017 July
3. Number of Deaths Due to HIV/AIDS. [Internet]. World Health Organization Global Health Observatory; 2016 April
4. Smith D K et al. *MMWR Morb Mortal Wkly Rep.* 2015 Nov. 27; 64(46):1291-5.
5. U.S. Federal Funding for HIV/AIDS: The President's FY 2016 Budget Request. Kaiser Family Foundation; 2016 April
6. Kearney B P et al. *Clin Pharmacokinet.* 2004; 43(9):595-612.
7. Prejean J et al. *EPloS One.* 2011; 6(8):e17502.
8. Grant R M et al. *N Engl J Med.* 2010 Dec. 30; 363(27):2587-99.
9. Amico K R et al. *J Acquir Immune Defic Syndr* 1999.2014 Aug. 15; 66(5):530-7.
10. Hosek S G et al. *J Acquir Immune Defic Syndr* 1999.2013 Apr. 1; 62(4):447-56.
11. Amico K R et al. *AIDS Behav.* 2013 July; 17(6):2143-55.
12. Van Damme L et al. *N Engl J Med.* 2012 Aug. 2; 367(5):411-22.
13. Golin C E et al. *J Gen Intern Med.* 2002 October; 17(10):756-65.
14. Hawkins T et al. *J. Acquir Immune Defic Syndr* 1999.2005 Aug. 1; 39(4):406-11.
15. Koenig H C et al. *HIV Med.* 2017 July; 18(6):412-8.
16. Bush S et al. Significant uptake of truvada for pre-exposure prophylaxis (PrEP) utilization in the US in late 2014-1Q 2015. [Internet]. IAPAC Treatment, Prevention, and Adherence Conference; 2015 Jun. 28; Miami, Fla.
17. Preexposure prophylaxis for the prevention of HIV infection in the united states—2014 clinical practice guideline. [Internet]. The Centers for Disease Control and Prevention; 2016 April.
18. World Health Organization. Guidance on Pre-Exposure Oral Prophylaxis (PrEP) for Serodiscordant Couples, Men and Transgender Women Who Have Sex with Men at High Risk of HIV: recommendations for Use in the Context of Demonstration Projects. Geneva: World Health Organization; 2012.
19. Gilead Sciences (GILD) Q2 2017 Results—Earnings Call Transcript [Internet]. 2017 July [cited 2017 Aug. 8].
20. Hiemke C. *Eur J Clin Pharmacol.* 2008 Feburary; 64(2):159-66.
21. Brünen S et al. Medication adherence determined by therapeutic drug monitoring in psychiatric outpatients with co-morbid substance abuse disorders. Pharmacopsychiatry [Internet]. 2011 September [cited 2017 Sep. 1]; 44(6).
22. Brinker S et al. *J Am Coll Cardiol.* 2014 Mar. 4; 63(8):834-5.
23. Koenig H. URINE TENOFOVIR TESTING TO MEASURE PREP ADHERENCE AMONG YOUTH IN A REAL WORLD SETTING. Conference on Retroviruses and Opportunistic Infections; 2017 Mar. 5; Boston, Mass.
24. Clevenbergh P et al. *AIDS Lond Engl.* 2002 Nov. 22; 16(17):2311-5.
25. Nettles R E et al. *Clin Infect Dis Off Publ Infect Dis Soc Am.* 2006 Apr. 15; 42(8):1189-96.
26. Wertheimer B Z et al. *HIV Clin Trials.* 2006 April; 7(2):59-69.
27. Liu A Y et al. *PloS One.* 2014; 9(1):e83736.
28. Delahunty T et al. *J Chromatogr B Analyt Technol Biomed Life Sci.* 2006 Jan. 2; 830(1):6-12.
29. Nirogi R et al. *Biomed Chromatogr BMC.* 2009 April; 23(4):371-81.
30. Cesnek M et al. *Bioorg Med Chem.* 2008 Jan. 15; 16(2):965-80.
31. Holy A et al. *Collect Czechoslov Chem Commun.* 1995; 60(8):1390-409.

32. Lalley-Cherczko L et al. HIV Research for Prevention; 2016 Oct. 18; Chicago, Ill.

INCORPORATION BY REFERENCE

The contents of all references, patent applications, patents, and published patent applications, as well as the Figures and the Sequence Listing, cited throughout this application are hereby incorporated by reference in their entirety as if each individual publication or patent was specifically and individually incorporated by reference. In case of conflict, the present application, including any definitions herein, may control.

EQUIVALENTS

It will be understood by those skilled in the art that various changes in form and details may be made therein without departing from the spirit and scope of the invention as set forth in the appended claims. Those skilled in the art will recognize, or be able to ascertain using no more than routine experimentation, many equivalents to the specific embodiments of the invention described herein. While specific embodiments of the subject invention have been discussed, the above specification is illustrative and not restrictive. Many variations of the invention may become apparent to those skilled in the art upon review of this specification. The full scope of the invention should be determined by reference to the claims, along with their full scope of equivalents, and the specification, along with such variations. Such equivalents are intended to be encompassed by the following claims.

What is claimed is:

1. An isolated antibody that specifically binds to tenofovir, wherein the antibody comprises:
   (1) immunoglobulin variable light chain CDRs according to SEQ ID NOs: 17, 25, and 33, respectively, and immunoglobulin variable heavy chain CDRs according to SEQ ID NOs: 18, 26, and 34, respectively;
   (2) immunoglobulin variable light chain CDRs according to SEQ ID NOs: 19, 27, and 35, respectively, and immunoglobulin variable heavy chain CDRs according to SEQ ID NOs: 20, 28, 36, respectively;
   (3) immunoglobulin variable light chain CDRs according to SEQ ID NOs: 21, 29, and 37, respectively, and immunoglobulin variable heavy chain CDRs according to SEQ ID NOs: 22, 30, 38, respectively; or
   (4) immunoglobulin variable light chain CDRs according to SEQ ID NOs: 23, 31, and 39, respectively, and immunoglobulin variable heavy chain CDRs according to SEQ ID NOs: 24, 32, and 40, respectively.

2. The isolated antibody of claim 1, wherein the antibody comprises an immunoglobulin variable light chain region comprising an amino acid sequence of SEQ ID NO: 41 and an immunoglobulin variable heavy chain region comprising an amino acid sequence of SEQ ID NO: 42.

3. An isolated nucleic acid molecule encoding the antibody of claim 1, wherein the isolated nucleic acid is selected from the group consisting of a cloning vector, an expression vector, a heterologous recombination vector and a viral integration vector.

4. A cell transformed with the isolated nucleic acid of claim 3, wherein the cell is selected from the group consisting of rabbit, hamster, mouse, rat, chicken, goat, monkey, sheep, pig, horse, cow, and human.

5. A method of detecting tenofovir in a biological fluid sample of a subject, comprising contacting the antibody of claim 1 with a biological fluid sample from the subject.

6. A method for performing a lateral flow assay to detect tenofovir in a fluid sample, the method comprising the steps of:
(a) applying the fluid sample to a sample pad;
(b) allowing the sample to flow laterally along the sample pad to a conjugated label pad that is in fluid communication with the sample pad and comprises a labeled first reagent specific for tenofovir, wherein a portion of the conjugated label pad and a portion of the sample pad forms a first interface;
(c) allowing the labeled first reagent to bind tenofovir, if present in the fluid sample, to form a labeled first reagent-tenofovir complex;
(d) allowing the sample to flow laterally along the conjugated label pad to a membrane that is in fluid communication with the conjugated label pad, wherein a portion of the conjugated label pad and a portion of the membrane forms a second interface, wherein the membrane comprises a second reagent bound to the membrane to form a test line, and wherein the second reagent can bind the labeled first reagent;
(e) allowing the labeled first reagent to bind to the second reagent to form a labeled first reagent-second reagent complex at the test line; and
(f) detecting the label at the test line,
wherein the first reagent is an antibody comprising:
(1) immunoglobulin variable light chain CDRs according to SEQ ID NOs: 17, 25, and 33, respectively, and immunoglobulin variable heavy chain CDRs according to SEQ ID NOs: 18, 26, and 34, respectively;
(2) immunoglobulin variable light chain CDRs according to SEQ ID NOs: 19, 27, and 35, respectively, and immunoglobulin variable heavy chain CDRs according to SEQ ID NOs: 20, 28, 36, respectively;
(3) immunoglobulin variable light chain CDRs according to SEQ ID NOs: 21, 29, and 37, respectively, and immunoglobulin variable heavy chain CDRs according to SEQ ID NOs: 22, 30, 38, respectively; or
(4) immunoglobulin variable light chain CDRs according to SEQ ID NOs: 23, 31, and 39, respectively, and immunoglobulin variable heavy chain CDRs according to SEQ ID NOs: 24, 32, and 40, respectively.

7. The method of claim 6, wherein the membrane is nitrocellulose.

8. The method of claim 6, wherein the membrane further comprises a third reagent bound to the membrane downstream or upstream of the test line to form a control line.

9. The method of claim 8, wherein the third reagent binds to the labeled first reagent to cause the label to form a detectable signal at the control line, wherein the presence of the detectable signal at the control line indicates proper performance of the lateral-flow assay.

10. The method of claim 6, comprising the steps of:
(a) applying the fluid sample to a sample pad;
(b) allowing the sample to flow laterally along the sample pad to a conjugated label pad that is in fluid communication with the sample pad and comprises a labeled first reagent specific for tenofovir, wherein a portion of the conjugated label pad and a portion of the sample pad forms a first interface;
(c) allowing the labeled first reagent to bind tenofovir, if present in the fluid sample, to form a labeled first reagent-tenofovir complex;
(d) allowing the sample to flow laterally along the conjugated label pad to a membrane that is in fluid communication with the conjugated label pad, wherein a portion of the conjugated label pad and a portion of the membrane forms a second interface, wherein the membrane comprises a second reagent bound to the membrane to form a test line, and wherein the second reagent is can bind the labeled first reagent when the labeled first reagent is not bound to tenofovir in the fluid sample; and
(e) if tenofovir is absent in the fluid sample, allowing the labeled first reagent to bind to the second reagent to form a labeled first reagent-second reagent complex at the test line, or if tenofovir is present in the fluid sample, allowing the labeled first reagent-tenofovir complex to flow past the test line without binding the second reagent; and
(f) detecting the labeled first reagent-second reagent at the test line, wherein detecting the detectable signal indicates the absence of tenofovir in the fluid sample.

11. The method of claim 6, wherein the fluid sample is a urine sample from a patient, wherein the patient is prescribed or administered tenofovir or a prodrug thereof.

12. The method of claim 6, wherein the antibody comprises immunoglobulin variable light chain CDRs according to SEQ ID NOs:23, 31, 39, respectively, and immunoglobulin variable heavy chain CDRs according to SEQ ID NOs: 24, 32, 40, respectively.

13. The method of claim 12, wherein the antibody comprises an immunoglobulin variable light chain region according to SEQ ID NO: 41 and an immunoglobulin variable heavy chain region according to SEQ ID NO: 42.

14. A device for performing a lateral flow assay to detect tenofovir in a fluid sample, the device comprising:
(a) a sample pad for receiving the fluid sample;
(b) a conjugated label pad located downstream of the sample pad comprising a labeled first reagent specific for tenofovir, wherein a portion of the conjugated label pad and a portion of the sample pad form a first interface;
(c) a membrane located downstream of the conjugated label pad, wherein a portion of the membrane and a portion of the conjugated label pad form a second interface; and
(d) a second reagent bound to the membrane to form a test line, wherein the second reagent is capable of binding the labeled first reagent,
wherein the first interface allows the fluid sample to flow from the sample pad to the conjugated label pad and contact the labeled first reagent, and the second interface allows the fluid sample to flow from the conjugated label pad to the membrane and to contact the second reagent to form a labeled first reagent-second reagent complex and cause the label to form a detectable signal at the test line, wherein the first reagent is an antibody comprising:
(1) immunoglobulin variable light chain CDRs according to SEQ ID NOs: 17, 25, and 33, respectively, and immunoglobulin variable heavy chain CDRs according to SEQ ID NOs: 18, 26, and 34, respectively;
(2) immunoglobulin variable light chain CDRs according to SEQ ID NOs: 19, 27, and 35, respectively, and immunoglobulin variable heavy chain CDRs according to SEQ ID NOs: 20, 28, 36, respectively;
(3) immunoglobulin variable light chain CDRs according to SEQ ID NOs: 21, 29, and 37, respectively, and immunoglobulin variable heavy chain CDRs according to SEQ ID NOs: 22, 30, 38, respectively; or (4) immunoglobulin variable light chain CDRs according to SEQ ID NOs: 23, 31, and 39, respectively, and immunoglobulin variable heavy chain CDRs according to SEQ ID NOs: 24, 32, and 40, respectively.

15. The device of claim 14, wherein the membrane is nitrocellulose.

16. The device of claim 14, wherein the membrane further comprises a third reagent bound to the membrane downstream or upstream of the test line to form a control line.

17. The device of claim 16, wherein the third reagent binds to the labeled first reagent to cause a detectable signal at the control line, wherein the presence of the detectable signal at the control line indicates proper performance of the lateral-flow assay.

18. A kit, comprising:
(a) a sample collection receptacle for receiving a biological sample; and
(b) the device of claim 14 for assaying the biological sample.

* * * * *